United States Patent
Economides et al.

(10) Patent No.: US 12,344,665 B2
(45) Date of Patent: Jul. 1, 2025

(54) TREATMENT OF FIBRODYSPLASIA OSSIFICANS PROGRESSIVA BY ADMINISTRATION OF AN ANTI-ACTIVIN A ANTIBODY

(71) Applicant: Regeneron Pharmaceuticals, Inc., Tarrytown, NY (US)

(72) Inventors: Aristides Economides, Tarrytown, NY (US); Eduardo Forleo Neto, Greenwich, CT (US); Dinko Gonzalez Trotter, Baldwin Place, NY (US); Gary Herman, Princeton, NJ (US); Andrew Rankin, Stamford, CT (US); Scott Mellis, New Rochelle, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 373 days.

(21) Appl. No.: 17/144,385

(22) Filed: Jan. 8, 2021

(65) Prior Publication Data
US 2021/0253685 A1    Aug. 19, 2021

Related U.S. Application Data

(60) Provisional application No. 63/081,428, filed on Sep. 22, 2020, provisional application No. 63/076,691, filed on Sep. 10, 2020, provisional application No. 62/958,448, filed on Jan. 8, 2020.

(51) Int. Cl.
| | |
|---|---|
| *A61K 39/395* | (2006.01) |
| *A61P 19/02* | (2006.01) |
| *C07K 16/22* | (2006.01) |
| *A61K 39/00* | (2006.01) |

(52) U.S. Cl.
CPC .......... *C07K 16/22* (2013.01); *A61K 39/3955* (2013.01); *A61P 19/02* (2018.01); *A61K 2039/505* (2013.01); *C07K 2317/21* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2016/0075772 A1* | 3/2016 | Hatsell | C07K 16/18 424/134.1 |
| 2017/0211070 A1 | 7/2017 | Hino et al. | |

FOREIGN PATENT DOCUMENTS

| | | |
|---|---|---|
| WO | 2016/039796 A2 | 3/2016 |

OTHER PUBLICATIONS

Makaddam et al. (Bone 109: 147-152, 2018).*
Labonty et al. (Dev. Dyn. 247(2): 279-288, 2018).*
Wentworth et al. (Br. J. Clin. Pharmacol. 85: 1180-1187, 2019), epub Jan. 6, 2019.*
PRIME continuing education material accessed Aug. 30, 2023 at: https://media.primeinc.org/upload/programs/31WB223/Expert%20Insights%20on%20Evolving%20Treatment%20and%20Management%20Approaches%20in%20FOP.pdf.*
Eekhoff et al. (Bone 109: 143-146, 2018).*
Drake et al., The Rare Bone Disease Working Group: report from the 2016 American Society for Bone and Mineral Research Annual Meeting. Bone. Sep. 2017; 102:80-84.
Hatsell et al., CVR1R206H receptor mutation causes fibrodysplasia ossificans progressiva by imparting responsiveness to activin A. Sci Transl Med. Sep. 2, 2015;7(303):303ra137.

* cited by examiner

*Primary Examiner* — Christine J Saoud
(74) *Attorney, Agent, or Firm* — McCarter & English, LLP; Marcie B. Clarke

(57) ABSTRACT

Methods for treating fibrodysplasia ossificans progressiva (FOP) in human subjects are provided. Such methods involve administering to a subject having FOP a therapeutically effective amount of an activin A antagonist, such as an antibody against activin A.

17 Claims, 13 Drawing Sheets
Specification includes a Sequence Listing.

FIGURE 10

Heavy Chain

```
QVQLQESGPG LVKPSETLSL TCTVSGGSFS SHFWSWIRQP PGKGLEWIGY ILYTGGTSFN 60
PSLKSRVSMS VGTSKNQFSL KLSSVTAADT AVYYCARARS GIFFTGIIVP GSFDIWGQGT 120
MVTVSSASTK GPSVFPLAPC SRSTSESTAA LGCLVKDYFP EPVTVSWNSG ALTSGVHTFP
AVLQSSGLYS LSSVVTVPSS SLGTKTYTCN VDHKPSNTKV DKRVESKYGP PCPPCPAPEF
CPPC
LGGPSVFLFP PKPKDTLMIS RTPEVTCVVV DVSQEDPEVQ FNWYVDGVEV HNAKTKPREE
QFNSTYRVVS VLTVLHQDWL NGKEYKCKVS NKGLPSSIEK TISKAKGQPR EPQVYTLPPS
QEEMTKNQVS LTCLVKGFYP SDIAVEWESN GQPENNYKTT PPVLDSDGSF FLYSRLTVDK
SRWQEGNVFS CSVMHEALHN HYTQKSLSLS LGK
                                  SEQ ID NO:25
```

Light Chain

```
EIVLTQSPGT LSLSPGERAT LSCRASQSVS SSYLAWYQQK PGQAPRLLIY GASSRATGIP
DRFSGSGSGT DFTLTISRLE PEDFAVYYCQ QYGSSPWTFG QGTKVEIKRT VAAPSVFIFP
PSDEQLKSGT ASVVCLLNNF YPREAKVQWK VDNALQSGNS QESVTEQDSK DSTYSLSSTL
TLSKADYEKH KVYACEVTHQ GLSSPVTKSF NRGEC
                                  SEQ ID NO:26
```

US 12,344,665 B2

TREATMENT OF FIBRODYSPLASIA OSSIFICANS PROGRESSIVA BY ADMINISTRATION OF AN ANTI-ACTIVIN A ANTIBODY

RELATED APPLICATIONS

The instant application claims priority to U.S. Provisional Application No. 62/958,448, filed on Jan. 8, 2020; U.S. Provisional Application No. 63/076,691, filed on Sep. 10, 2020; and U.S. Provisional Application No. 63/081,428, filed on Sep. 22, 2020, the entire contents of each of which are expressly incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 20, 2021, is named 10714US-01_Sequence_Listing.TXT and is 18,393 bytes in size.

BACKGROUND

Fibrodysplasia ossificans progressiva (FOP), also known as Munchmeyer disease, is an autosomal dominant disorder characterized by early onset, episodic and progressive ossification of skeletal muscle and associated connective tissue. In FOP subjects, bone forms in soft tissue outside of the normal skeleton, a process known as heterotopic ossification (HO), which can lead to the development of a secondary skeleton and progressively restricts the patient's ability to move. Removal of the new bone formation has been shown to be ineffective and leads to the development of additional new bone growth.

FOP is driven by mutations in the intracellular domain of ACVR1 (ALK2), with the great majority altering Arginine 206 to Histidine (R206H) (Pignolo, R. J. et al. 2011, *Orphanet J. Rare Dis.* 6:80). ACVR1 is a type I receptor for bone morphogenic proteins (BMPs). The R206H mutation, among others, is believed to increase the sensitivity of the receptor to activation and render it more resistant to silencing.

Although certain types of drugs have been used to relieve pain and swelling associated with FOP during flare-ups, no effective medical treatment is currently known for FOP.

SUMMARY

The instant disclosure provides a method of treating Fibrodysplasia Ossificans Progressiva (FOP), comprising administering to a subject having FOP a therapeutically effective amount of an activin A antagonist. In particular, the inventors of the instant application have surprisingly discovered, only after undertaking a phase II clinical trial in humans, that treatment of FOP subjects with an activin A antagonist dramatically reduces and/or prevents the development of new heterotopic ossification (HO) bone growth, and reduced average rates of lesion growth and mineralization.

In one aspect the disclosure provides a method of treating fibrodysplasia ossificans progressiva (FOP), the method comprising administering to a human subject having FOP a therapeutically effective amount of an activin A antagonist, thereby treating the FOP.

In some embodiments the activin A antagonist is an anti-activin A antibody or antigen-binding fragment thereof. In some embodiments, the antibody competes for binding with an antibody comprising the heavy and light chain variable regions of the antibody designated H4H10446P, H4H10430P or A1. In some embodiments, the antibody comprises the heavy and light chain variable regions of the antibody designated H4H10446P, H4H10430P or A1. In some embodiments, the antibody is a chimeric, veneered, humanized or human antibody. In some embodiments, the antibody is an intact antibody. In some embodiments, the antibody is a human kappa IgG1 antibody. In some embodiments, the antibody is administered in combination therapy with an ACVR1, ACVR2A, or ACVR2B extracellular domain-Fc fusion protein.

The disclosure further provides an antagonist of activin A for use in a method of treating Fibrodysplasia Ossificans Progressiva (FOP), the method comprising administering to a subject having FOP a therapeutically effective amount of the antagonist of activin A. Optionally, the activin A antagonist is an anti-activin A antibody or antigen-binding fragment thereof. Optionally, the disclosure provides the use of an anti-activin A antibody or antigen-binding fragment thereof in the manufacture of a medicament for treating FOP. Optionally, the antibody is chimeric, veneered, humanized or human antibody. Optionally, the antibody is an intact antibody. Optionally, the antibody is a human kappa IgG1 antibody. Optionally, the antibody is administered in combination therapy with an ACVR1, ACVR2A, or ACVR2B extracellular domain-Fc fusion protein.

In one aspect, the disclosure provides a method of decreasing the formation of new heterotopic ossification lesions in a human subject with FOP, the method comprising administering to the human subject a therapeutically effective amount of an activin A antagonist, thereby decreasing the formation of new heterotopic ossification lesions in the human subject.

In one embodiment, the formation of new heterotopic ossification lesions is prevented in the human subject.

In one embodiment, the human subject exhibits a decrease in number of new heterotopic ossification lesions of at least 5%, at least 10%, at least 20%, at least 30%, at least 40%, at least 50%, at least 60%, at least 70%, at least 80%, at least 90%, at least 5%-90%, at least 10%-90%, at least 20%-90%, at least 30%-90%, at least 40%-90%, at least 50%-90%, at least 60%-90%, at least 70%-90%, at least 80%-90%, at least 5%-80%, at least 5%-70%, at least 5%-60%, at least 5%-50%, at least 5%-40%, at least 5%-30%, at least 5%-20%, or at least 5%-10%, relative to a control.

In one embodiment, the human subject exhibits a decrease in new heterotopic ossification lesion volume by at least 5%, at least 10%, at least 15%, at least 20%, at least 25%, at least 30%, at least 40%, at least 50%, at least 5%-50%, at least 10%-50%, at least 20%-50%, at least 30%-50%, at least 40%-50%, at least 5%-40%, at least 5%-30%, at least 5%-20%, or at least 5%-10%, relative to a control.

In one embodiment, the human subject exhibits a decrease in a rate of new heterotopic ossification lesion growth and mineralization of at least 5%, at least 10%, at least 20%, at least 30%, at least 40%, at least 50%, at least 5%-50%, at least 10%-50%, at least 20%-50%, at least 30%-50%, at least 40%-50%, at least 5%-40%, at least 5%-30%, at least 5%-20%, or at least 5%-10%, relative to a control.

In one embodiment, the human subject exhibits a decrease in new heterotopic ossification lesion intensity of at least 5%, at least 10%, at least 20%, at least 30%, at least 40%, at least 50% at least 5%-50%, at least 10%-50%, at least 20%-50%, at least 30%-50%, at least 40%-50%, at least 5%-40%, at least 5%-30%, at least 5%-20%, or at least 5%-10%, relative to a control.

In one embodiment, the human subject exhibits a decrease in total lesion activity (TLA) of the heterotopic ossification lesions of at least 5%, at least 10%, at least 15%, at least 20%, at least 25%, at least 30%, at least 40%, at least 50%, at least 60%, at least 70%, at least 80%, at least 5%-80%, at least 10%-80%, at least 20%-80%, at least 30%-80%, at least 40%-80%, at least 50%-80%, at least 60%-80%, at least 70%-80%, at least 5%-70%, at least 5%-60%, at least 5%-50%, at least 5%-40%, at least 5%-30%, at least 5%-20%, or at least 5%-10%, relative to a control.

In one embodiment, the human subject exhibits a decrease in daily average pain-NRS of about 0.2-fold, 0.5-fold, 1-fold, 1.5-fold, 2-fold, 3-fold, 0.2 to 3-fold, 0.5 to 3-fold, 1 to 3-fold, 1.5 to 3-fold, 2 to 3-fold, 2.5 to 3-fold, 0.2 to 2.5-fold, 0.2 to 2-fold, 0.2 to 1.5-fold, 0.2 to 1-fold, or 0.2 to 0.5-fold, relative to a control.

In one embodiment, the control is an average measurement or value gathered from a population of human subjects having FOP who have not been administered the activin A antagonist.

In one embodiment, the therapeutically effective amount of an activin A antagonist reduces the occurrence of painful flare-ups in the human subject, relative to a control.

In one embodiment, the new heterotopic ossification lesions are analyzed by a Positron emission tomography (PET) scan, a computed tomography (CT) scan, or a combination thereof. In one embodiment, the PET scan analysis is performed by administration of radiolabeled $^{18}$F sodium fluoride ($^{18}$F-NaF) to the human subject.

In one embodiment, the therapeutically effective amount of an activin A antagonist is administered to the human subject for at least 8 weeks.

In one embodiment, the method further comprises selecting a subject having FOP who would benefit from decreasing formation of new heterotopic ossification lesions. In one embodiment, the subject who would benefit from decreasing formation of new heterotopic ossification lesions is about to undergo surgery.

In one embodiment, the human subject is about to undergo therapeutic treatment for FOP.

In one embodiment, the activin A antagonist does not decrease the number, volume, or size of any pre-existing lesions in the human subject.

In one embodiment, the activin A antagonist is a protein or a small molecule.

In one embodiment, the activin A antagonist is an anti-activin A antibody, or antigen-binding fragment thereof. In one embodiment, the anti-activin A antibody, or antigen-binding fragment thereof, is a chimeric, veneered, humanized or human antibody, or antigen-binding fragment thereof.

In one embodiment, the anti-activin A antibody, or antigen-binding fragment thereof, is a human kappa IgG1 antibody.

In one embodiment, the anti-activin A antibody, or antigen-binding fragment thereof, comprises the following six CDR sequences: (a) an HCDR1 having at least about 80% identity to the sequence GGSFSSHF (SEQ ID NO: 2); (b) an HCDR2 having at least about 80% identity to the sequence ILYTGGT (SEQ ID NO: 3); (c) an HCDR3 having at least about 80% identity to the sequence ARARSGITFTGIIVPGSFDI (SEQ ID NO: 4); (d) an LCDR1 having at least about 80% identity to the sequence QSVSSSY (SEQ ID NO: 6); (e) an LCDR2 having at least about 80% identity to the sequence GAS (SEQ ID NO: 7); and (f) an LCDR3 having at least about 80% identity to the sequence QQYGSSPWT (SEQ ID NO: 8).

In one embodiment, the anti-activin A antibody, or antigen-binding fragment thereof, comprises the following six CDR sequences: (a) an HCDR1 having the sequence GGSFSSHF (SEQ ID NO: 2); (b) an HCDR2 having the sequence ILYTGGT (SEQ ID NO: 3); (c) an HCDR3 having the sequence ARARSGITFTGIIVPGSFDI (SEQ ID NO: 4); (d) an LCDR1 having the sequence QSVSSSY (SEQ ID NO: 6); (e) an LCDR2 having the sequence GAS (SEQ ID NO: 7); and (f) an LCDR3 having the sequence QQYGSSPWT (SEQ ID NO: 8).

In one embodiment, the anti-activin A antibody, or antigen-binding fragment thereof, comprises a heavy chain variable region having at least 90% identity with SEQ ID NO:1 and a light chain variable region having at least 90% identity with SEQ ID NO:5.

In one embodiment, the anti-activin A antibody, or antigen-binding fragment thereof, comprises a heavy chain variable region having at least 95% identity with SEQ ID NO:1 and a light chain variable region having at least 95% identity with SEQ ID NO:5.

In one embodiment, the anti-activin A antibody, or antigen-binding fragment thereof, comprises a heavy chain variable region comprising SEQ ID NO:1 and a light chain variable region comprising SEQ ID NO:5.

In one embodiment, the anti-activin A antibody, or antigen-binding fragment thereof, comprises a heavy chain comprising SEQ ID NO:25 and a light chain comprising SEQ ID NO:26.

In one embodiment, the anti-activin A antibody, or antigen-binding fragment thereof, comprises a heavy chain variable region having at least 90% identity with SEQ ID NO:1 and a light chain variable region having at least 90% identity with SEQ ID NO:5.

In one embodiment, the anti-activin A antibody, or antigen-binding fragment thereof, competes for binding with an antibody comprising the following six CDR sequences: (a) an HCDR1 having the sequence GGSFSSHF (SEQ ID NO: 2); (b) an HCDR2 having the sequence ILYTGGT (SEQ ID NO: 3); (c) an HCDR3 having the sequence ARARSGITFTGIIVPGSFDI (SEQ ID NO: 4); (d) an LCDR1 having the sequence QSVSSSY (SEQ ID NO: 6); (e) an LCDR2 having the sequence GAS (SEQ ID NO: 7); and (f) an LCDR3 having the sequence QQYGSSPWT (SEQ ID NO: 8).

In one embodiment, the activin A antagonist is administered in combination with a second therapy.

In another aspect, the disclosure provides a method of preventing formation of new heterotopic ossification lesions in a human subject with FOP, the method comprising administering to the human subject a therapeutically effective amount of an activin A antagonist, thereby preventing the formation of new heterotopic ossification lesions in the human subject.

In one embodiment, the human subject exhibits a decrease in number of new heterotopic ossification lesions of at least 5%, at least 10%, at least 20%, at least 30%, at least 40%, at least 50%, at least 60%, at least 70%, at least 80%, at least 90%, at least 5%-90%, at least 10%-90%, at least 20%-90%, at least 30%-90%, at least 40%-90%, at least 50%-90%, at least 60%-90%, at least 70%-90%, at least 80%-90%, at least 5%-80%, at least 5%-70%, at least 5%-60%, at least 5%-50%, at least 5%-40%, at least 5%-30%, at least 5%-20%, or at least 5%-10%, relative to a control.

In one embodiment, the human subject exhibits a decrease in new heterotopic ossification lesion volume by at least 5%, at least 10%, at least 15%, at least 20%, at least 25%, at least 30%, at least 40%, at least 50%, at least 5%-50%, at least 10%-50%, at least 20%-50%, at least 30%-50%, at least 40%-50%, at least 5%-40%, at least 5%-30%, at least 5%-20%, or at least 5%-10%, relative to a control.

In one embodiment, the human subject exhibits a decrease in a rate of new heterotopic ossification lesion growth and mineralization of at least 5%, at least 10%, at least 20%, at least 30%, at least 40%, at least 50%, at least 5%-50%, at least 10%-50%, at least 20%-50%, at least 30%-50%, at least 40%-50%, at least 5%-40%, at least 5%-30%, at least 5%-20%, or at least 5%-10%, relative to a control.

In one embodiment, the human subject exhibits a decrease in new heterotopic ossification lesion intensity of at least 5%, at least 10%, at least 20%, at least 30%, at least 40%, at least 50% at least 5%-50%, at least 10%-50%, at least 20%-50%, at least 30%-50%, at least 40%-50%, at least 5%-40%, at least 5%-30%, at least 5%-20%, or at least 5%-10%, relative to a control.

In one embodiment, the human subject exhibits a decrease in total lesion activity (TLA) of the heterotopic ossification lesions of at least 5%, at least 10%, at least 15%, at least 20%, at least 25%, at least 30%, at least 40%, at least 50%, at least 60%, at least 70%, at least 80%, at least 5%-80%, at least 10%-80%, at least 20%-80%, at least 30%-80%, at least 40%-80%, at least 50%-80%, at least 60%-80%, at least 70%-80%, at least 5%-70%, at least 5%-60%, at least 5%-50%, at least 5%-40%, at least 5%-30%, at least 5%-20%, or at least 5%-10%, relative to a control.

In one embodiment, the human subject exhibits a decrease in daily average pain-NRS of about 0.2-fold, 0.5-fold, 1-fold, 1.5-fold, 2-fold, 3-fold, 0.2 to 3-fold, 0.5 to 3-fold, 1 to 3-fold, 1.5 to 3-fold, 2 to 3-fold, 2.5 to 3-fold, 0.2 to 2.5-fold, 0.2 to 2-fold, 0.2 to 1.5-fold, 0.2 to 1-fold, or 0.2 to 0.5-fold, relative to a control.

In one embodiment, the control is an average measurement or value gathered from a population of human subjects having FOP who have not been administered the activin A antagonist.

In one embodiment, the therapeutically effective amount of an activin A antagonist reduces the occurrence of painful flare-ups in the human subject, relative to a control.

In one embodiment, the new heterotopic ossification lesions are analyzed by a Positron emission tomography (PET) scan, a computed tomography (CT) scan, or a combination thereof. In one embodiment, the PET scan analysis is performed by administration of radiolabeled $^{18}$F sodium fluoride ($^{18}$F-NaF) to the human subject.

In one embodiment, the therapeutically effective amount of an activin A antagonist is administered to the human subject for at least 8 weeks.

In one embodiment, the method further comprises selecting a subject having FOP who would benefit from decreasing formation of new heterotopic ossification lesions. In one embodiment, the subject who would benefit from decreasing formation of new heterotopic ossification lesions is about to undergo surgery.

In one embodiment, the human subject is about to undergo therapeutic treatment for FOP.

In one embodiment, the activin A antagonist does not decrease the number, volume, or size of any pre-existing lesions in the human subject.

In one embodiment, the activin A antagonist is a protein or a small molecule.

In one embodiment, the activin A antagonist is an anti-activin A antibody, or antigen-binding fragment thereof. In one embodiment, the anti-activin A antibody, or antigen-binding fragment thereof, is a chimeric, veneered, humanized or human antibody, or antigen-binding fragment thereof.

In one embodiment, the anti-activin A antibody, or antigen-binding fragment thereof, is a human kappa IgG1 antibody.

In one embodiment, the anti-activin A antibody, or antigen-binding fragment thereof, comprises the following six CDR sequences: (a) an HCDR1 having at least about 80% identity to the sequence GGSFSSHF (SEQ ID NO: 2); (b) an HCDR2 having at least about 80% identity to the sequence ILYTGGT (SEQ ID NO: 3); (c) an HCDR3 having at least about 80% identity to the sequence ARARSGITFTGIIVPGSFDI (SEQ ID NO: 4); (d) an LCDR1 having at least about 80% identity to the sequence QSVSSSY (SEQ ID NO: 6); (e) an LCDR2 having at least about 80% identity to the sequence GAS (SEQ ID NO: 7); and (f) an LCDR3 having at least about 80% identity to the sequence QQYGSSPWT (SEQ ID NO: 8).

In one embodiment, the anti-activin A antibody, or antigen-binding fragment thereof, comprises the following six CDR sequences: (a) an HCDR1 having the sequence GGSFSSHF (SEQ ID NO: 2); (b) an HCDR2 having the sequence ILYTGGT (SEQ ID NO: 3); (c) an HCDR3 having the sequence ARARSGITFTGIIVPGSFDI (SEQ ID NO: 4); (d) an LCDR1 having the sequence QSVSSSY (SEQ ID NO: 6); (e) an LCDR2 having the sequence GAS (SEQ ID NO: 7); and (f) an LCDR3 having the sequence QQYGSSPWT (SEQ ID NO: 8).

In one embodiment, the anti-activin A antibody, or antigen-binding fragment thereof, comprises a heavy chain variable region having at least 90% identity with SEQ ID NO:1 and a light chain variable region having at least 90% identity with SEQ ID NO:5.

In one embodiment, the anti-activin A antibody, or antigen-binding fragment thereof, comprises a heavy chain variable region having at least 95% identity with SEQ ID NO:1 and a light chain variable region having at least 95% identity with SEQ ID NO:5.

In one embodiment, the anti-activin A antibody, or antigen-binding fragment thereof, comprises a heavy chain variable region comprising SEQ ID NO:1 and a light chain variable region comprising SEQ ID NO:5.

In one embodiment, the anti-activin A antibody, or antigen-binding fragment thereof, comprises a heavy chain comprising SEQ ID NO:25 and a light chain comprising SEQ ID NO:26.

In one embodiment, the anti-activin A antibody, or antigen-binding fragment thereof, comprises a heavy chain variable region having at least 90% identity with SEQ ID NO:1 and a light chain variable region having at least 90% identity with SEQ ID NO:5.

In one embodiment, the anti-activin A antibody, or antigen-binding fragment thereof, competes for binding with an antibody comprising the following six CDR sequences: (a) an HCDR1 having the sequence GGSFSSHF (SEQ ID NO: 2); (b) an HCDR2 having the sequence ILYTGGT (SEQ ID NO: 3); (c) an HCDR3 having the sequence ARARSGITFTGIIVPGSFDI (SEQ ID NO: 4); (d) an LCDR1 having the sequence QSVSSSY (SEQ ID NO: 6); (e) an LCDR2 having the sequence GAS (SEQ ID NO: 7); and (f) an LCDR3 having the sequence QQYGSSPWT (SEQ ID NO: 8).

In one embodiment, the activin A antagonist is administered in combination with a second therapy.

BRIEF DESCRIPTION OF THE DRAWINGS

FIG. 10 shows the heavy and light chain amino acid sequences (SEQ ID NOs: 25 and 26, respectively) of an exemplary anti-activin A monoclonal antibody.

DEFINITIONS

Figure 1:
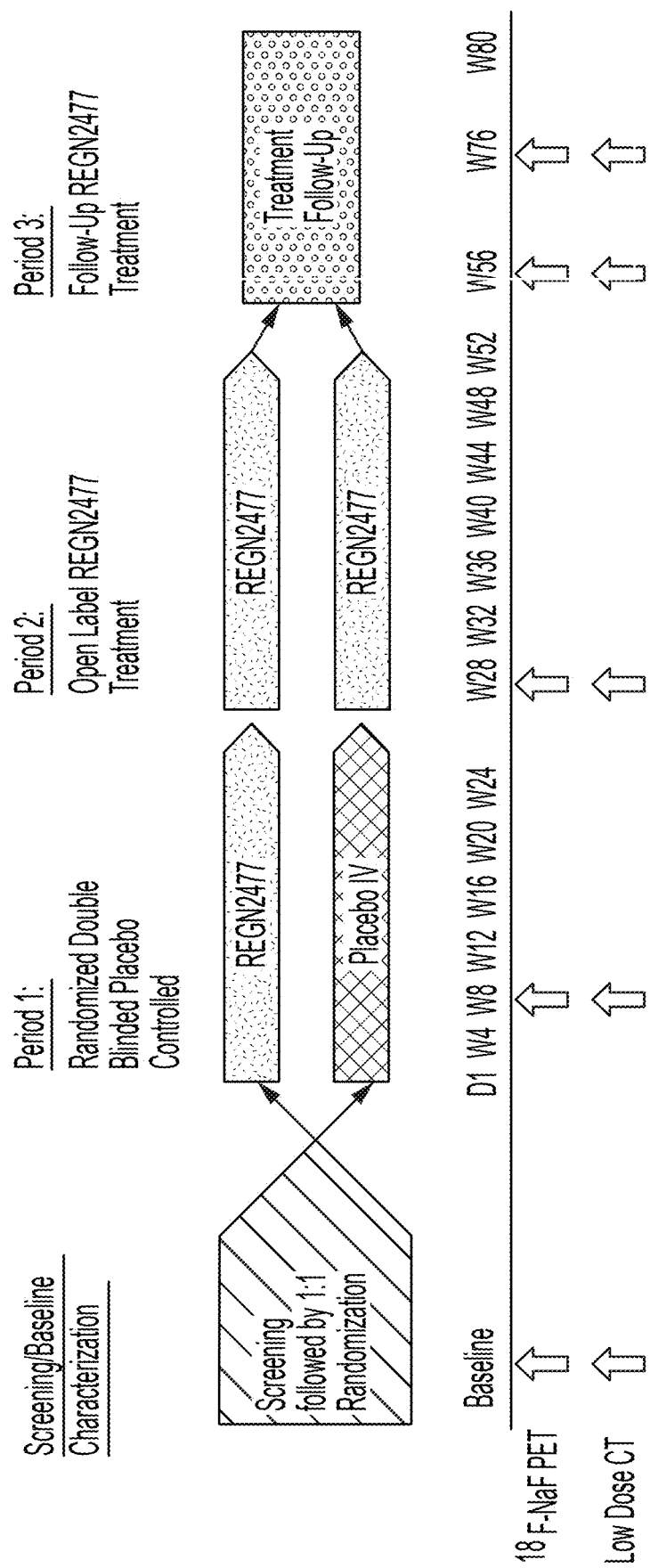
FIG. 1 shows a schematic of a double-blind study for assessing the impact of an anti-activin A antagonist in total lesion activity and volume of heterotopic bone.

Antagonists are typically provided in isolated form. This means that an antagonist is typically at least 50% w/w pure of interfering proteins and other contaminants arising from its production or purification, but does not exclude the possibility that the antagonist is combined with an excess of pharmaceutical acceptable carrier(s) or other vehicle intended to facilitate its use. Sometimes antagonists are at least 60, 70, 80, 90, 95 or 99% w/w pure of interfering proteins and contaminants from production or purification.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. For other proteins, sequence identity can be determined by aligning sequences using algorithms, such as BESTFIT, FASTA, and TFASTA in the Wisconsin Genetics Software Package Release 7.0, Genetics Computer Group, 575 Science Dr., Madison, WI), using default gap parameters, or by inspection, and the best alignment. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements can include other elements not specifically recited. For example, a composition that comprises antibody can contain the antibody alone or in combination with other ingredients.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. Nos. 5,859,205 and 6,881,557; Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly, a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region, respectively, when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al., Journal of Immunology, 164:1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody, but replaces other variable region framework residues that can contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

A human antibody can be isolated from a human, or otherwise result from expression of human immunoglobulin genes (e.g., in a transgenic mouse, in vitro or by phage display). Methods for producing human antibodies include the trioma method of Oestberg et al., *Cys muoma* 2:361-367 (1983); Oestberg, U.S. Pat. No. 4,634,664; and Engleman et al., U.S. Pat. No. 4,634,666. The monoclonal antibodies can also be produced by transgenic mice bearing human immune system genes, such as the VelocImmune® mouse from Regeneron Pharmaceuticals, Inc. (Murphy, PNAS 111 no. 14, 5153-5158 (2014), Xenomouse, Jakobovits, Nature Biotechnology 25, 1134-1143 (2007) or HuMAb mouse from Medarex, Inc. (Lonberg, Handbook Exp. Pharmacol. 181, 69-97 (2008); Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), *Nature Biotechnology* 14, 826 (1996), Kucherlapati, WO 91/10741 (1991). Human antibodies can also be produced by phage display methods (see, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332).

When an antagonist is said to retain a property of a parental antibody from which it was derived, the retention can be complete or partial. Complete retention of an activity means the activity of the antagonist is the same within experimental error or greater than that of the molecule from which it was derived. Partial retention of activity means activity significantly above background level of a negative control (i.e., beyond experimental error) and preferably at least 50% of the corresponding activity of the molecule from which it was derived.

Two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50%, but preferably 75%, 90% or 99%, as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

DETAILED DESCRIPTION

I. Overview

Activin A antibodies have previously been tested in a mouse model of fibrodysplasia ossificans progressiva (FOP) (see, for example, EP3191512B1, filed Sep. 14, 2015, the entire contents of which are expressly incorporated herein by reference). However, the mouse models of FOP, such as the $Acvr1^{[R206H]COIN/+}$; $Gt(ROSA26)Sor^{CreERT2/+}$ mouse model, are all conditional knock-outs, since constitutive mutants were found not to be viable. Therefore, in the FOP mouse models, disease can be "turned on" with tamoxifen, and these currently available mouse models of FOP are not the optimal model for studying human disease, where expression of mutant proteins (for example, $ALK2^{R206H}$) is constitutive.

The instant disclosure is based, in part, on the surprising discovery that treatment of FOP human subjects with an activin A antagonist dramatically reduces and/or prevents the development of new heterotopic ossification (HO) bone growth, and reduced average rates of lesion growth and mineralization. However, treatment with an activin A antagonist surprisingly did not affect already-present bone lesions.

Therefore, disclosed herein are methods for treating fibrodysplasia ossificans progressiva (FOP), also known as Munchmeyer disease, in humans are provided herein. Such methods involve administering to a human subject having FOP a therapeutically effective amount of an activin A antagonist.

II. Activin A

The transforming growth factor β (TGFβ) superfamily of ligands includes, for example, bone morphogenetic proteins (BMPs) and growth and differentiation factors (GDFs). The receptors for these ligands are heteromeric receptor complexes made up of type I and type II transmembrane serine/threonine kinase receptors. Examples of type I receptors include activin receptor type IA (ACTRIA, ACVR1, or ALK2), BMP receptor type IA and BMP receptor type IB. Examples of type II receptors include activin receptors type IIA and IIB (ACTRIIA or ACVR2A and ACTRIIB or ACVR2B) and BMP receptor type II. The ligands of the TGFβ superfamily each have differing affinities for the different type I and type II receptors.

Activin A in humans can exist as a homo- or heterodimeric protein. The homodimeric protein contains a homodimeric beta A subunit pair. The heterodimeric protein contains a beta subunit and a beta B, beta C or beta E subunit (i.e., beta A beta B, beta A beta C, or beta A beta E. The subunits are each expressed as precursor polypeptides including a signal peptide, propeptide and mature polypeptide. An exemplary form of human beta A subunit precursor is a polypeptide of length 426 amino acids designated Swiss Prot P08476 of which residues 1-20 are a signal peptide, residues 21-310 are a propeptide and residues 311-426 are the mature polypeptide. An exemplary form of a beta B subunit precursor polypeptide is designated Swiss Prot P09529 of which residues 1-28 are a signal peptide, residues 29-292 a propeptide and residues 293-407 a mature polypeptide. An exemplary form of a beta C subunit is designated Swiss Prot P55103, of which residues 1-18 are a signal peptide, residues 19-236 are a propeptide and residues 237-352 are a mature polypeptide. An exemplary form of a beta E subunit precursor is designated Swiss Prot P58166 of which residues 1-19 are a signal peptide, residues 20-236 are a propeptide and residues 237-350 are a mature polypeptide. Several variants of these sequences are known as described in the Swiss Prot Data base. Reference to activin A includes any of the beta A homodimer, beta A beta B, beta A beta C and beta A beta E heterodimer forms, as well as their subunits, as well as their precursors in which subunits are attached to the propeptide and/or signal peptide defined by the exemplary Swiss Prot sequences provided or other natural occurring human forms of these sequences. Activin A signals through binding to ACVR2A or ACVR2B, but is not known to be a ligand for ACVR1. Activin A signals aberrantly via mutant ACVR to transduce osteogenic signals and trigger heterotopic bone formation.

Both the type I and type II receptors have an extracellular ligand binding domain (ECD) and an intracellular serine/threonine kinase domain. In addition, the type I receptors have a glycine/serine-rich region (GS-box) preceding the kinase domain and a L45 loop within the kinase domain. Both receptors work together for ligands to activate downstream signaling pathways, such as Smad and non-Smad signaling pathways. Activation involves ligand binding, ligand-receptor oligomerization and transphosphorylation of the GS box of the type I receptor by the type II receptor kinase. The type II receptor kinase is constitutively active and has a role in ligand binding and activation of the type I receptor.

ACVR1, also known as activin a receptor type I, ACVR1A, ACVRLK2, or ALK2, is a type I receptor for the TGFβ superfamily of ligands. ACVR1 has serine/threonine kinase activity and phosphorylates Smad proteins and activates downstream signaling pathways. ACVR1 is found in many tissues of the body including skeletal muscle and cartilage and helps to control the growth and development of the bones and muscles. As described elsewhere herein, certain mutations in the ACVR1 gene cause FOP. Examples of ACVR1 activity include the ability to bind to ligands, the ability to form a complex with a type II receptor, or the ability to activate downstream signaling pathways, such as the Smad pathway.

ACVR2, also known as activin receptor type II, is a type II receptor for the TGFβ superfamily of ligands. There are at least two ACVR2 receptors, for example, activin receptor type IIA (ACVR2A or ACTRIIA) and activin receptor type IIB (ACVR2B or ACTRIIB). Reference to ACVR2 includes either or both of ACVR2A and ACVR2B. ACVR2A and ACVR2B can be expressed in multiple tissues, including skeletal muscle, stomach, heart, endometrium, testes, prostate, ovary, and neural tissues.

On ligand binding, an ACVR2 receptor forms a complex with a type I receptor, such as ACVR1, and phosphorylates the GS box of the type I receptor, thus enhancing the kinase activity of the type I receptor. Examples of ACVR2A and ACVR2B activity include the ability to bind to ligands, the ability to form a complex with a type I receptor, or the ability to phosphorylate a type I receptor.

An exemplary form of human ACVR2A has Swiss Prot accession number P27037. Residues 1-19 are a signal peptide, residues 20-135 are an extracellular domain, residues 59-116 are an activin types I and II receptor domain, residues 136-161 are a transmembrane domain and residues 162-513 are a cytoplasmic domain. An exemplary form of human ACVR2B is assigned Swiss Prot Number Q13705. Residues 1-18 are a signal sequence, residues 19-137 are an extracellular domain, residues 27-117 are an activin types I and II receptor domain, residues 138-158 are a transmembrane domain and residues 159-512 are a cytoplasmic domain. An exemplary form of human ACVR1 has Swiss Prot accession number Q04771. Residues 1-20 are a signal sequence, residues 21-123 are extracellular domain, residues 33-104 are an activin types I and II receptor domain, residues 124-146 are a transmembrane domain and residues 147-509 are a cytoplasmic domain. Reference to any of ACVR1, ACVR2A and ACVR2B includes these exemplary forms, known isoforms and polymorphisms thereof, such as those listed in the Swiss Prot database, cognate forms from other species, and other variants having at least 90, 95, 96, 97, 98 or 99% sequence identity with an exemplified form.

Residues of forms of ACVR2A, ACVR2B and ACVR1 other than the exemplified sequences defined above are numbered by maximum alignment with the corresponding exemplified sequences so aligned residues are allocated the same number. Substitutions from exemplified sequences can be conservative or non-conservative substitutions. Reference to ACVR1, ACVR2A or ACVR2B also includes intact extracellular domains (e.g., residues 20-135, 19-137 or 21-123 of ACVR2A, ACVR2B and ACVR1, respectively) or a portion thereof free or substantially free of transmembrane and cytoplasmic portion. Portions of an extracellular domain retain sufficient residues of the intact extracellular domain to bind at least one ligand or counter receptor that binds to the intact extracellular domain and thereby antagonize the relevant receptor (e.g., residues 59-116, 27-117 or 33-104 of ACVR2A, ACVR2B and ACVR1, respectively).

III. Antagonists of Activin A

A. Antibodies

The term "antibody" covers intact antibodies with two pairs of heavy and light chains, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

"Antibody fragments" comprise a portion of an intact antibody, preferably the antigen-binding or variable region of the intact antibody. Examples of antibody fragments include Fab, F(ab')$_2$, and Fv fragments; diabodies; linear antibodies (Zapata et al. (1995) *Protein Eng.* 10:1057-1062); single-chain antibody molecules; and multispecific antibodies formed from antibody fragments.

The antibody can be monoclonal or polyclonal. A "monoclonal antibody" is an antibody obtained from a population of substantially homogeneous antibodies, that is, the individual antibodies comprising the population are identical except for possible naturally occurring mutations that can be present in minor amounts. Monoclonal antibodies are often highly specific, being directed against a single antigenic site. Furthermore, in contrast to conventional (polyclonal) antibody preparations that typically include different antibodies directed against different determinants (epitopes), each monoclonal antibody is typically directed against a single determinant on the antigen. The modifier "monoclonal" indicates the character of the antibody as being obtained from a substantially homogeneous population of antibodies, such as those produced by a clonal population of B-cells, and does not require production of the antibody by any particular method.

Monoclonal antibodies to be used in accordance with the methods provided herein can be made by the hybridoma method first described by Kohler et al. (1975) *Nature* 256:495, or a modification thereof. Typically, an animal, such as a mouse, is immunized with a solution containing an antigen (e.g., an activin A, ACVR1, ACVR2A and/or ACVR2B polypeptide, or particularly the extracellular domain (in receptors) or a portion thereof).

Immunization can be performed by mixing or emulsifying the antigen-containing solution in saline, preferably in an adjuvant such as Freund's complete adjuvant, and injecting the mixture or emulsion parenterally. After immunization of the animal, the spleen (and optionally, several large lymph nodes) are removed and dissociated into single cells. The spleen cells can be screened by applying a cell suspension to a plate or well coated with the antigen of interest. The B-cells expressing membrane bound immunoglobulin specific for the antigen bind to the plate and are not rinsed away. Resulting B-cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

Alternatively, the monoclonal antibodies can be made by recombinant DNA methods (see, e.g., U.S. Pat. No. 4,816, 567). The monoclonal antibodies can also be isolated from phage antibody libraries using the techniques described in, for example, Clackson et al. (1991) *Nature* 352:624-628; Marks et al. (1991) *J. Mol. Biol.* 222:581-597; and U.S. Pat. No. 5,514,548.

"Antibodies" include chimeric, veneered, humanized and human monoclonal antibodies against any of activin A, ACVR1, ACVR2A, ACVR2B and as defined above.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The present monoclonal antibodies or Fc fusion proteins can be any of the various antibody classes. In one embodiment, the monoclonal antibody is an IgG class antibody. In other embodiments, the monoclonal antibody can be of the IgM, IgE, IgD, or IgA class. In specific embodiments, the antibody is an isotype of IgG, such as, IgG1, IgG2, IgG3 or IgG4, particularly human IgG1, IgG2, IgG3 or IgG4.

One or several amino acids at the amino or carboxy terminus of the light and/or heavy chain, such as a C-terminal lysine of the heavy chain, can be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering) for increasing the half-life of an antibody. Substitution at any of positions 234, 235, 236 and/or 237 reduces affinity for Fcγ receptors, particularly FcγRI receptor (see, e.g., U.S. Pat. No. 6,624,821). Optionally, positions 234, 236 and/or 237 in human IgG2 are substituted with alanine and position 235 with glutamine. (See, e.g., U.S. Pat. No. 5,624,821). Effector functions can also be reduced by substitution of EFLG at positions 232-236 with PVA (see WO14/121087). Optionally, S at position 428 can be replaced by P, particularly in human IgG4 to reduce exchange between endogenous and exogenous immunoglobulins. Other variations can add or remove sites of post-translational modification, such as N-linked glycosylation at N—X—S/T motifs. Variations can also include introduction of knobs (i.e., replacement of one or more amino acids with larger amino acids) or holes (i.e., replacement of one or more amino acids with smaller amino acids) to promote formation of heterodimers between different heavy chains for production of bispecific antibodies. Exemplary substitutions to form a knob and hole pair are T336Y and Y407T, respectively (Ridgeway et al., Protein Engineering vol. 9 no. 7 pp. 617-621, 1996). Variations can also include mutations that reduce protein A interaction (e.g., H435R and Y436F) in the EU numbering system. Bispecific antibodies in which one heavy chain has such a variation, and another does not, can be separated from their parental antibodies by protein-A affinity chromatography.

Antibodies can also include antibodies specifically binding to activin A. Such antibodies can specifically bind to any or all of the beta A beta A, beta A beta B, beta A beta C and beta A beta E forms of activin A. Some antibodies specifically bind to only one of these forms (i.e., beta A beta A, beta A beta B, beta A beta C or beta A beta E). Specificity for the beta A beta B, beta A beta C and beta A beta E forms can be conferred by an epitope within the beta B, beta C or beta E subunit, respectively, or for an epitope to which both components of the heterodimer contribute. Specificity for beta A beta can be conferred by an epitope contributed by both molecules within the homodimer (e.g., at the interface of subunits). Some antibodies specifically bind to all of these forms of activin A, in which case the epitope is typically on the beta A subunit. Antibodies typically have epitopes within the mature polypeptide component of the precursor proteins. Some antibodies specifically bind to any or all forms of activin A without binding to human inhibin, which exists in the form of alpha (Swiss Prot P05111) beta A or alpha beta B heterodimers. Some antibodies specifically bind to any or all forms of activin A and bind to either or both forms of human inhibin. Although it is believed that such antibodies inhibit signal transduction of activin A through one or more of its counterreceptors, ACVR2A and/or ACVR2B and/or BMPR2, an understanding of mechanism is not required for use of such antibodies in methods of treating FOP.

A substantial number of antibodies against activin A have been reported. For example, U.S. Pat. No. 9,718,881 discloses human antibodies designated H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10447P2, H4H10448P2, H4H10452P2. U.S. Pat. No. 8,309,082 discloses human antibodies A1-A14. Mouse antibodies against activin A are available from several commercial suppliers, such as MAB3381 from R&D Systems or 9H16 from Novus Biologicals or MM0074-7L18 (ab89307) AbCam.

Preferred antibodies have an affinity for activin A (measured at 25° C. as in Example 3 of US2015/00373339) of at least $10^8$ M$^{-1}$, $10^9$ M$^{-1}$, $10^{10}$ M$^{-1}$, $10^{11}$ M$^{-1}$, $10^{12}$ M$^{-1}$, or $10^{13}$ M$^{-1}$. Some antibodies have an affinity within a range of $10^9$-$10^{12}$ M$^{-1}$. Preferred antibodies inhibit signal transduction of activin A with an IC50 of less than 4 nM, and preferably less than 400 pM or 40 pM. Some antibodies inhibit signal transduction with and IC50 in a range of 4 nM to 10 pM or 3.5 nM to 35 pM.

Signal transduction inhibition can be measured as in Example 6 of U.S. Pat. No. 9,718,881, which is summarized as follows. A human A204 rhabdomyosarcoma cell line is transfected with a Smad 2/3-luciferase reporter plasmid to produce the A204/CAGAx12-Luc cell line. A204/CAGAx12-Luc cells were maintained in McCoy's 5A supplemented with 10% fetal bovine serum, penicillin/streptomycin/glutamine and 250 µg/mL of G418. For the bioassay, A204/CAGAx12-Luc cells were seeded onto 96-well assay plates at 10,000 cells/well in low serum media, 0.5% FBS and OPTIMEM, and incubated at 37° C. and 5% $CO_2$ overnight. Activin A is serially diluted at 1:3 from 100 to 0.002 nM and added to cells starting along with a control containing no activin. Antibodies are serially diluted at 1:3 starting from 100 to 0.002 nM, 1000 to 0.02 nM, or 300 to 0.005 nM including control samples containing either an appropriate isotype control antibody or no antibody and added to cells with a constant concentration of 100 pM activin A.

Some antibodies inhibit binding of activin A to ACVR2A and/or ACVR2B and/or BMPR2 by at least 1%, 5%, 10%, 20%, 30%, 40%, 50%, 60%, 70%, 80%, 90%, 95%, 99%, as measured when the receptor is expressed from a cell or the extracellular domain is fused with an Fc domain as a fusion protein, and the fusion protein is immobilized to support (e.g., a Biacore sensor chip). In such measurements, the antibody and activin A should be present in equimolar amounts and the receptor or extracellular domain in excess.

Some antibodies bind to an epitope within residues 321-343 or 391-421 of full-length activin A, which correspond to C11-S33 and C81-E111 of the mature protein.

An exemplary antibody used in the present examples is designated H4H10446P in U.S. Pat. No. 9,718,881. Its heavy chain variable region and heavy chain CDR1, CDR2 and CDR3 having the amino acid sequences of SEQ ID NOs:162, 164, 166 and 168, respectively, of U.S. Pat. No. 9,718,881 (present SEQ ID NOs: 1, 2, 3 and 4, respectively). Its light chain variable region and light chain CDRs, CDRL1, CDRL2 and CDRL3 having the amino acid sequences of SEQ ID NO:146, 148, 150 and 152, respectively, of U.S. Pat. No. 9,718,881 (present SEQ ID NOs: 5, 6, 7 and 8, respectively). H4H10446P inhibits activin A mediated signaling through ACVR2A and/or ACVRIIB, but does not inhibit strongly, if at all, activin A binding to ACRIIA or ACVR2B. Other antibodies competing with H4H10446P for binding to human activin A or binding to the same epitope on human activin A as H4H10446P are included and sharing its inhibition of signaling are also included.

Another exemplary antibody for use in the present methods is designated H4H10430P in U.S. Pat. No. 9,718,881. Its heavy chain variable region and heavy chain CDRs CDRH1, CDRH2 and CDRH3 having the amino acid sequences of SEQ ID NOs:66, 68, 70 and 72, respectively, in U.S. Pat. No. 9,718,881 (present SEQ ID NOs: 9, 10, 11 and 12, respectively). Its light chain variable region and light chain CDRs, CDRL1, CDRL2 and CDRL3 having the amino acid sequences of SEQ ID NOs:74, 76, 78 and 80, respectively, in U.S. Pat. No. 9,718,881 (present SEQ ID NOs: 13, 14, 15 and 16, respectively). This antibody inhibits binding of activin A to ACRV2A and/or ACVR2B and inhibits signal transduction through one or both of these receptors. Other antibodies competing with H4H10430P for binding to activin A or binding to the same epitope on activin A as H4H10430P and sharing its property of inhibiting activin A binding to and signal transduction through ACVR2A and ACVR2B are also included.

An exemplary antibody for use in the present methods is garetosmab. The recombinant monoclonal antibody garetosmab is a covalent heterotetramer consisting of two disulfide-linked human heavy chains (IgG4 isotype), each covalently linked through a disulfide bond to a human kappa light chain. Based on the primary sequence, the antibody without glycans possesses a predicted molecular weight of 145,235.3 Da, assuming the formation of 16 canonical disulfide bonds and removal of Lys453 from each heavy chain C-terminus. Each heavy chain contains a serine-to-proline mutation at amino acid Pro234 within the hinge region of the Fc domain, to reduce the propensity of the IgG4 isotype antibody to form half-antibodies in solution. There is a single N-linked glycosylation site (Asn303) on each heavy chain, located within the constant region in the Fc domain of the molecule. The complementarity-determining regions (CDRs) within the garetosmab heavy chain and light chain variable domains together form the binding site for its targets: activin A, activin AB, and activin AC. The heavy and light chain amino acid sequences, the location of the CDRs within each polypeptide chain, the location of the heavy chain N-linked glycosylation site, and the predicted disulfide bond structures of the garetosmab monoclonal antibody are presented in FIG. 10.

Another exemplary antibody for use in the present methods is the antibodies designated A1 in U.S. Pat. No. 8,309,082, which is characterized by light and heavy chain variable regions having the sequences SEQ ID NOs: 9 and 10 in U.S. Pat. No. 8,309,082 (present SEQ ID NOs: 17 and 18, respectively). Its light chain CDRs, CDRL1, CDRL2 and CDRL3 having the sequences SEQ ID NO:11, 12, and 13, respectively, in U.S. Pat. No. 8,309,082 (present SEQ ID NOs:19, 20 and 21, respectively), and its heavy chain CDRs, CDRH1, CDRH2 and CDRH3 having the sequences SEQ ID NOs: 62, 63 and 64, respectively, in U.S. Pat. No. 8,309,082 (present SEQ ID NOs:22, 23 and 24, respectively). Other antibodies competing with H4H10430P for binding to activin A or binding to the same epitope on activin A as H4H10430P and sharing its property of inhibiting activin A binding to and transducing a signal through ACVR2A and/or ACVR2B are also included.

Other antibodies can be obtained by mutagenesis of cDNA encoding the heavy and light chains of any of the above-mentioned antibodies. Monoclonal antibodies that are at least 90%, 95% or 99% identical to any of the above-mentioned antibodies in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the disclosure. Monoclonal antibodies having at least 1, 2, 3, 4, 5 and preferably all six CDR(s) that are 90%, 95%, 99% or 100% identical to corresponding CDRs of any of the exemplified antibodies are also included. CDRs are preferably as defined by Kabat, but can be defined by any conventional alternative definition, such as Chothia, composite Kabat-Chothia, the contact definition or AbM definition (see world wide web bioinf.org.uk/abs).

B. Protein/Peptide Inhibitors

Antagonists of activin A useful in the methods of the disclosure include various molecules, for example, peptide inhibitors of activin A, as well as various inhibitory fragments, derivatives, and analogs thereof. Also included within the present disclosure are peptide inhibitors of activin A which can function as competitive inhibitors of activin A signaling, as well as various inhibitory fragments, derivatives, and analogs thereof. In some embodiments, the peptide inhibitor is Follistatin (see, for example, PCT Publication No. WO 2014/064292) or a derivative or an analog thereof, which inhibits a signaling pathway between activin A and any of its receptors disclosed herein. Signal transduction inhibition can be measured as previously disclosed herein.

Peptide inhibitors of activin A can be produced recombinantly from the corresponding fragments of the nucleic acids using various expression systems well known in the art and a variety of host systems are suitable for production, including bacteria (e.g., *E. coli*), yeast (e.g., *Saccharomyces cerevisiae*), insect (e.g., Sf9), and mammalian cells (e.g., CHO, COS-7). Many expression vectors have been developed and are available for each of these hosts. Vectors and procedures for cloning and expression are discussed, for example, in Sambrook et al. (Sambrook et al., Molecular Cloning: A Laboratory Manual, Cold Spring Harbor Laboratory Press, Cold Spring Harbor, N.Y. (1987)) and in Ausubel et al., 1995. Standard expression vectors useful in the current disclosure are well known in the art and include (but are not limited to) plasmids, cosmids, phage vectors, viral vectors, and yeast artificial chromosomes. The vector sequences may contain a replication origin for propagation in *Escherichia coli* (*E. coli*); the SV40 origin of replication; an ampicillin, neomycin, or puromycin resistance gene for selection in host cells; and/or genes (e.g., dihydrofolate reductase gene) that amplify the dominant selectable marker plus the gene of interest.

Alternatively, peptide inhibitors of activin A can be chemically synthesized using techniques known in the art such as, e.g., conventional Merrifield solid phase f-Moc or t-Boc chemistry. For methods of peptide synthesis see also Bodansky, "Principles of Peptide Synthesis," (Springer Verlag, Berlin (1993)) and Grant (ed.), "Synthetic Peptides: A User's Guide," (W. H. Freeman and Company, New York (1992)). In addition, automated peptide synthesizers are commercially available (e.g., Advanced ChemTech Model 396; Milligen/Biosearch 9600).

In certain embodiments, the useful antagonists of activin A are small molecules such as a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., *Acta Crystallogr. Section B* 35:2331 (1979)). Where no crystal structure of a target molecule is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and also can be searched to identify potential peptidomimetics.

In certain embodiments, the peptide inhibitors of activin A may further comprise post-translational modifications. Such modifications include, but are not limited to, acetylation, carboxylation, glycosylation, phosphorylation, lipidation, and acylation. As a result, the modified soluble polypeptides may contain non-amino acid elements, such as polyethylene glycols, lipids, poly- or mono-saccharide, and phosphates. Effects of such non-amino acid elements on the functionality of a polypeptide can be tested using the functional assays described herein.

C. Small Molecule Inhibitors

The present disclosure also encompasses small molecule inhibitors of activin A. Small molecules are a diverse group of synthetic and natural substances generally having low molecular weights (preferably less than about 2000 Daltons, less than about 1000 Daltons, or less than about 500 Daltons). Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting. They can be isolated from natural sources (for example, plants, fungi, microbes and the like) or isolated from random or combinatorial chemical libraries of synthetic or natural compounds, or synthesized. See Werner et al., (2006) Brief Funct. Genomic Proteomic 5(1):32-6. Many random or combinatorial libraries are known in the art that can be used. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) Tib Tech 14:60).

Identification and screening of antagonists of activin A, e.g., small molecule inhibitors, can be further facilitated by determining structural features of the involved proteins, e.g., using X-ray crystallography, neutron diffraction, nuclear magnetic resonance spectrometry, and other techniques for structure determination. These techniques provide for the rational design or identification of antagonists of activin A.

D. Compounds Affecting Activin a Expression or the Downstream Molecular Events in Activin a Signaling The present disclosure also encompasses inhibitors of activin A which inhibit activin A expression, or prevent activin A from engaging with its downstream signaling pathway(s). Non-limiting examples of useful expression inhibitors include, e.g., interfering RNA (e.g., siRNA), dsRNA, RNA polymerase III transcribed DNAs, ribozymes, and antisense nucleic acids.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the target DNA sequence can be synthesized, e.g., by conventional phosphodiester techniques (Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59).

siRNA comprises a double stranded structure typically containing 15 to 50 base pairs and preferably 21 to 25 base pairs and having a nucleotide sequence identical or nearly identical to an expressed target gene or RNA within the cell. Antisense polynucleotides include, but are not limited to: morpholinos, 2'-O-methyl polynucleotides, DNA, RNA and the like. Examples of siRNA inhibiting activin A expression include, but are not limited to, anti-activin A siRNA disclosed in Hoda et al., Br J Cancer. 2012 Dec. 4; 107(12): 1978-86.

RNA polymerase III transcribed DNAs contain promoters, such as the U6 promoter. These DNAs can be transcribed to produce small hairpin RNAs in the cell that can function as siRNA or linear RNAs that can function as antisense RNA. The inhibitor may be polymerized in vitro, recombinant RNA, contain chimeric sequences, or derivatives of these groups. The inhibitor may contain ribonucleotides, deoxyribonucleotides, synthetic nucleotides, or any suitable combination such that the target RNA and/or gene is inhibited. In addition, these forms of nucleic acid may be single, double, triple, or quadruple stranded. (see for example Bass (2001) Nature, 411, 428 429; Elbashir et al., (2001) Nature, 411, 494 498; and PCT Publication Nos. WO 00/44895, WO 01/36646, WO 99/32619, WO 00/01846, WO 01/29058, WO 99/07409, WO 00/44914).

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of mRNA sequences are also within the scope of the present disclosure. Scanning the target molecules for ribozyme cleavage sites that include the following sequences, GUA, GUU, and GUC initially identifies specific ribozyme cleavage sites within any potential RNA target. Once identified, short RNA sequences of between about 15 and 20 ribonucleotides corresponding to the region of the target gene containing the cleavage site can be evaluated for predicted structural features such as secondary structure that may render the oligonucleotide sequence unsuitable. The suitability of candidate targets can also be evaluated by testing their accessibility to hybridization with complementary oligonucleotides using, e.g., ribonuclease protection assays.

Expression inhibitors of the present disclosure can be prepared by known methods. These include techniques for chemical synthesis such as, e.g., by solid phase phosphoamite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. See, e.g., Weintraub, H. et al., Antisense RNA as a molecular tool for genetic analysis, Reviews—Trends in Genetics, Vol. 1 (1) 1986.

Various modifications to the oligonucleotides of the present disclosure can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Aptamers nucleic acid sequences are readily made that bind to a wide variety of target molecules. The aptamer nucleic acid sequences of the disclosure can be comprised entirely of RNA or partially of RNA, or entirely or partially of DNA and/or other nucleotide analogs. Aptamers are typically developed to bind particular ligands by employing known in vivo or in vitro (most typically, in vitro) selection techniques known as SELEX (Systematic Evolution of Ligands by Exponential Enrichment). Methods of making aptamers are described in, for example, Ellington and Szostak (1990) Nature 346:818, Tuerk and Gold (1990) Science 249:505, U.S. Pat. No. 5,582,981; PCT Publication No. WO 00/20040; U.S. Pat. No. 5,270,163; Lorsch and Szostak (1994) Biochem. 33:973; Mannironi et al., (1997) Biochem. 36:9726; Blind (1999) Proc. Nat'l. Acad. Sci. USA 96:3606-3610; Huizenga and Szostak (1995) Biochem. 34:656-665; PCT Publication Nos. WO 99/54506, WO 99/27133, and WO 97/42317; and U.S. Pat. No. 5,756,291.

IV. Antagonists of ACVR1, ACVR2A, ACVR2B

Antagonists of the type I receptor ACVR1 and of the type II receptor ACVR2 proteins (e.g., ACVR2A and/or ACVR2B) are provided for treating FOP. Such antagonists can antagonize receptors directly by binding to the receptor (as for an antibody to ACVR1, ACVR2A or ACVR2B) or indirectly by binding to a ligand or counter receptor and inhibiting the ligand or counter receptor from binding to ACVR1, ACVR2A or ACVR2B (as for a fusion protein of ACVR1, ACVR2A or ACVR2B) among other mechanisms. Antagonists of ACVR2A and ACVR2B can also bind to activin A.

An ACVR1, ACVR2A or ACVR2B antagonist provided herein can inhibit or reduce the activity of ACVR1, ACVR2A and/or ACVR2B by at least 1%, 5%, 10%, 20%, 30%, 40%, 50%, 60%, 70%, 80%, 90%, 95%, 99% or more relative to a control cell or animal model that did not receive the antagonist.

Any antagonist of activin A can be used, alone or in combination with antagonists of one or more of ACVR1, ACVR2A or ACVR2B, in the methods for treating FOP. The antagonist can comprise, for example, an activin A, ACVR1, ACVR2A or ACVR2B polypeptide, such as an extracellular domain, an antagonist antibody, or a small molecule inhibitor.

A. Extracellular Domains of ACVR1, ACVR2A and ACVR2B Polypeptides

Antagonists include ACVR1, ACVR2A and ACVR2B proteins and fragments thereof effective to inhibit at least one activity of ACVR1, ACVR2A and ACVR2B, respectively. Such antagonists typically include the extracellular domain of ACVR1, ACVR2A or ACVR2B or a portion thereof. Preferably, such extracellular domains are entirely or substantially free of the transmembrane and cytoplasmic regions (i.e., any remaining residues from these regions have no significant effect on function of the extracellular domain). In other words, the ACVR2A, ACVR2B or ACVR1 component of such antagonists consists of or consists essentially of the entire extracellular domain of ACVR2A, ACVR2B or ACVR1 or a portion thereof as defined above Such antagonists may or may not include other component(s) distinct from ACVR2A, ACVR2B or ACVR1 as further described below. Such extracellular domains free or substantially free of transmembrane and cytoplasmic domains are soluble. Such extracellular domains can function as an antagonist by binding to a soluble ligand or counter receptor, effectively competing with the ligand or counter receptor binding to the ACVR1, ACVR2A or ACVR2B cell surface receptor, thereby modulating (reducing) the availability of the ligand or counter receptor in vivo.

Soluble extracellular domains can be initially expressed with a signal sequence, which is cleaved in the course of expression. The signal sequence can be a native signal sequence of an ACVR1, ACVR2A or ACVR2B, such as those described in U.S. Pat. No. 7,709,605, which is incorporated by reference herein in its entirety, or can be a signal sequence from a different protein such honey bee melittin (HBM) or tissue plasminogen activator (TPA). Alternatively, soluble extracellular ACVR1, ACVR2A or ACVR2B polypeptides can be synthesized or expressed without a signal sequence.

The ECDs or ligand binding domains of ACVR1, ACVR2A and ACVR2B are highly conserved among species including mouse and human. The ECDs contain a cysteine rich region and a C-terminal tail region. The ECDs of ACVR1, ACVR2A and ACVR2B bind to a diverse group of TGFβ family ligands, including, for example, activin A, myostatin (GDF-8), GDF-11 and BMPs. See, e.g., Souza et al. (2008) Molecular Endocrinology 22(12):2689-2702.

Examples of ACVR2A and ACVR2B polypeptides and soluble ACVR2A and ACVR2B polypeptides include those disclosed in U.S. Pat. Nos. 7,842,633; 7,960,343; and 7,709,605, each of which is incorporated by reference herein in their entirety.

The ECD of an ACVR1, ACVR2A or ACVR2B polypeptide can be mutated such that the variant polypeptide has altered ligand binding properties (e.g., binding specificity or affinity). Some variant ACVR1, ACVR2A or ACVR2B polypeptides have altered binding affinity (e.g., elevated or reduced) for a specific ligand. Variants have at least 90%, 91%, 92%, 93%, 94%, 95%, 96%, 97%, 98%, 99% sequence identity to the naturally occurring ACVR1, ACVR2A or ACVR2B sequences, and retain biological activity and hence have an ACVR1, ACVR2A or ACVR2B activity as described elsewhere herein. Active variants and fragments of ACVR2A and ACVR2B are described, for example, in U.S. Pat. Nos. 7,842,633; 7,960,343; and 7,709,605, each of which is incorporated by reference herein in its entirety.

Assays to measure ACVR1, ACVR2A or ACVR2B activity are disclosed in e.g., U.S. Pat. Nos. 7,842,633; 7,960,343; and 7,709,605. For example, an ACVR1, ACVR2A or ACVR2B polypeptide variant can be screened for the ability to bind a ligand or for the ability to prevent binding of a ligand to an ACVR1, ACVR2A or ACVR2B receptor protein.

B. Fusion Proteins

The ACVR1, ACVR2A and ACVR2B polypeptides described above can be expressed as fusion proteins having at least a portion of an ACVR1, ACVR2A and/or ACVR2B polypeptide and one or more fusion domains.

Fusion domains include an immunoglobulin heavy chain constant region (Fc), human serum albumin (HSA), glutathione S transferase (GST), protein A, protein G, or any fusion domain which can be useful in stabilizing, solubilizing, isolating or multimerizing a fusion protein.

An Fc domain of an immunoglobulin heavy chain is a preferred domain for fusion proteins. Fusions with the Fc portion of an immunoglobulin confer desirable pharmacokinetic properties on a wide range of proteins (e.g., increases stability and/or serum half-life of the protein). Thus, the disclosure provides fusion proteins comprising at least one ECD of an ACVR1, ACVR2A and/or ACVR2B fused to an Fc domain of an immunoglobulin.

The Fc domain for use in the present methods can be from any immunoglobulin. Any of the various classes of immunoglobulin can be used, including IgG, IgA, IgM, IgD and IgE. Within the IgG class there are different subclasses or isotypes, including, for example, $IgG_1$, $IgG_2$, $IgG_3$ and $IgG_4$. In one embodiment, the Fc fusion protein comprises the Fc domain of an IgG molecule. In a further embodiment, the Fc domain is from an IgG1 molecule. The immunoglobulin molecule can be of any animal type, including, for example, a mammal, a rodent, a human, a mouse, a rat, a hamster or a rabbit. In one embodiment, the immunoglobulin Fc domain is from a mammal. In another embodiment, the Fc domain is from a human. In yet another embodiment, the Fc domain is from a rodent, such as a mouse or rat. In a specific embodiment, the Fc domain of the fusion protein is from human IgG1.

The Fc-fusion proteins provided herein can be made by any method known in the art. The Fc-fusion proteins can include at least CH2 and CH3 regions, and typically at least a portion of a hinge region. Although the CH1 region can be present, it is typically omitted in fusion proteins.

The fusion can be made at any site within the Fc portion of an immunoglobulin constant domain. Fusions can be made to the C-terminus of the Fc portion of a constant domain, or immediately N-terminal to the CH1 region of the heavy chain. Particular sites can be selected to optimize the biological activity, secretion or binding characteristics of the Fc-fusion protein.

In some cases, a nucleic acid encoding the ECD of ACVR1, ACVR2A and/or ACVR2B is fused C-terminally to a nucleic acid encoding the N-terminus of an immunoglobulin constant domain sequence. In other cases, N-terminal fusions are also possible. It is also possible to fuse an ECD of ACVR1, ACVR2A and/or ACVR2B to both the N-terminus and the C-terminus of an immunoglobulin constant domain sequence.

For the production of immunoglobulin fusions, see also U.S. Pat. Nos. 5,428,130, 5,843,725, 6,018,026 and WO2005/070966, each of which is incorporated by reference herein in their entirety.

A fusion protein can be produced, for example, by recombinant expression of a nucleic acid encoding the fusion protein. For example, the fusion protein can be made by fusing a nucleic acid encoding an ECD of ACVR1, ACVR2A and/or ACVR2B to a nucleic acid encoding an Fc domain. The ACVR1, ACVR2A and/or ACVR2B ECD nucleic acid can be fused to the N-terminus of a nucleic acid encoding an Fc domain or can be fused to the C-terminus of a gene encoding an Fc domain. Alternatively, the ECD can be fused at any position in the Fc domain.

The ECD fusion proteins can also include a linker. In the case of an Fc fusion protein, the linker can be positioned between the ACVR1, ACVR2A or ACVR2B ECD and the Fc domain, optionally replacing part or all of the hinge region. The linker can be 1, 2, 3, 4, 5, 6, 7, 8, 9, 10, 15, 20, 30, 50 or more amino acids that are relatively free of secondary structure. A linker can be rich in glycine and proline residues and can, for example, contain repeating sequences of threonine/serine and glycines (e.g., $TG_4$ (SEQ ID NO: 27) or $SG_4$ (SEQ ID NO: 28) repeats).

Two or more ECD-Fc fusion proteins can be joined together by a linker. In such cases, the linker can be positioned between the ECDs or the linker can be positioned between the Fc domains to join the fusion proteins together. For example, 1, 2, 3, 4 or more ACVR1, ACVR2A and/or ACVR2B Fc fusion proteins can be linked together.

Examples of ACVR2A and/or ACVR2B ECD fusion proteins have been described, such as those disclosed in U.S. Pat. Nos. 7,842,633; 7,960,343; and 7,709,605, each of which is incorporated by reference herein in their entirety.

One example of an ACVR2A antagonist is known as Sotatercept (also called ACE-011). Sotatercept contains the ECD of ACVR2A fused to a human IgG1 Fc domain and is described in detail in Carrancio et al., (2014) *British J Haematology.* 165(6):870-872, which is incorporated by reference herein in its entirety.

One example of an ACVR2B antagonist is known as ACE-031. ACE-031 contains the ECD of ACVR2B fused to a human IgG1 Fc domain and is described in detail in Sako et al., (2010) *J. Biol. Chem.* 285(27):21037-21048, which is incorporated by reference herein in its entirety.

Examples of ACVR1 ECD fusion proteins are known, such as those disclosed in Berasi, et al., (2011) *Growth Factors,* 29(4):128-139; which is incorporated by reference herein in its entirety.

C. Hybrid ECD Fusion Proteins

Hybrid or multispecific ECD fusion protein antagonists are also provided. Hybrid ECD fusion proteins can comprise a combination of two or more ACVR1, ACVR2A and/or ACVR2B ECDs. For example, the fusion proteins can comprise 1, 2, 3, 4 or more molecules of an ACVR1, ACVR2A and/or ACVR2B ECD. In one embodiment, the antagonist comprises an ACVR2A ECD linked to an ACVR2B ECD. In a further embodiment, the antagonist further comprises an Fc domain.

In one embodiment, a fusion protein can comprise one or more molecules of an ACVR2A ECD and one or more molecules of an ACVR2B ECD. In another embodiment, a fusion protein can comprise one or more molecules of an ACVR1 ECD and one or more molecules of an ACVR2A ECD. In another embodiment, a fusion protein can comprise one or more molecules of an ACVR1 ECD and one or more molecules of an ACVR2B ECD.

In one embodiment, a fusion protein comprises one or more ACVR2A ECD-Fc fusion proteins and one or more ACVR2B ECD-Fc fusion proteins which are complexed together. In another embodiment, a fusion protein comprises one or more ACVR1 ECD-Fc fusion proteins and one or more ACVR2A ECD-Fc fusion proteins which are complexed together. In another embodiment, a fusion protein comprises one or more ACVR1 ECD-Fc fusion proteins and one or more ACVR2B ECD-Fc fusion proteins which are complexed together. In such cases, the fusion proteins can be joined together via their Fc domains, for example, by at least one disulfide linkage or by a linker sequence. Alternatively, the ECD portions of the fusion protein can be joined together by a linker sequence.

In one embodiment, the antagonist comprises an ACVR2A ECD fused to a first Fc domain and an ACVR2B ECD fused to a second Fc domain. In such cases, the Fc domains can be complexed with one another. In another embodiment, the antagonist comprises a linker between the ACVR2A and ACVR2B ECDs, each fused to an Fc domain.

The fusion proteins can be constructed to generate ACVR1, ACVR2A, and/or ACVR2B antagonists in a tandem format. In one embodiment, a fusion protein comprises two or more ECDs from ACVR1, ACVR2A and/or ACVR2B in tandem followed by an Fc domain. In some cases the ECDs arranged in tandem are separated by a linker sequence. Such a tandem fusion protein can comprise 1, 2, 3, 4 or more ACVR1, ACVR2A and/or ACVR2B ECDs.

D. Antibody Antagonists

An ACVR1, ACVR2A or ACVR2B antagonist includes antibodies against (in other words specifically binding to) any of these receptors, preferably antibodies having an epitope within the extracellular domain. Specific binding of an antibody or fusion protein to its target antigen means an affinity of at least $10^6$, $10^7$, $10^8$, $10^9$, or $10^{10}$ M$^{-1}$. Specific binding is detectably higher in magnitude and distinguishable from non-specific binding occurring to at least one unrelated target. Methods for preparing antibodies are known to the art. See, for example, Kohler & Milstein (1975) *Nature* 256:495-497; and Harlow & Lane (1988) *Antibodies: a Laboratory Manual,* Cold Spring Harbor Lab., Cold Spring Harbor, NY.

Any antibody that inhibits or reduces the activity of ACVR1, ACVR2A and/or ACVR2B (e.g., an antagonist antibody) can be used. Such ACVR2A and ACVR2B antibodies include, for example, those antibodies disclosed in U.S. Pat. Nos. 8,486,403, 8,128,933, WO2009/137075, and Lach-Trifilieff, et al. (2014) *Mol. Cell Biol.* 34(4):606-618, each of which is incorporated by reference herein in their entirety. Humanized, chimeric and veneered forms of any of these antibodies are included as are antibodies competing for binding therewith.

In one embodiment, the antibody is an anti-ACVR2A antibody. In another embodiment, the antibody is an anti-ACVR2B antibody. In other embodiments, the antibody can be a bispecific antibody against both ACVR2A and ACVR2B. In another embodiment, the antibody is an anti-ACVR1 antibody. In other embodiments, the antibody can be a bispecific antibody against both ACVR1 and ACVR2A or against both ACVR1 and ACVR2B.

E. Small Molecule Antagonists

Antagonists of activin A, ACVR1, ACVR2A and ACVR2B can also be small molecule antagonists. Such small molecule antagonists can inhibit an activity of activin A, ACVR1, ACVR2A, or ACVR2B. Small molecule antagonists of ACVR1 include, for example, LDN-212854 described in Mohedas et al., (2013) *ACS Chem. Biol.* 8:1291-1302, which is incorporated by reference herein in its entirety.

V. Screening Assays

The activity of the various activin A, ACVR1, ACVR2A and/or ACVR2B antagonists and variants or fragments thereof provided herein can be screened in a variety of assays. For example, ACVR1, ACVR2A and/or ACVR2B antagonists and variants thereof can be screened for their ability to bind to ligands or bind to ACVR1, ACVR2A or ACVR2B receptors, for their ability to inhibit binding of a ligand to an ACVR1 and/or ACVR2 polypeptide, and/or for their ability to inhibit activity of the ACVR1 or ACVR2 receptors.

The activity of an ACVR1 or an ACVR2 antagonist or variants or fragments thereof can be tested in vitro or in cell based assays. In vitro binding assays and assays to measure inhibition of receptor activity are well known. Various assays to measure the activity of an ACVR1, ACVR2A or ACVR2B antagonist are described in detail, for example, in U.S. Pat. No. 7,842,663 which is incorporated by reference herein in its entirety.

The ability of the antagonist to modulate complex formation between the ACVR1 or ACVR2 polypeptide and its binding protein can be detected by a variety of techniques. For instance, modulation of the formation of complexes can be quantitated using, for example, detectably labeled proteins such as radiolabeled (e.g., $^{32}$P, $^{35}$S, $^{14}$C or $^3$H), fluorescently labeled (e.g., FITC), or enzymatically labeled ACVR1 or ACVR2 polypeptide or its binding protein, by immunoassay, or by chromatographic detection.

The ability of the ACVR1 or ACVR2 antagonist to inhibit ACVR1 or ACVR2 receptor-mediated signaling can be monitored. For example, the effects of downstream signaling such as Smad activation can be monitored using a Smad-responsive reporter gene.

ACVR1 and/or ACVR2 antagonists and variants or fragments thereof can also be screened for activity in an in vivo assay. For example, ACVR1 or ACVR2 antagonists or variants thereof can be screened for their ability to treat FOP in a mouse model of FOP (e.g., ability to decrease ectopic bone formation). Transgenic knock-in mice have been developed that carry a conditional allele encoding Acvr1 [R206H]. These Acvr1$[^{R206H]COIN/+}$ mice are described in U.S. Ser. No. 14/207,320 and PCT/US2014/026582, which are incorporated by reference herein in its entirety. This allele expresses the R206H variant only after activation by Cre recombinase. This allows Cre-dependent activation of Acvr1[R206H] expression at specific tissues and at specific time by using different types of Cre driver lines. In this manner the resulting mice also bypass the perinatal lethality that has been observed with a non-regulated knock-in allele of Acvr1[R206H]. Activation of Acvr1[R206H] expression in young or in adult mice results in ectopic bone formation. For example, Acvr1$^{[R206H]COIN/+}$;Gt(ROSA26)Sor$^{CreERt2/+}$ mice (wherein CreERt2 is a tamoxifen-regulatable recombinase (see Feil et al. (1997) *Biochem Biophys Res Commun.* 237(3):752-7) that has been introduced into the Gt(ROSA26)Sor locus, and hence it is constitutively and globally expressed) develop FOP after exposure to tamoxifen. Briefly, in the absence of tamoxifen, CreERt2 is inactive. Tamoxifen activates expression of Cre which then acts upon the Acvr1$^{[R206H]COIN/+}$ to convert it to Acvr1$^{[R206H]/+}$, thereby converting the genotype of the mice to mirror the genotype of the FOP patients that are ACVR1 [R206H]. The Acvr1$^{[R206H]}$ allele expresses Acvr1[R206H], and that is adequate to drive the development of FOP in the Acvr1$^{[R206H]/+}$;Gt(ROSA26)Sor$^{CreErt2/+}$ mice. This bypasses the embryonic lethality experienced with conventional Acvr1$^{[R206H]}$ knock-in mice, Acvr1$^{tm1Emsh}$ (http://www.informatics.jax.org/allele/key/828153). After tamoxifen treatment, the ACVR1, ACVR2A and/or ACVR2B antagonists or a control can be administered to the Acvr1$^{[R206H]COIN/+}$;Gt(ROSA26)Sor$^{CreERt2/+}$ mice and the animals monitored for ectopic bone formation. See Chakkalakal S A, et al. (20120 An Acvr1 R206H knock-in mouse has fibrodysplasia ossificans progressiva. J Bone Miner Res. 27(8):1746-56. This assay is described in detail in the Examples below.

VI. Fibrodysplasia Ossificans Progressiva (FOP)

FOP is a rare heritable disorder in which heterotopic ossification forms histologically and biomechanically 'normal' bone at extraskeletal sites, such as connective tissue. This disorder, although episodic, is cumulative, and results in permanent disability of increasing severity. FOP is a relentless, progressive, ultra-rare genetic disorder in which muscles, tendons and ligaments are progressively replaced by bone, a process known Heterotopic Ossification (HO). HO of the jaw, spine and rib cage can make it difficult to speak, eat or breathe, leading to weight loss and escalating loss of mobility and skeletal deformity. People with FOP also experience episodic, localized inflammation known as a "flare-ups" though HO may occur both silently as well as in association with symptoms. Most people with FOP are wheelchair bound by 30 years old and the median age of survival is approximately 40 years. Death often results from complications, such as pneumonia, heart failure and aspiration, stemming from HO and loss of mobility in the chest, neck and jaw.

FOP's worldwide prevalence is approximately 1/2,000,000. There are approximately 800-1000 patients diagnosed with FOP worldwide, with many others thought to remain undiagnosed or misdiagnosed. There is no ethnic, racial, gender, or geographic predilection to FOP. It is not only an extremely disabling disease but also a condition of considerably shortened lifespan.

Characteristics of FOP include, for example, congenital malformations of the great toe, flare-ups characterized by painful soft tissue swellings on the head, neck, and/or back with inflammation and progressive formation of heterotopic bone via endochondral ossification.

FOP can be suspected clinically based on the presence of malformations of the great toe. Diagnostic tests, such as x-rays or bone scan can substantiate great toe abnormalities and confirm the presence of heterotopic ossification. A FOP diagnosis can also be confirmed by genetic testing, for example, by detecting the 617 G-to-A (R206H) mutation in the ACVR1 gene.

It is common for FOP to be misdiagnosed as several other disorders, including other conditions of heterotopic ossification. FOP should be distinguished by a differential diagnosis from disorders including, for example, isolated congenital malformations, lymphedema, soft tissue sarcoma, desmoid tumors, aggressive juvenile fibromatosis, juvenile bunions, isolated brachydactyly, progressive osseous heteroplasia and heterotopic ossification. The presence of great toe congenital malformations and the painful soft-tissue flare-ups can be used to differentiate FOP from other disorders.

Patients with FOP have congenital malformations of the great toe but otherwise appear normal at birth. The flare-ups associated with FOP start during the first decade of life. Flare-ups can be triggered by, for example, soft tissue injury, falls, fatigue, viral infections or intramuscular injections. The result of the flare-ups is a transformation of soft tissue, such as ligaments, skeletal muscle or tendons into heterotopic bone.

There was no previous therapeutic treatment for FOP or for the prevention or reversal of HO associated with FOP. FOP was managed by preventative measures, such as improved safety and strategies to minimize injury, avoiding intramuscular injections and taking care when receiving dental care. High dose corticosteroid treatments started within the first 24 hours of a flare-up can help reduce the inflammation and edema associated with flare-ups. Surgical strategies to remove the heterotopic bone are not recommended as it is counterproductive and causes new trauma-induced heterotopic ossification.

A "new heterotopic ossification", "new heterotopic ossification lesion", "new bone lesion", or "new lesion", as used interchangeably herein, refers to a heterotopic ossification which is not pre-existing in a subject, e.g., prior to administration of the activin A antagonist, or at the time of administration of the activin A antagonist. In one embodiment, new heterotopic ossification may be prevented or have its volume reduced after administration of an activin A antagonist. In one embodiment, new heterotopic ossification may develop in a subject after undergoing surgery to remove pre-existing heterotopic ossification (and administration of the activin A antagonist could prevent such occurrence). The development of new heterotopic ossification lesions can be measured/determined using techniques that are standard in the art. For example, lesions can be determined by, for example, the use of positron emission tomography (PET), as discussed in more detail herein.

The "intensity" or "severity" of new heterotopic ossification lesions refers to any one or more of the adverse phenotypes used to analyze the formation of the new heterotopic ossification lesions, e.g., in terms of its activity, intensity, volume, daily average pain, rate of growth and mineralization, occurrence of painful flare-ups, and/or number of new heterotopic ossification lesions. The intensity, severity, or activity of the new heterotopic ossification lesions can be determined by, for example, the use of positron emission tomography (PET) with 18F-NaF PET. For example, Botman et al., 2019 (Bone. 2019 July; 124:1-6; incorporated in its entirety herein by reference), describes the use of 18F-NaF PET as a predictor of HO growth in FOP and serve as the basis for evaluation of active HO lesions specifically associated with high-intensity 18F-NaF PET signal. In one embodiment, Lesion Activity (LA)=Total signal of 18F-NaF in a lesion.

The volume of a single contiguous target or new heterotopic ossification lesion can be measured by one or more known methods in the art. In one embodiment, volumetric computed tomography (CT) can be used to measure the change in heterotopic bone formation, and determine the volume of the new heterotopic ossification lesion.

The Total Lesion Activity (TLA), as used herein, is defined as: TLA=Patient-level sum of lesion activity for all target and new lesions for a patient at a given time point–measure of growing and mineralizing HO burden.

The "rate of bone growth and mineralization activity" refers to the change in heterotopic bone formation. In one embodiment, 18F-NaF PET can be used to provide a sensitive, specific and whole body quantitative measure of bone growth and mineralization activity. In another embodiment, positron emission tomography (PET) with 18F-NaF PET and volumetric computed tomography (CT) can be used to measure the change in bone growth and mineralization activity.

The "daily average pain-NRS", refers to averaging the daily pain within each week by use of the 0-10 Numeric Rating Scale (NRS) for pain management. Assessment of pain intensity is considered one of the core outcome domains in clinical pain research (Dworkin et al., 2005; incorporated in its entirety herein by reference). The Numeric Rating Scale (NRS) is regarded as one of the best single-item methods available to estimate the intensity of pain (Jensen et al., 1999; Breivik et al., 2000; incorporated in their entirety herein by reference). The NRS assesses pain intensity using a 0-10 ranking scale with 0 representing "no pain" and 10 "unbearable pain" or comparable statement in relation to all lesion activity disclosed herein.

A "flare-up" refers to a painful and/or edematous swelling that may precede or accompany a heterotopic ossification or a new heterotopic ossification. Notably, heterotopic ossification and chronic disease progression has also been reported in the absence of flare-ups. Flare-ups are a significant burden for patients with FOP, whether associated with HO or not. The reduction in the frequency and intensity of flare-ups after administration of an activin A antagonist indicates that flare-ups in FOP are associated with activin A.

A "pre-existing lesion" refers to a lesion which is previously present in a subject, e.g., prior to administration and/or at the time of administration, and is not a new heterotopic ossification lesion. In one embodiment, administering a therapeutically effective amount of an activin A antagonist to a human subject does not affect pre-existing lesions on the subject. In one embodiment, administration of an effective amount of an activin A antagonist to a human subject does not affect the number of pre-existing lesions in the subject, as compared to the number of pre-existing lesions in the subject prior to administration. In one embodiment, administration of an effective amount of an activin A antagonist to a human subject does not affect volume of pre-existing lesions in the subject, as compared to the volume of pre-existing lesions in the subject prior to administration. In another embodiment, administering a therapeutically effective amount of an activin A antagonist does not reduce the intensity or severity of pre-existing lesions, as compared to the intensity or severity of pre-existing lesions in the subject prior to administration. In one embodiment, administering a therapeutically effective amount of an activin A antagonist to a human subject does not reduce the rate of heterotopic ossification lesion growth of pre-existing lesions and/or mineralization of pre-existing lesions, relative to a control subject. In one embodiment, administering a therapeutically effective amount of an activin A antagonist to a human subject does not reduce the number of pre-existing lesions, relative to a control subject. In one embodiment, administering a therapeutically effective amount of an activin A antagonist to a human subject does not reduce the intensity or activity of pre-existing lesions, relative to a control subject.

VII. Methods of Treatment

Methods of treating FOP, comprising administering to a subject having FOP a therapeutically effective amount of an activin A, ACVR1, ACVR2A and/or an ACVR2B antagonist are provided herein. In one embodiment, FOP is treated by administering a therapeutically effective amount of an activin A antagonist. In one embodiment, FOP is treated by administering a therapeutically effective amount of an antibody against activin A. In one embodiment, a therapeutically effective amount of an ACVR2A antagonist and an ACVR2B antagonist is administered. In a further embodiment, the ACVR2A antagonist is an Fc fusion protein and the ACVR2B antagonist is an Fc fusion protein.

In one aspect, the disclosure provides a method of reducing the intensity or severity of new heterotopic ossification lesions in a human subject with fibrodysplasia ossificans progressiva (FOP), the method comprising administering to a subject having FOP a therapeutically effective amount of an activin A antagonist. In one embodiment, the intensity or severity of new heterotopic ossification lesions in the human subject is reduced by at least 50%, by at least 40%, by at least 30%, by at least 20%, by at least 10%, or by at least 5% relative to a human subject who is not administered the activin A antagonist.

"Treating" a subject with FOP means administration of a therapeutically effective amount of an antibody against activin A, to a subject that has FOP, where the purpose is to cure, heal, alleviate, relieve, alter, remedy, ameliorate, improve, or affect the condition of one or more symptoms of FOP.

A "subject" is any animal (i.e., mammals) such as, humans, primates, rodents, such as mice and rats, agricultural and domesticated animals such as, dogs, cats, cattle, horses, pigs, sheep, and the like, in which one desires to treat FOP. In any of the present methods, the subject can be mammal, and preferably human.

A "control" refers to a sample, measurement, or value that serves as a reference for comparison to a subject's sample, measurement, or value. For example, a control can be taken, or measured, from a subject prior to administration of an activin A antagonist. In another embodiment, a control can be measured or taken from a subject at the time of administration of an activin A antagonist. A control can also represent an average measurement or value gathered from a population of similar individuals. In another embodiment, a control can be an average or median value or measurement gathered from a population of individuals having a disease or condition, e.g., FOP. In another embodiment, a control can be an average or median value or measurement gathered from a healthy population, e.g., a population not having FOP. One of ordinary skill in the art would recognize that controls can be designed for assessment of any number of parameters disclosed herein, e.g., HO lesion volume, new HO lesion number, etc.

A therapeutically effective amount of an activin A, ACVR1, ACVR2A and/or an ACVR2B antagonist, means a combination of dose, frequency and route of administration of an antagonist which brings a positive response in at least one sign or symptom of FOP. A positive response can include reducing, eliminating, ameliorating, inhibiting worsening of, or delaying at least one sign or symptom of FOP. Signs or symptoms of FOP that can be subject of a positive response include for example, ectopic or heterotopic bone formation, FOP flare-ups, or pain and swelling associated with flare-ups. The therapeutically effective amount can be assessed in a single patient by comparing signs and symptoms before and after treatment. An amount is considered effective if at least one sign or symptom gives a positive response following treatment. A therapeutically effective amount can alternatively or additionally be assessed by comparing signs and symptoms of population of subjects treated with an antagonist or antagonists of the present disclosure with a control population of subjects not receiving treatment. The subjects for such comparison can be an animal model, or human subjects in a clinical trial (e.g., phase I, phase II, IIa, IIb, or III). An amount is considered effective if there is a statistically significant positive response between the populations in at least one sign or symptom.

In one aspect, the present disclosure provides a method of preventing formation of new heterotopic ossification lesions in a human subject with FOP, the method comprising administering to the human subject a therapeutically effective amount of an activin A antagonist, thereby preventing the formation of new heterotopic ossification lesions in the human subject.

In another aspect, the present disclosure provides a method of reducing the intensity or severity of new heterotopic ossification lesions in a human subject with FOP, the method comprising administering to the human subject a therapeutically effective amount of an activin A antagonist, thereby reducing the intensity or severity of new heterotopic ossification lesions in the human subject.

In one embodiment, the human subject exhibits a decrease in intensity or severity of new heterotopic ossification lesions by at least 5%, at least 10%, at least 20%, at least 30%, at least 40%, at least 50%, at least 60%, at least 70%, at least 80%, at least 5-80%, at least 10-80%, at least 20-80%, at least 30-80%, at least 40-80%, at least 50-80%, at least 60-80%, at least 70-80%, at least 5-70%, at least 5-60%, at least 5-50%, at least 5-40%, at least 5-30%, at least 5-20%, or at least 5-10%, relative to a control subject. In one embodiment, the human subject exhibits a decrease in intensity or severity of new heterotopic ossification lesions by at least 5%, relative to a control subject. In one embodiment, the human subject exhibits a decrease in intensity or severity of new heterotopic ossification lesions by at least 10%, relative to a control subject. In one embodiment, the human subject exhibits a decrease in intensity or severity of new heterotopic ossification lesions by at least 20%, relative to a control subject. In one embodiment, the human subject exhibits a decrease in intensity or severity of new heterotopic ossification lesions by at least 30%, relative to a control subject. In one embodiment, the human subject exhibits a decrease in intensity or severity of new heterotopic ossification lesions by at least 40%, relative to a control subject. In one embodiment, the human subject exhibits a decrease in intensity or severity of new heterotopic ossification lesions by at least 50%, relative to a control subject. In one embodiment, the human subject exhibits a decrease in intensity or severity of new heterotopic ossification lesions by at least 60%, relative to a control subject. In one embodiment, the human subject exhibits a decrease in intensity or severity of new heterotopic ossification lesions by at least 70%, relative to a control subject. In one embodiment, the human subject exhibits a decrease in intensity or severity of new heterotopic ossification lesions by at least 80%, relative to a control subject. In one embodiment, the human subject exhibits a decrease in intensity or severity of new heterotopic ossification lesions by at least 5-80%, relative to a control subject. In one embodiment, the human subject exhibits a decrease in intensity or severity of new heterotopic ossification lesions by at least 10-80%, relative to a control subject. In one embodiment, the human subject exhibits a decrease in intensity or severity of new heterotopic ossification lesions by at least 20-80%, relative to a control subject. In one embodiment, the human subject exhibits a decrease in intensity or severity of new heterotopic ossification lesions by at least 30-80%, relative to a control subject. In one embodiment, the human subject exhibits a decrease in intensity or severity of new heterotopic ossification lesions by at least 40-80%, relative to a control subject. In one embodiment, the human subject exhibits a decrease in intensity or severity of new heterotopic ossification lesions by at least 50-80%, relative to a control subject. In one embodiment, the human subject exhibits a decrease in intensity or severity of new heterotopic ossification lesions by at least 60-80%, relative to a control subject. In one embodiment, the human subject exhibits a decrease in intensity or severity of new heterotopic ossification lesions by at least 70-80%, relative to a control subject. In one embodiment, the human subject exhibits a decrease in intensity or severity of new heterotopic ossification lesions by at least 5-70%, relative to a control subject. In one embodiment, the human subject exhibits a decrease in intensity or severity of new heterotopic ossification lesions by at least 5-60%, relative to a control subject. In one embodiment, the human subject exhibits a decrease in intensity or severity of new heterotopic ossification lesions by at least 5-50%, relative to a control subject. In one embodiment, the human subject exhibits a decrease in intensity or severity of new heterotopic ossification lesions by at least 5-40%, relative to a control subject. In one embodiment, the human subject exhibits a decrease in intensity or severity of new heterotopic ossification lesions by at least 5-30%, relative to a control subject. In one embodiment, the human subject exhibits a decrease in intensity or severity of new heterotopic ossification lesions by at least 5-20%, relative to a control subject. In one embodiment, the human subject exhibits a decrease in intensity or severity of new heterotopic ossification lesions by at least 5-10%, relative to a control subject.

In one embodiment, the human subject exhibits a decrease in total lesion activity of the heterotopic ossification lesions by at least 5%, at least 10%, at least 15%, at least 20%, at least 25%, at least 30%, at least 40%, at least 50%, at least 60%, at least 70%, at least 80%, at least 5-80%, at least 10-80%, at least 20-80%, at least 30-80%, at least 40-80%, at least 50-80%, at least 60-80%, at least 70-80%, at least 5-70%, at least 5-60%, at least 5-50%, at least 5-40%, at least 5-30%, at least 5-20%, or at least 5-10%, relative to a control subject. In one embodiment, the human subject exhibits a decrease in total lesion activity of the heterotopic ossification lesions by at least 5%, relative to a control subject. In one embodiment, the human subject exhibits a decrease in total lesion activity of the heterotopic ossification lesions by at least 10%, relative to a control subject. In one embodiment, the human subject exhibits a decrease in total lesion activity of the heterotopic ossification lesions by at least 15%, relative to a control subject. In one embodiment, the human subject exhibits a decrease in total lesion activity of the heterotopic ossification lesions by at least 20%, relative to a control subject. In one embodiment, the human subject exhibits a decrease in total lesion activity of the heterotopic ossification lesions by at least 25%, relative to a control subject. In one embodiment, the human subject exhibits a decrease in total lesion activity of the heterotopic ossification lesions by at least 30%, relative to a control subject. In one embodiment, the human subject exhibits a decrease in total lesion activity of the heterotopic ossification lesions by at least 40%, relative to a control subject. In one embodiment, the human subject exhibits a decrease in total lesion activity of the heterotopic ossification lesions by at least 50%, relative to a control subject. In one embodiment, the human subject exhibits a decrease in total lesion activity of the heterotopic ossification lesions by at least 60%, relative to a control subject. In one embodiment, the human subject exhibits a decrease in total lesion activity of the heterotopic ossification lesions by at least 70%, relative to a control subject. In one embodiment, the human subject exhibits a decrease in total lesion activity of the heterotopic ossification lesions by at least 80%, relative to a control subject. In one embodiment, the human subject exhibits a decrease in total lesion activity of the heterotopic ossification lesions by at least 5-80%, relative to a control subject. In one embodiment, the human subject exhibits a decrease in total lesion activity of the heterotopic ossification lesions by at least 10-80%, relative to a control subject. In one embodiment, the human subject exhibits a decrease in total lesion activity of the heterotopic ossification lesions by at least 20-80%, relative to a control subject. In one embodiment, the human subject exhibits a decrease in total lesion activity of the heterotopic ossification lesions by at least 30-80%, relative to a control subject. In one embodiment, the human subject exhibits a decrease in total lesion activity of the heterotopic ossification lesions by at least 40-80%, relative to a control subject. In one embodiment, the human subject exhibits a decrease in total lesion activity of the heterotopic ossification lesions by at least 50-80%, relative to a control subject. In one embodiment, the human subject exhibits a decrease in total lesion activity of the heterotopic ossification lesions by at least 60-80%, relative to a control subject. In one embodiment, the human subject exhibits a decrease in total lesion activity of the heterotopic ossification lesions by at least 70-80%, relative to a control subject. In one embodiment, the human subject exhibits a decrease in total lesion activity of the heterotopic ossification lesions by at least 5-70%, relative to a control subject. In one embodiment, the human subject exhibits a decrease in total lesion activity of the heterotopic ossification lesions by at least 5-60%, relative to a control subject. In one embodiment, the human subject exhibits a decrease in total lesion activity of the heterotopic ossification lesions by at least 5-50%, relative to a control subject. In one embodiment, the human subject exhibits a decrease in total lesion activity of the heterotopic ossification lesions by at least 5-40%, relative to a control subject. In one embodiment, the human subject exhibits a decrease in total lesion activity of the heterotopic ossification lesions by at least 5-30%, relative to a control subject. In one embodiment, the human subject exhibits a decrease in total lesion activity of the heterotopic ossification lesions by at least 5-20%, relative to a control subject. In one embodiment, the human subject exhibits a decrease in total lesion activity of the heterotopic ossification lesions by at least 5-10%, relative to a control subject.

In one embodiment, the human subject exhibits a decrease in daily average pain-NRS of about 0.2-fold, 0.5-fold, 1-fold, 1.5-fold, 2-fold, 3-fold, 0.2 to 3-fold, 0.5 to 3-fold, 1 to 3-fold, 1.5 to 3-fold, 2 to 3-fold, 2.5 to 3-fold, 0.2 to 2.5-fold, 0.2 to 2-fold, 0.2 to 1.5-fold, 0.2 to 1-fold, or 0.2 to 0.5-fold, relative to a control subject. In one embodiment, the human subject exhibits a decrease in daily average pain-NRS of about 0.2-fold, relative to a control subject. In one embodiment, the human subject exhibits a decrease in daily average pain-NRS of about 0.5-fold, relative to a control subject. In one embodiment, the human subject exhibits a decrease in daily average pain-NRS of about 1-fold, relative to a control subject. In one embodiment, the human subject exhibits a decrease in daily average pain-NRS of about 1.5-fold, relative to a control subject. In one embodiment, the human subject exhibits a decrease in daily average pain-NRS of about 2-fold, relative to a control subject. In one embodiment, the human subject exhibits a decrease in daily average pain-NRS of about 2.5-fold, relative to a control subject. In one embodiment, the human subject exhibits a decrease in daily average pain-NRS of about 3-fold, relative to a control subject. In one embodiment, the human subject exhibits a decrease in daily average pain-NRS of about 0.2 to 3-fold, relative to a control subject. In one embodiment, the human subject exhibits a decrease in daily average pain-NRS of about 0.5 to 3-fold, relative to a control subject. In one embodiment, the human subject exhibits a decrease in daily average pain-NRS of about 1 to 3-fold, relative to a control subject. In one embodiment, the human subject exhibits a decrease in daily average pain-NRS of about 1.5 to 3-fold, relative to a control subject. In one embodiment, the human subject exhibits a decrease in daily average pain-NRS of about 2 to 3-fold, relative to a control subject. In one embodiment, the human subject exhibits a decrease in daily average pain-NRS of about 2.5 to 3-fold, relative to a control subject. In one embodiment, the human subject exhibits a decrease in daily average pain-NRS of about 0.2 to 2.5-fold, relative to a control subject. In one embodiment, the human subject exhibits a decrease in daily average pain-NRS of about 0.2 to 2-fold, relative to a control subject. In one embodiment, the human subject exhibits a decrease in daily average pain-NRS of about 0.2 to 1.5-fold, relative to a control subject. In one embodiment, the human subject exhibits a decrease in daily average pain-NRS of about 0.2 to 1-fold, relative to a control subject. In one embodiment, the human subject exhibits a decrease in daily average pain-NRS of about 0.2 to 0.5-fold, relative to a control subject.

In one embodiment, the human subject exhibits a decrease in new heterotopic ossification lesion volume by at least 5%, at least 10%, at least 15%, at least 20%, at least 25%, at least 30%, at least 40%, at least 50%, at least 5-50%, at least 10-50%, at least 20-50%, at least 30-50%, at least 40-50%, at least 5-40%, at least 5-30%, at least 5-20%, or at least 5-10%, relative to a control subject. In one embodiment, the human subject exhibits a decrease in new heterotopic ossification lesion volume by at least 5%, relative to a control subject. In one embodiment, the human subject exhibits a decrease in new heterotopic ossification lesion volume by at least 10%, relative to a control subject. In one embodiment, the human subject exhibits a decrease in new heterotopic ossification lesion volume by at least 15%, relative to a control subject. In one embodiment, the human subject exhibits a decrease in new heterotopic ossification lesion volume by at least 20%, relative to a control subject. In one embodiment, the human subject exhibits a decrease in new heterotopic ossification lesion volume by at least 25%, relative to a control subject. In one embodiment, the human subject exhibits a decrease in new heterotopic ossification lesion volume by at least 30%, relative to a control subject. In one embodiment, the human subject exhibits a decrease in new heterotopic ossification lesion volume by at least 40%, relative to a control subject. In one embodiment, the human subject exhibits a decrease in new heterotopic ossification lesion volume by at least 50%, relative to a control subject. In one embodiment, the human subject exhibits a decrease in new heterotopic ossification lesion volume by at least 5-50%, relative to a control subject. In one embodiment, the human subject exhibits a decrease in new heterotopic ossification lesion volume by at least 10-50%, relative to a control subject. In one embodiment, the human subject exhibits a decrease in new heterotopic ossification lesion volume by at least 20-50%, relative to a control subject. In one embodiment, the human subject exhibits a decrease in new heterotopic ossification lesion volume by at least 30-50%, relative to a control subject. In one embodiment, the human subject exhibits a decrease in new heterotopic ossification lesion volume by at least 40-50%, relative to a control subject. In one embodiment, the human subject exhibits a decrease in new heterotopic ossification lesion volume by at least 5-40%, relative to a control subject. In one embodiment, the human subject exhibits a decrease in new heterotopic ossification lesion volume by at least 5-30%, relative to a control subject. In one embodiment, the human subject exhibits a decrease in new heterotopic ossification lesion volume by at least 5-20%, relative to a control subject. In one embodiment, the human subject exhibits a decrease in new heterotopic ossification lesion volume by at least 5-10%, relative to a control subject.

In one embodiment, the human subject exhibits a decrease in rate of new heterotopic ossification lesion growth and mineralization by at least 5%, at least 10%, at least 20%, at least 30%, at least 40%, at least 50%, at least 5-50%, at least 10-50%, at least 20-50%, at least 30-50%, at least 40-50%, at least 5-40%, at least 5-30%, at least 5-20%, or at least 5-10%, relative to a control subject. In one embodiment, the human subject exhibits a decrease in rate of new heterotopic ossification lesion growth and mineralization by at least 5%, relative to a control subject. In one embodiment, the human subject exhibits a decrease in rate of new heterotopic ossification lesion growth and mineralization by at least 10%, relative to a control subject. In one embodiment, the human subject exhibits a decrease in rate of new heterotopic ossification lesion growth and mineralization by at least 20%, relative to a control subject. In one embodiment, the human subject exhibits a decrease in rate of new heterotopic ossification lesion growth and mineralization by at least 30%, relative to a control subject. In one embodiment, the human subject exhibits a decrease in rate of new heterotopic ossification lesion growth and mineralization by at least 40%, relative to a control subject. In one embodiment, the human subject exhibits a decrease in rate of new heterotopic ossification lesion growth and mineralization by at least 50%, relative to a control subject. In one embodiment, the human subject exhibits a decrease in rate of new heterotopic ossification lesion growth and mineralization by at least 5-50%, relative to a control subject. In one embodiment, the human subject exhibits a decrease in rate of new heterotopic ossification lesion growth and mineralization by at least 10-50%, relative to a control subject. In one embodiment, the human subject exhibits a decrease in rate of new heterotopic ossification lesion growth and mineralization by at least 20-50%, relative to a control subject. In one embodiment, the human subject exhibits a decrease in rate of new heterotopic ossification lesion growth and mineralization by at least 30-50%, relative to a control subject. In one embodiment, the human subject exhibits a decrease in rate of new heterotopic ossification lesion growth and mineralization by at least 40-50%, relative to a control subject. In one embodiment, the human subject exhibits a decrease in rate of new heterotopic ossification lesion growth and mineralization by at least 5-40%, relative to a control subject. In one embodiment, the human subject exhibits a decrease in rate of new heterotopic ossification lesion growth and mineralization by at least 5-30%, relative to a control subject. In one embodiment, the human subject exhibits a decrease in rate of new heterotopic ossification lesion growth and mineralization by at least 5-20%, relative to a control subject. In one embodiment, the human subject exhibits a decrease in rate of new heterotopic ossification lesion growth and mineralization by at least 5-10%, relative to a control subject.

In one embodiment, the human subject exhibits a decrease in new heterotopic ossification lesion intensity by at least 5%, at least 10%, at least 20%, at least 30%, at least 40%, at least 50%, at least 5-50%, at least 10-50%, at least 20-50%, at least 30-50%, at least 40-50%, at least 5-40%, at least 5-30%, at least 5-20%, or at least 5-10%, relative to a control subject. In one embodiment, the human subject exhibits a decrease in new heterotopic ossification lesion intensity by at least 5%, relative to a control subject. In one embodiment, the human subject exhibits a decrease in new heterotopic ossification lesion intensity by at least 10%, relative to a control subject. In one embodiment, the human subject exhibits a decrease in new heterotopic ossification lesion intensity by at least 20%, relative to a control subject. In one embodiment, the human subject exhibits a decrease in new heterotopic ossification lesion intensity by at least 30%, relative to a control subject. In one embodiment, the human subject exhibits a decrease in new heterotopic ossification lesion intensity by at least 40%, relative to a control subject. In one embodiment, the human subject exhibits a decrease in new heterotopic ossification lesion intensity by at least 50%, relative to a control subject. In one embodiment, the human subject exhibits a decrease in new heterotopic ossification lesion intensity by at least 5-50%, relative to a control subject. In one embodiment, the human subject exhibits a decrease in new heterotopic ossification lesion intensity by at least 10-50%, relative to a control subject. In one embodiment, the human subject exhibits a decrease in new heterotopic ossification lesion intensity by at least 20-50%, relative to a control subject. In one embodiment, the human subject exhibits a decrease in new heterotopic ossification lesion intensity by at least 30-50%, relative to a control subject. In one embodiment, the human subject exhibits a decrease in new heterotopic ossification lesion intensity by at least 40-50%, relative to a control subject. In one embodiment, the human subject exhibits a decrease in new heterotopic ossification lesion intensity by at least 5-40%, relative to a control subject. In one embodiment, the human subject exhibits a decrease in new heterotopic ossification lesion intensity by at least 5-30%, relative to a control subject. In one embodiment, the human subject exhibits a decrease in new heterotopic ossification lesion intensity by at least 5-20%, relative to a control subject. In one embodiment, the human subject exhibits a decrease in new heterotopic ossification lesion intensity by at least 5-10%, relative to a control subject.

In one embodiment, the human subject exhibits a decrease in number of new heterotopic ossification lesions by at least 5%, at least 10%, at least 20%, at least 30%, at least 40%, at least 50%, at least 60%, at least 70%, at least 80%, at least 90%, at least 5-90%, at least 10-90%, at least 20-90%, at least 30-90%, at least 40-90%, at least 50-90%, at least 60-90%, at least 70-90%, at least 80-90%, at least 5-80%, at least 5-70%, at least 5-60%, at least 5-50%, at least 5-40%, at least 5-30%, at least 5-20%, or at least 5-10%, relative to a control subject. In one embodiment, the human subject exhibits a decrease in number of new heterotopic ossification lesions by at least 5%, relative to a control subject. In one embodiment, the human subject exhibits a decrease in number of new heterotopic ossification lesions by at least 10%, relative to a control subject. In one embodiment, the human subject exhibits a decrease in number of new heterotopic ossification lesions by at least 20%, relative to a control subject. In one embodiment, the human subject exhibits a decrease in number of new heterotopic ossification lesions by at least 30%, relative to a control subject. In one embodiment, the human subject exhibits a decrease in number of new heterotopic ossification lesions by at least 40%, relative to a control subject. In one embodiment, the human subject exhibits a decrease in number of new heterotopic ossification lesions by at least 50%, relative to a control subject. In one embodiment, the human subject exhibits a decrease in number of new heterotopic ossification lesions by at least 60%, relative to a control subject. In one embodiment, the human subject exhibits a decrease in number of new heterotopic ossification lesions by at least 70%, relative to a control subject. In one embodiment, the human subject exhibits a decrease in number of new heterotopic ossification lesions by at least 80%, relative to a control subject. In one embodiment, the human subject exhibits a decrease in number of new heterotopic ossification lesions by at least 90%, relative to a control subject. In one embodiment, the human subject exhibits a decrease in number of new heterotopic ossification lesions by at least 5-90%, relative to a control subject. In one embodiment, the human subject exhibits a decrease in number of new heterotopic ossification lesions by at least 10-90%, relative to a control subject. In one embodiment, the human subject exhibits a decrease in number of new heterotopic ossification lesions by at least 20-90%, relative to a control subject. In one embodiment, the human subject exhibits a decrease in number of new heterotopic ossification lesions by at least 30-90%, relative to a control subject. In one embodiment, the human subject exhibits a decrease in number of new heterotopic ossification lesions by at least 40-90%, relative to a control subject. In one embodiment, the human subject exhibits a decrease in number of new heterotopic ossification lesions by at least 50-90%, relative to a control subject. In one embodiment, the human subject exhibits a decrease in number of new heterotopic ossification lesions by at least 60-90%, relative to a control subject. In one embodiment, the human subject exhibits a decrease in number of new heterotopic ossification lesions by at least 70-90%, relative to a control subject. In one embodiment, the human subject exhibits a decrease in number of new heterotopic ossification lesions by at least 80-90%, relative to a control subject. In one embodiment, the human subject exhibits a decrease in number of new heterotopic ossification lesions by at least 5-80%, relative to a control subject. In one embodiment, the human subject exhibits a decrease in number of new heterotopic ossification lesions by at least 5-70%, relative to a control subject. In one embodiment, the human subject exhibits a decrease in number of new heterotopic ossification lesions by at least 5-60%, relative to a control subject. In one embodiment, the human subject exhibits a decrease in number of new heterotopic ossification lesions by at least 5-50%, relative to a control subject. In one embodiment, the human subject exhibits a decrease in number of new heterotopic ossification lesions by at least 5-40%, relative to a control subject. In one embodiment, the human subject exhibits a decrease in number of new heterotopic ossification lesions by at least 5-30%, relative to a control subject. In one embodiment, the human subject exhibits a decrease in number of new heterotopic ossification lesions by at least 5-20%, relative to a control subject. In one embodiment, the human subject exhibits a decrease in number of new heterotopic ossification lesions by at least 5-10%, relative to a control subject.

In some methods for treating FOP, the subject does not have and is not at risk of other conditions treatable with antagonists against activin A, ACVR1, ACVR2A, and/or ACVR2B. For example, the subject can be free of any or all of type II diabetes, muscular dystrophy, amyotrophic lateral sclerosis (ALS) and osteoporosis.

A. Methods of Administration activin A, ACVR1, ACVR2A and/or ACVR2B antagonists, are usually administered directly as proteins or small molecules, but in the case of proteins can also be administered as nucleic acid encoding such proteins. Such antagonists can be administered by various methods, such as cellular transfection, gene therapy, direct administration with a delivery vehicle or pharmaceutically acceptable carrier, indirect delivery by providing recombinant cells comprising a nucleic acid encoding an activin A, ACVR1, ACVR2A and/or ACVR2B antagonist, or an antibody against activin A, provided herein.

Various delivery systems can be used to administer the activin A, ACVR1, ACVR2A and/or ACVR2B antagonists, or an antibody against activin A, provided herein, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc.

Methods of administration can be enteral or parenteral and include intradermal, intramuscular, intraperitoneal, intravenous, subcutaneous, pulmonary, intranasal, intraocular, epidural, and oral routes. The compounds can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. In addition, it can be desirable to introduce the pharmaceutical compositions of the disclosure into the central nervous system by any suitable route, including intraventricular and intrathecal injection; intraventricular injection can be facilitated by an intraventricular catheter, for example, attached to a reservoir, such as an Omcana reservoir. Pulmonary administration can also be employed, e.g., by use of an inhaler or nebulizer, and formulation with an aerosolizing agent.

The pharmaceutical compositions of the disclosure can be administered locally to the area in need of treatment; this can be achieved, for example, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In another embodiment, the active agent can be delivered in a controlled release system. In one embodiment, a pump can be used (see Langer (1990) supra). In another embodiment, polymeric materials can be used (see Howard et al. (1989) J. Neurosurg. 71:105). In another embodiment where the active agent of the disclosure is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

B. Combination Therapies

The activin A, ACVR1, ACVR2A and ACVR2B antagonists, or an antibody against activin A, provided herein can be administered in combination with one another or other treatments. In one embodiment, the method of treating FOP involves co-administration of an ACVR2A antagonist and an ACVR2B antagonist. In another embodiment, the method of treating FOP involves co-administration of an ACVR1, an ACVR2A and an ACVR2B antagonist. In other embodiments, an ACVR1 antagonist can be co-administered with an ACVR2A and/or an ACVR2B antagonist. The ACVR1, ACVR2A and ACVR2B antagonists can be administered as separate pharmaceutical compositions or can be administered as a single pharmaceutical composition comprising a combination of these agents. The ACVR1, ACVR2A and/or ACVR2B antagonists, or an antibody against activin A, either alone or in combination, can be administered in conjunction with one or more additional therapeutic compounds. The combination therapy can encompass simultaneous or alternating administration. In addition, the combination can encompass acute or chronic administration.

C. Pharmaceutical Compositions

The present disclosure also provides pharmaceutical compositions comprising an activin A, ACVR1, ACVR2A and/or an ACVR2B antagonist, or an antibody against activin A, provided herein and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In one embodiment, the composition is formulated in accordance with routine procedures as a pharmaceutical composition adapted for intravenous administration to human beings. When necessary, the composition can also include a solubilizing agent and a local anesthetic such as lidocaine to ease pain at the site of the injection. When the composition is to be administered by infusion, it can be dispensed with an infusion bottle containing sterile pharmaceutical grade water or saline. When the composition is administered by injection, an ampoule of sterile water for injection or saline can be provided so that the ingredients can be mixed prior to administration.

The activin A, ACVR1, ACVR2A and/or an ACVR2B antagonists, or an antibody against activin A, provided herein can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The amount and frequency of the activin A, ACVR1, ACVR2A and/or ACVR2B antagonist, or an antibody against activin A, administered by a specified route effective in the treatment of FOP (e.g., a therapeutically effective amount) can be determined by standard clinical techniques based on the present description. In addition, in vitro assays can be employed to help identify optimal dosage ranges. The precise dose to be employed in the formulation also depends on the route of administration, and the seriousness of the condition, and should be decided according to the judgment of the practitioner and each subject's circumstances. However, suitable dosage ranges for parenteral administration, preferably intravenous or subcutaneous, are generally about 20-50000 micrograms of active compound per kilogram body weight. For antibodies to activin A suitable dosage ranges include 1-25 mg/kg, 2-20 mg/kg 5-15 mg/kg, 8-12 mg/kg and 10 mg/kg. Suitable dosage ranges for intranasal administration are generally about 0.01 pg/kg body weight to 1 mg/kg body weight. Effective doses can be extrapolated from dose-response curves derived from in vitro or animal model test systems.

Frequencies of administration also vary depending on the severity of the condition and half-life of the agent among other factors, but are typically between daily and quarterly, including for example, twice a week, weekly, fortnightly, monthly, bimonthly. Agents can also be administered at irregular intervals responsive to the patient's condition or reduction in serum level of the agent below a threshold among other factors.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise.

EXAMPLES

Example 1: Reduction in Formation of New Bone Lesion Activity in Patients with Fibrodysplasia Ossificans Progressiva (FOP)

In subjects with FOP, bone forms in soft tissue outside of the normal skeleton, a process known as heterotopic (in the wrong place) ossification (HO). A pivotal double-blind placebo-controlled trial was performed for evaluating an activin A antagonist, e.g., garetosmab, in patients with FOP. On the primary endpoints, garetosmab reduced new HO bone growth from baseline by 25% as measured by CT scan and reduced average rate of lesion growth and mineralization over 28 weeks by 25%, as measured by more sensitive PET bone scans. Garetosmab showed a statistically significant 50% reduction on the PET bone scan results at the 28-week time point alone (post-hoc analysis), largely driven by a significant decrease in the incidence and intensity of new lesions. Garetosmab reduced the incidence of new bone lesions by approximately 90% as measured by both PET and CT scans and reduced the incidence of patient-reported flare-ups by half.

The results of this placebo-controlled trial demonstrate an effective treatment that can nearly extinguish new HO bone formation and flare-ups with a nearly 90% reduction in the incidence of new bone, a groundbreaking result for people with FOP. These data also significantly improve the understanding of the disease by demonstrating through PET imaging that untreated people with FOP experience far more frequent and widespread bone lesions than previously thought.

The study enrolled 44 adult patients (18-60 years old) from the United States and Europe with a clinical diagnosis of FOP and documentation of an ACVR1 genetic mutation. The trial employed 18F-NaF PET imaging and CT scans to investigate the effect of garetosmab on change in HO in patients with FOP. 18F-NaF is a widely approved and extensively used bone-seeking PET tracer with high sensitivity to detect abnormal bone growth, turnover and mineralization in several bone-related diseases such as Paget's disease and cancers with bone involvement. The study has a three-period trial design consisting of a randomized, double-blind placebo-controlled treatment period (6 months), open-label treatment period, during which placebo-treated patients cross over to garetosmab treatment (6 months) and open-label follow-up treatment. The primary analysis was recorded at week 28.

The key clinical results from the study are summarized in Table 1 below. All endpoints are at 28 weeks and were assessed by blinded, independent central review.

TABLE 1

| | garetosmab | Placebo | Difference | p-value |
|---|---|---|---|---|
| Average total bone lesion activity by PET (time weighted average over 28 weeks)* | −8.1% | +16.6% | −24.6% | 0.074 |
| Percent change in total bone lesion activity by PET at Week 28† | −27.3% | +21.6% | −48.9% | 0.043 |
| Percent change from baseline in HO volume by CT at Week 28* | 7.1% | 32.0% | −24.9% | 0.373 |
| Average change from baseline in daily average pain-NRS (time weighted average over 28 weeks)** | −0.51 | −0.17 | −0.34 | 0.266 |
| Percent change from baseline in mean bone lesion intensity (SUVmax) at week 8** | −22.3% | −6.6% | −15.7% | 0.007 |
| Percent change from baseline in average bone lesion intensity (SUVmax) at week 28† | −34.0% | −11.6% | −22.4% | <0.0001 |
| Number of new bone lesions measured by PET over 28 weeks† | 0.15 (total 3 new PET lesions with total bone lesion activity per patient = 34.8) | 1.19 (total 29 new PET lesions with total bone lesion activity per patient = 449.4) | 87.4% decrease (0.126 rate ratio) | 0.006 |

TABLE 1-continued

| | garetosmab | Placebo | Difference | p-value |
|---|---|---|---|---|
| Number of new CT bone lesions per patient[†] | 0.15 (total 3 new CT lesions with total CT volume per patient = 7.1 cm$^3$) | 1.13 (total 27 new CT lesions with total CT volume per patient = 22.3 cm$^3$) | 86.7% decrease (0.133 rate ratio) | 0.009 |
| Percent of patients with new bone lesions measured by PET over 28 weeks[†] | 15% (3/20) | 46% (11/24) | −31% | 0.05 |
| Percent of patients with new bone lesions measured by CT over 28 weeks[†] | 15% (3/20) | 46% (11/24) | −31% | 0.05 |
| Percent of patients with flare-ups, assessed by patient e-diary[^] | 35% (7/20) | 71% (17/24) | −36% | 0.032 |
| Percent of patients with investigator-assessed flare-ups[†] | 10% (2/20) | 42% (10/24) | −32% | 0.039 |

*Primary endpoint
**Prespecified endpoint
^Exploratory endpoint
[†]Post hoc analysis During the 28-week treatment period, garetosmab was observed to be generally well-tolerated. Any serious adverse events (SAEs) were deemed related to severity of underlying disease. Treatment emergent adverse events (TEAEs) occurred in 100% of both placebo and treated groups; the vast majority were mild to moderate in severity. Notable imbalances in TEAEs included epistaxis (50.0% vs 16.7%) and skin events (madarosis [loss of eyebrows, 25.0% vs 0%], acne [30.0% vs 8.3%] and a composite of skin infections including abscess, carbuncle, folliculitis, furuncle). Two treated patients in the open-label portion of the trial developed serious abscesses requiring hospitalization for drainage but reportedly resolved while continuing garetosmab treatment. One patient in the open-label portion of the trial died due to trauma unrelated to treatment.

Garetosmab vs placebo decreased total lesion activity percent change from baseline average of the week 8 and week 28 timepoint (−24.6, p 0.07), primary endpoint; there was no decrease at the week 8 endpoint but at the week 28 endpoint (end of DB period) the decrease was 49% (nominal p=0.043). This was largely driven by a dramatic marked decrease in the incidence, intensity and lesion activity of new lesions. Total lesion activity in new lesions (as measured by PET week 28) was decreased by 97% (p=0.009), while total volume of new lesions (as measured by CT at week 28) was decreased by 90% (p=0.017). Substantial decreases were seen in patient reported flare ups (51%) and investigator reported AE flare ups (76%). Treatment with Garetosmab also demonstrated an acceptable safety profile.

The activin A blockade by an activin A antagonist, e.g., garetosmab can markedly reduce the occurrence of new abnormal bone formation and painful flare-ups. These data strongly support the hypothesis that activin A is an important trigger of both flare-ups and new bone lesions in patients with FOP.

Example 2: An Activin a Antagonist Prevents New Heterotopic Ossification (HO)

A 28-week randomized double-blind placebo-controlled study (period 1) was performed in order to test whether an activin A antagonist, such as garetosmab, would shut down activin A dependent signaling for heterotopic bone formation in human subjects with FOP.

Positron emission tomography (PET) with 18F-NaF PET and volumetric computed tomography (CT) were used to measure the change in heterotopic bone formation. 18F-NaF PET has been shown in several other disease settings to provide a sensitive, specific and whole body quantitative measure of bone mineralization activity. Data published by Botman, 2019 (incorporated in its entirety herein by reference) support the use of 18F NaF PET as a predictor of HO growth in FOP and serve as the basis for evaluation of active HO lesions specifically associated with high-intensity 18F-NaF PET signal. Furthermore, volumetric assessment of HO lesions by CT over 6 months also allowed the assessment of growth of HO lesions and transition of PET detectable lesions to CT detectable mature HO lesions. Garetosmab was observed to rapidly reduce $^{18}$F-NaF uptake (by PET), and prevent new heterotopic bone formation (by CT).

The study was designed with 80% power to detect reduction of 57% in 28-week average total lesion activity (PET), 40% reduction in $^{18}$F-NaF SUVmax at week 8, and 60% difference in total volume by CT. 100% of 44 patients enrolled had active HO at baseline as detected by PET. The results demonstrate that garetosmab inhibited the appearance of new lesions but did not halt progression of established lesions (Table 2). Garetosmab was also observed to be well tolerated. SAEs more frequent in garetosmab treated patient with no trends and likely reflected the severity of disease. Notable imbalances in AEs included epistaxis (50.0% vs 16.7%) and skin events—madarosis (25.0% vs 0%), acne (30.0% vs 8.3%) and a composite of skin infections (e.g., abscess, carbuncle, folliculitis, furuncle).

As depicted in the schematic of the study design (FIG. 1), this study consisted of a screening/baseline period (day −28 to day −1), two 6-month treatment periods, and a follow-up treatment period (Period 3). The 3 treatment periods are: Period 1: a 6-month randomized double-blind placebo-controlled treatment period; Period 2: a 6-month open-label garetosmab treatment period; Period 3: a follow-up treatment period with garetosmab continuing until patients have completed the week 76 visit, and all data have been collected and validated through the time when the last patient randomized into the study completes the week 28 visit (Period 1) and results of the primary analyses of safety and efficacy are available to the sponsor.

Emerging data (Eekhoff et al., JBMR 2017 & Bone 2017, Upadhyay et al., JBMR 2017; each of which is incorporated in its entirety herein by reference) suggested that PET scans could identify "active" bone lesions. As a surrogate for preventing new lesions, the effect of garetosmab on these "active" bone lesions was studied. Thus, the primary endpoint assessed "total lesion activity" (TLA) as measured by PET in both existing and potentially new bone lesions, as assessed by size and intensity (assessed uptake of tracer). Multiple other endpoints captured total lesions and new lesions as assessed by both PET and CT, and also captured flare ups reported by patients and investigators. The primary analysis (TLA by PET) as well as multiple other analyses of bone lesions (including by CT) indicated that treatment with garetosmab is associated with an overall decrease of about 25%, compared to placebo. These decreases were almost entirely driven by an approximate 90% reduction in new lesions as assessed by PET or CT at 28 weeks. This was attributed to the surprisingly high frequency of new lesions in FOP patients (11/24 placebo patients had an average of 2.7 new lesions over 28 weeks, compared to 3/20 garetosmab patients who had one lesion each). There were also substantial decreases in patient reported flare ups (50%) and investigator reported AE flare ups (76%). These data demonstrate that activin A is required for the formation of new bone lesions in FOP patients; however, it does not seem to have a major role in existing PET-positive and CT bone lesions.

TABLE 2

| Endpoint | Result |
| --- | --- |
| Total lesion activity over 28 weeks (by 18F-NaF PET) | −24.6% (95% CI: −51.8, +2.5) $p = 0.0741$ |
| Total volume of HO lesions at week 28 (by CT) | −24.9% (95% CI: −80.8, +30.9) $p = 0.3726$ |
| Pain NRS over 28 weeks | −0.34 (95% CI: −0.96, +0.27) $p = 0.2656$ |
| Change in SUVmax at week 28 | −34% (95% CI: −32.6, −12.2) $p < 0.0001$ |
| Total number of new lesions by PET over 28 weeks | Pbo: 1.19 new lesions/pt; 29 new lesions Gar: 0.15/pt new lesions; 3 new lesions $p = 0.0063$ |
| Total number of new lesions by CT over 28 weeks | Pbo: 1.13 new lesions/pt; 27 total new lesions Gar: 0.15/pt new lesions; 3 total new lesions $p = 0.05$ |
| Percent of patients with new lesions by PET over 28 weeks | Pbo: 46% vs Gar: 15%, $p = 0.05$ |
| Percent of patients with new lesions by CT over 28 weeks | Pbo: 46% vs Gar: 15%, $p = 0.05$ |
| Percent of patients with Flares-ups | Pbo: 42% vs Gar: 10%, $p = 0.038$ |

Imaging

Figure 2A:
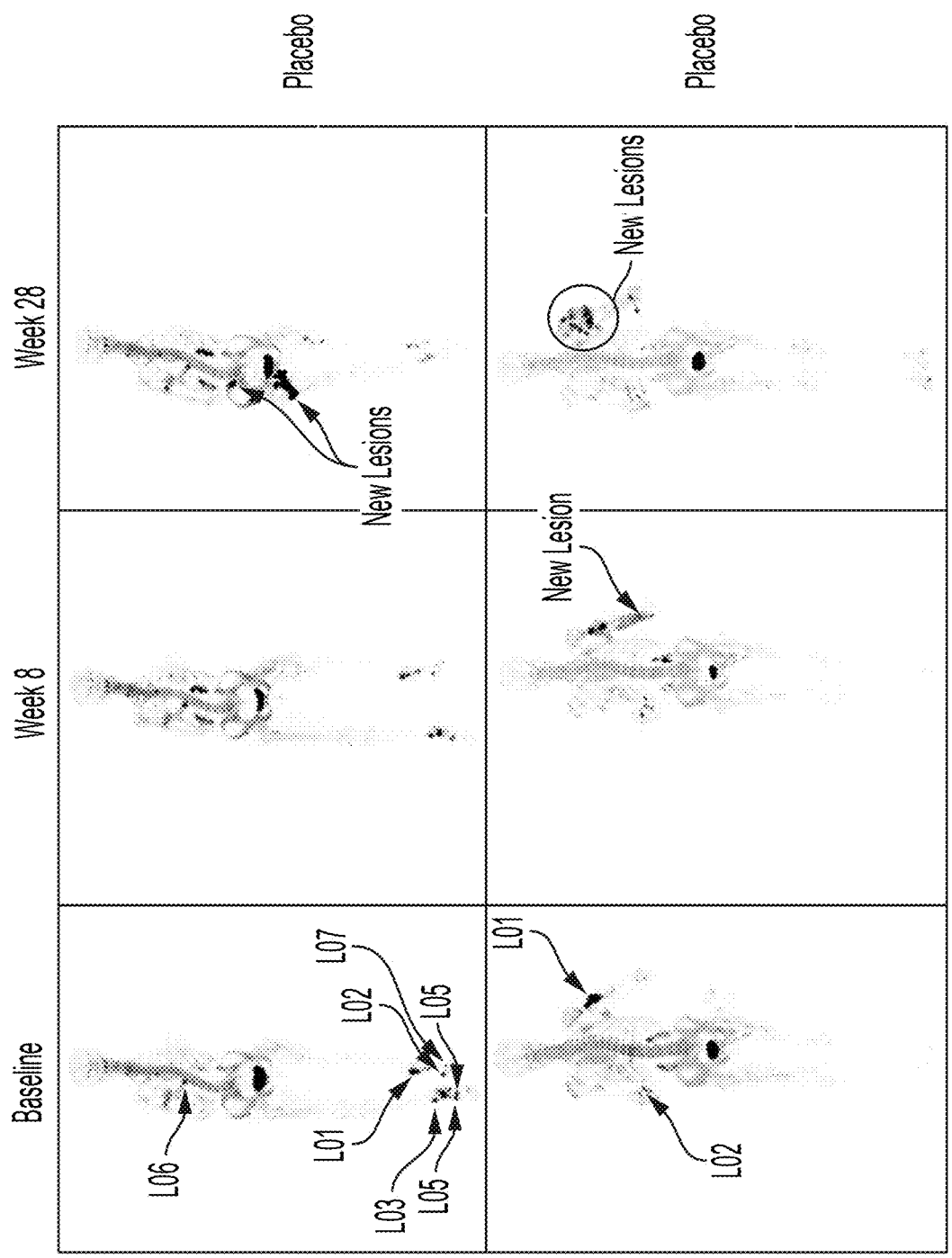
FIGS. 2A and 2B show PET imaging, which demonstrates FOP disease progression (FIG. 2A), and the effect of an activin A antagonist on heterotopic ossification (HO) lesions (FIG. 2B).
Figure 2B:
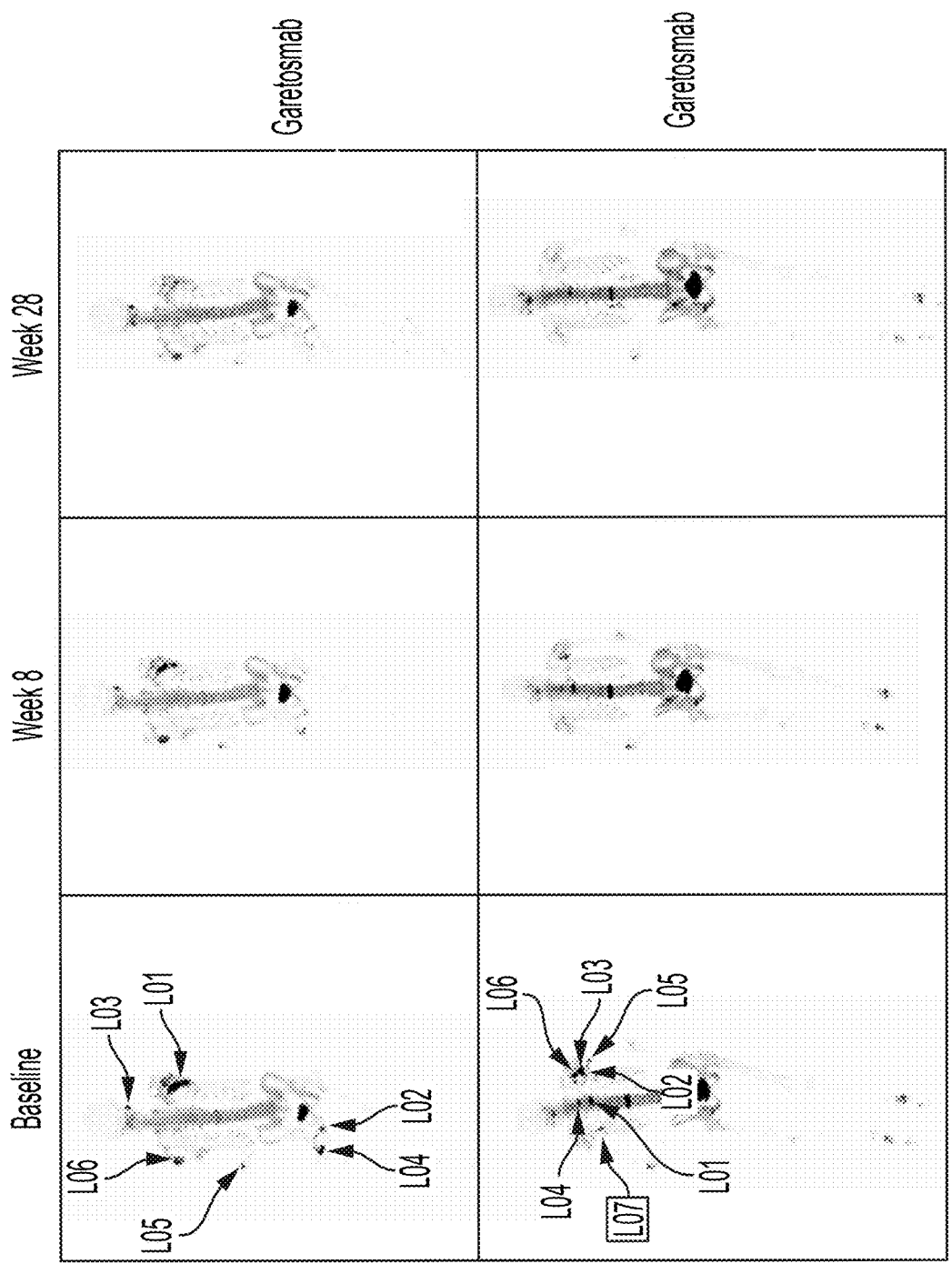

Radiolabeled 18F sodium fluoride was injected into patients and combined PET/CT images were taken of each patient. The details of the PET/CT imaging analysis is indicated as follows:

PET: Standardized Uptake Value (SUV) is measurement of radioactivity from the scan. SUVmean=Mean concentration of 18F-NaF in a region of interest (ROI) such as heterotopic ossification (HO)—how "hot" is the ROI on average. SUVmax=Maximum ("hottest") pixel within an ROI. Lesion Activity (LA)=Total signal of 18F-NaF in a lesion. Average SUV across entire metabolic volume (MV) of lesion on PET. Total Lesion Activity (TLA)=Patient-level sum of LA for all target and new lesions for a patient at a given time point–measure of growing and mineralizing HO burden. Time Weighted Average (TWA) of % change TLA=average over 28 weeks of the % change in TLA used to assess change in burden of growing and mineralizing HO across time points. The PET imaging clearly demonstrated disease progression (FIG. 2A), and the effect of garetosmab on HO lesions (FIG. 2B).

CT: HO Volume=volume of a single contiguous target or new HO lesion. Total HO Volume=sum of volumes of patient-level target and HO lesions at a given time point–measure formed HO burden.

Figure 3A:
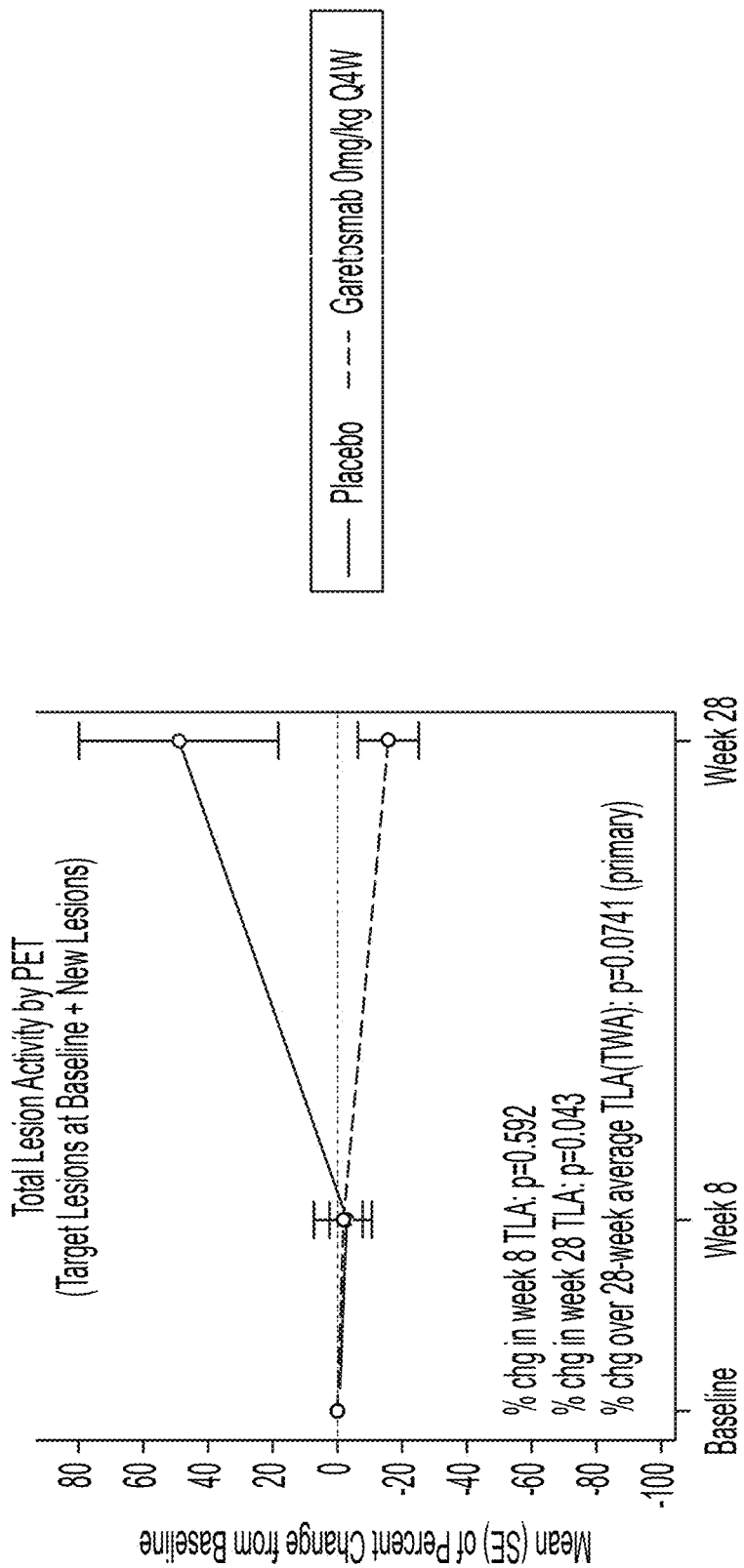
FIG. 3A shows that treatment with an activin A antagonist reduced total lesion activity, as analyzed by PET imaging, by approximately 25% (p=0.074); similar reductions were also observed by CT analysis.
Figure 3B:
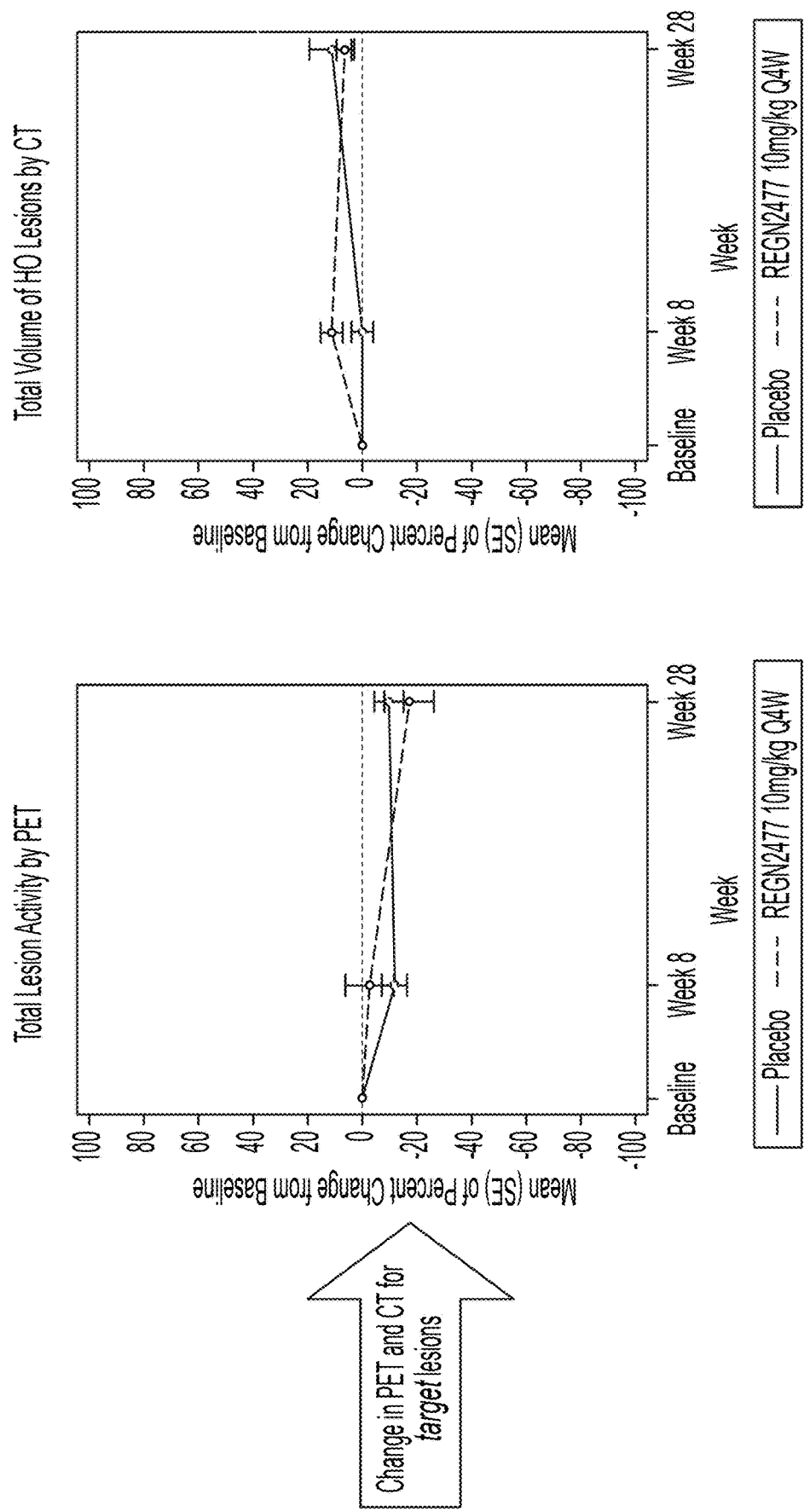
FIG. 3B shows the results from the PET/CT imaging analysis, which demonstrate that the effect of an activin A antagonist is more evident when existing ("target") lesions are examined separately from new lesions.
Figure 3B:
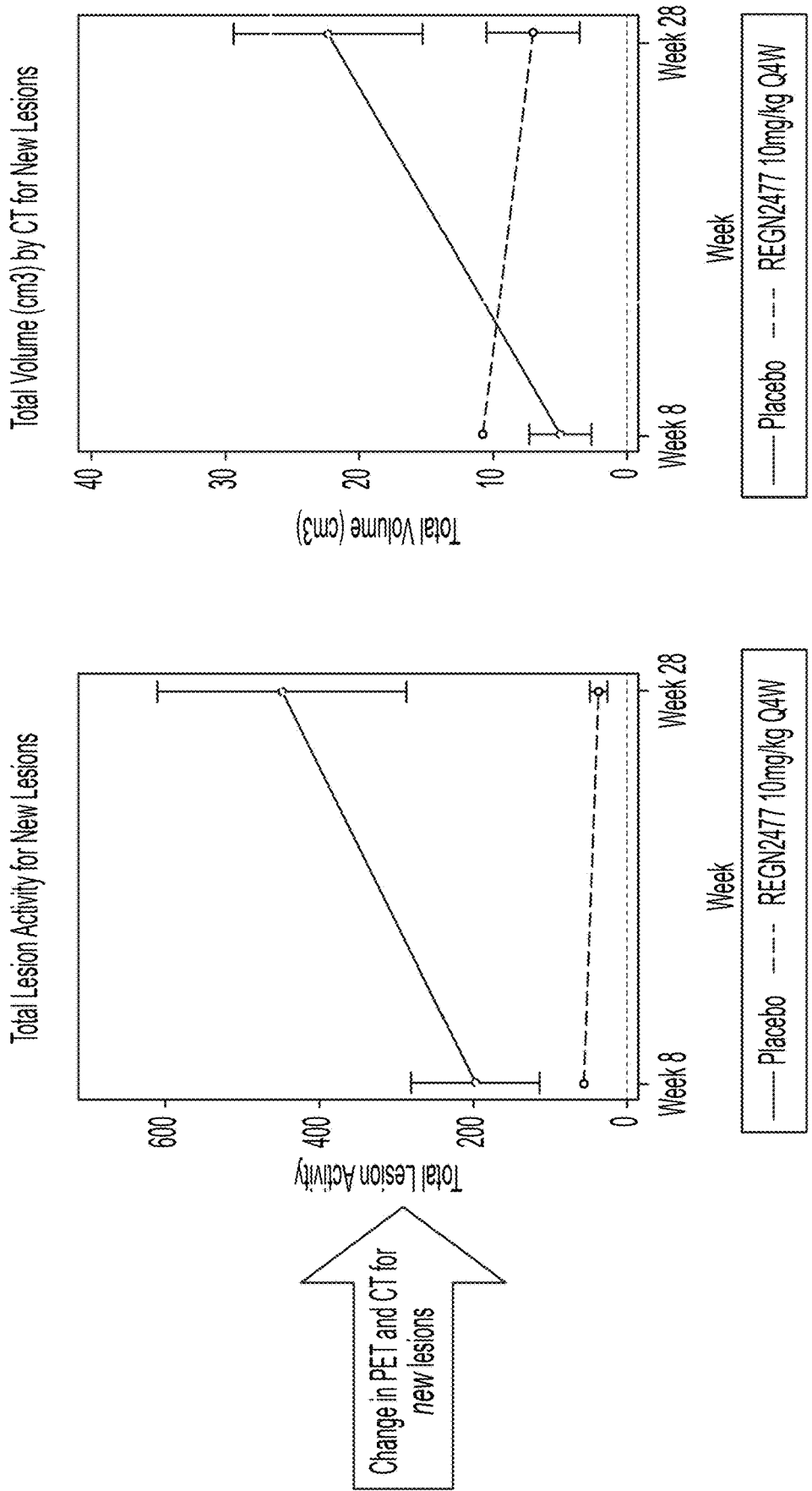

The results from the imaging analysis demonstrate that, when existing ("target") lesions are examined separately from new lesions, effect of garetosmab is more evident (FIG. 3A-3B).

Efficacy

Garetosmab was observed to decrease total lesion activity (both new and existing) from baseline when averaged at the week 8 and week 28 timepoints (−25%, p=0.074). There was no decrease at the week 8 endpoint (p=0.592) but at the week 28 endpoint (end of DB period) the decrease was 49% (nominal p=0.043). This was largely driven by a dramatic decrease in the incidence, activity (PET) and volume (CT) of new lesions. Total lesion activity in new lesions (as measured by PET week 28) was decreased by 97% (p=0.009), while total volume of new lesions (as measured by CT at week 28) was decreased by 90% (p=0.017). All endpoints were pre-specified (except number of patients with new HO lesion by CT) and assessed by blinded, independent central review. Lesions were assessed by PET/CT bone scan. 100% correlation of new lesion was determined by measure of PET scan with simultaneous assessment of CT scan. There were also substantial decreases in patient reported flare ups (51%) and investigator reported AE flare ups (76%). These data strongly support the notion that activin A is a required ligand for the formation of new lesions in patients with FOP. Activin A does not seem to play a key role in the progression of existing PET/CT lesions. Therefore, blocking activin A provides an opportunity for changing the course of disease for these long-suffering patients.

Safety

During the 28-week treatment period treatment emergent adverse events (TEAEs) occurred in 100% of both placebo and treated groups; the majority were mild to moderate in severity. Notable imbalances in TEAEs included epistaxis (50.0% vs 16.7%) and skin events (madarosis [loss of eyebrows, 25.0% vs 0%], acne [30.0% vs 8.3%] and a composite of skin infections including abscess, carbuncle, folliculitis, furuncle).

Example 3: Study Design and Interpretation

How the Study Design Differs from Other Studies

A phase 2, randomized, double-blind, placebo-controlled study was performed to evaluate the safety, tolerability, and effects on heterotopic bone formation of intravenous garetosmab (administered at 10 mg/kg every 4 weeks) in adults with FOP. This eliminates potential imbalances and biases associated with external, historical controls and unblinded assessments.

What Heterotopic Ossification (HO) Volume Tells Us about the Disease

Progressive HO is the defining characteristic of FOP. HO volume may reflect disease activity and the potential for joints to become immobilized. Location of the HO matters to patients and can be clinically meaningful. While volume of bone is directionally pertinent, the number and location of lesions is an important measure of disease activity. In the study, the primary endpoint is focused on total lesion activity versus placebo. For example, a small amount of bone from a new lesion in a joint, like an elbow, might lock it for life, while significant bone can be added in less movement-critical areas or in areas with existing HO may have far less of an effect. Additionally, the interpretation of "average volume" changes may be challenging when analyzing a data set with 1 or 2 outliers with either small or large volume increases.

Imaging Rationale
Imaging Analysis

Lesions are identified as HO by their density and morphology, consistent with that of abnormal bone, and location consistent with skeletal muscle, tendons or ligaments as identified in the CT scan. It was identified by 2 independent readers who were blinded to the samples and confirmed by an independent adjudicator who was also blinded. They were all board-certified radiologists.

Criteria for Lesion Selection and Rationale for Study Design and Imaging Analysis The criteria for lesion selection were clearly defined in the imaging charter and approved by the FDA. Additional posthoc image analyses are performed to better understand the natural history of FOP and the effect of garetosmab on HO formation. The "up to 7 lesions" were specified because that many lesions were not expected and because going above that number of lesions would not be practical for the readers. The lesions were chosen based on having 3-fold the intensity on PET over normotopic remodeling bone.

Exclusion of False Positives Due to Inflamed Osteochondroma or Osteoarthritis The imaging charter instructed the 2 independent readers and independent adjudicator who were board-certified radiologists, to carefully avoid regions of PET that are associated with non-HO pathologies by virtue of their location (e.g., joints), or by their features from the CT scan, whenever those are consistent with degenerative disease, osteochondromas, etc. All readers also received training on the imaging charter.

Bone Scintigraphy in Comparison with $^{18}$FNaF PET/CT for Detecting Osteoblastic Activity Technetium-99m methylene diphosphonate ($^{99}$mTcMDP) bone scintigraphy is widely used to detect osteoblastic activity. PET/CT is a molecular imaging technology that combines cross-sectional functional and anatomic imaging for diagnosis. Fluorine-18 fluoride ($^{18}$F-Fluoride) is a highly sensitive bone-seeking PET tracer used for detection of skeletal abnormalities. The uptake mechanism of $^{18}$F-Fluoride resembles that of $^{99}$mTcMDP. However, $^{18}$F-Fluoride displays better pharmacokinetic characteristics including faster blood clearance and two-fold higher uptake in bone. Uptake of $^{18}$F-Fluoride reflects blood flow and bone remodeling. The use of novel hybrid PET/CT systems has significantly improved the specificity of $^{18}$F-Fluoride imaging, as the CT component of the study allows morphologic characterization of the functional lesion and more accurate differentiation between benign lesions and metastases.

Fluorine-18 sodium fluoride positron emission tomography-computed tomography ($^{18}$FNaF PET/CT) imaging has higher sensitivity and higher spatial resolution compared with $^{99}$mTcMDP bone scintigraphy. In addition, the quality of the $^{18}$FNaF PET/CT images is better and they can be quantified more accurately. This is due to lower plasma protein binding and higher uptake in bone.

$^{18}$FNaF PET is a highly sensitive technique that is commonly used in research. $^{18}$FNaF PET was used as a benchmark in the study to assess whether CT imaging would produce comparable results. The data shows that CT can be used to monitor disease progression with comparable sensitivity to $^{18}$FNaF PET, thus confirming its ability to be used in clinical practice.

Clinical Data

The study was based on the hypothesis of blocking activin A and preventing new lesion formation, and the totality of the initial 28 week results are encouraging.

A longer-term 56-week study is performed, in which placebo patients will crossover to the garetosmab arm to further understand and put these results into context. The main effect of garetosmab is on the prevention of new lesions. The data on the primary endpoint elegantly illustrates that TLA was clearly reduced after week 8 of treatment when many more new lesions appeared in the placebo group, in comparison to the garetosmab group. On average the placebo group gained approximately 10 cm$^3$ more new HO over the 28 week study period as compared with the garetosmab group (mean change from baseline 16.7 cm$^3$ versus 6.5 cm$^3$).

A high proportion of patients with FOP die as a result of thoracic insufficiency, so assessing the impact of treatment with garetosmab on lung function is of interest. The data demonstrates that garetosmab preserves lung function compared to placebo by means of preventing new HO at week 28.

Impact of Garetosmab on FOP

Inhibitory levels of garetosmab should be consistent over long intervals to prevent progression of established HO lesions or the prevention of new HO lesions. FOP is a chronic disease with ongoing HO, some of which is silent and not associated with flare-ups. Therefore, to control it, the dosing has to be chronic. The levels of medicine in the patient's serum should always be above activin A saturating levels to prevent progression or development of new HO.

Pediatric Study

A 56-week Phase 2 study is performed for evaluation in both pediatric and adult patients.

Unlike palvarotene, pre-clinical data with garetosmab showed no effect on growth plates. The data demonstrates that there were no changes on the uptake of $^{18}$FNaF in the normal bone of adult FOP patients.

A dose level of 10 mg/kg by IV administration every four-weeks (Q4W), has been studied in adult patients with FOP. The adverse effects reported in this study (e.g., headache, epistaxis and skin & soft tissue infections) don't appear to be related to drug exposures (Cmax, Cmin, or AUC) among the patients. The reason for the inclusion of a dose confirmation cohort (Cohort A) in the pediatric study is not related to safety concerns, but rather to choose the dose regimen for each body weight group (i.e., patients <30 kg or >30 kg) that will achieve similar exposure in pediatric patients as that associated with efficacy in adult patients in the study.

The following dose regimens are proposed for the pediatric study in patients with FOP: 15 mg/kg IV Q4W for patients weighing less than 30 kg; and 10 mg/kg IV Q4W for patients weighing at or above 30 kg. In the initial study, 10 mg/kg IV Q4W, dose was studied in adult patients with FOP, which showed a beneficial response in efficacy and an acceptable safety profile. In this study, following the 10 mg/kg IV Q4W dose, the median (range) of the steady-state trough concentration was 120.7 (68.1-199.0) mg/L in adult patients with FOP. Based on the concentration data of garetosmab and total activin A generated in the initial study and on the two first-in-human (FIH) studies, maintenance of concentrations of garetosmab above about 50 mg/L is associated with saturation of the target-mediated elimination pathway, as evidenced by constant levels of total activin A around 0.05-0.06 mg/L. The exposure observed in adult patients with 10 mg/kg IV Q4W dose is considered to provide marked efficacy benefit, by maintaining the saturation of the target-mediated elimination pathway, with maximum target engagement in most of the patients.

In pediatric patients with FOP, per simulations using a population PK model based on data from adult healthy subjects and adult patients with FOP, the proposed dose for cohort A (15 mg/kg IV Q4W for patients less than 30 kg, or 10 mg/kg IV Q4W for patients at or above 30 kg) is expected to match the exposure in adult patients at 10 mg/kg IV Q4W studied in the initial study. Based on the results of the analyses from the 8 patients receiving active drug in Cohort A, the dose may be adjusted in one or more of the body weight group(s) to ensure drug exposure comparable to adults in the initial study. Cohort B patients will only begin to receive study drug after the dose has been confirmed based on data from Day 1 through Day 85 in patients enrolled in Cohort A. Since the objective is target saturation to ensure efficacy, different doses in FOP patients are explored. Modeling for pediatrics guides us to dose up to 15 mg/ml to meet target saturation in smaller children. There is no data from the toxicology studies that suggest an increased safety risk in children.

Procedure Overview for the PET-Scan and CT-Scan Imaging

The review of the PET/CT scans is treated as pre-specified, central, independent, and blinded. After study week 28, patients in the placebo arm are transitioned to garetosmab and since then all study participants receive the active drug. To perform the study's primary analysis, the study treatment assignment during the double-blind placebo-controlled period (Period 1) was unblinded. However, it is important to note that the individual treatment assignment during period 1 is neither disclosed to investigators/site personnel, nor to the independent imaging readers or the imaging adjudicator. The study sponsor is also blinded to the imaging results and will not have access to the scans until the week 56 database lock. This allows the imaging readers to perform a blinded analysis of the PET/CT scans at week 56. Also, between week 28 and week 56, and even afterwards (most patients are beyond week 76), investigators continue to make their clinical assessment of the study patients without being certain of what they received during the placebo-controlled periods.

Example 4: An Activin a Antagonist Prevents New Heterotopic Ossification (HO)

Study Design

A phase 2, randomized, double-blind, placebo-controlled study was designed to evaluate the safety, tolerability, pharmacokinetics, and efficacy of 10 mg/kg Garetosmab dosed every 4 weeks (Q4W) in adult patients with Fibrodysplasia ossificans progressiva (FOP). Efficacy is assessed by $^{18}$F-NaF positron emission tomography (PET) and low-dose X-Ray computed tomography (CT) imaging analysis of heterotopic (HO) bone formation. There was an expectation that compared to placebo, the study would show that: a) Garetosmab is well tolerated; b) Garetosmab reduces HO by demonstrating a reduction in PET signal and an inhibition of the growth of HO by volumetric CT; and c) Garetosmab inhibits the development of new HO lesions as assessed by PET and CT.

This study consists of a 4-week screening/baseline period, a 6-month randomized double-blind placebo-controlled treatment period (Period 1), a 6-month open-label garetosmab treatment period (Period 2), and a follow-up treatment period with open-label garetosmab (Period 3). The primary analysis was conducted when all the patients completed the double-blind treatment (Period 1). All primary and secondary week 28 efficacy endpoints were analyzed on the active HO analysis set (AHO, n=44) which included patients with any FOP related ACVR1 mutation, and on the active HO ACVR1[R206H] mutation set (AHOC, n=42). Imaging charter of the study defined active patients as those patients that had at least one heterotopic ossification lesion demonstrating uptake of $^{18}$F-NaF PET of at least three times that of normal reference bone as assessed by central review. Similarly, the criteria for the identification of the new HO lesions by PET and CT were pre-specified in the imaging charter. Safety analyses were performed on the Safety Analysis Set and included all available data as of the data cutoff date. Patient Disposition A total of 44 patients were randomized (20 patients in garetosmab arm and 24 patients in placebo arm). Forty-three (98%) patients completed the double-blind treatment period; 1 patient from garetosmab group discontinued from the study during the double-blind period due to an adverse event of pyrexia (see below for details). All 43 patients who completed the double-blind period, entered the open-label Period 2. As of the data cut-off date, 12 patients had entered follow-up treatment Period 3. One patient in Period 3 died due to severe head trauma after a fall (unrelated to treatment). Demographic and baseline disease characteristics of the AHO, AHOC and SAF population were balanced between the two treatment groups.

Efficacy Results

Figure 4:
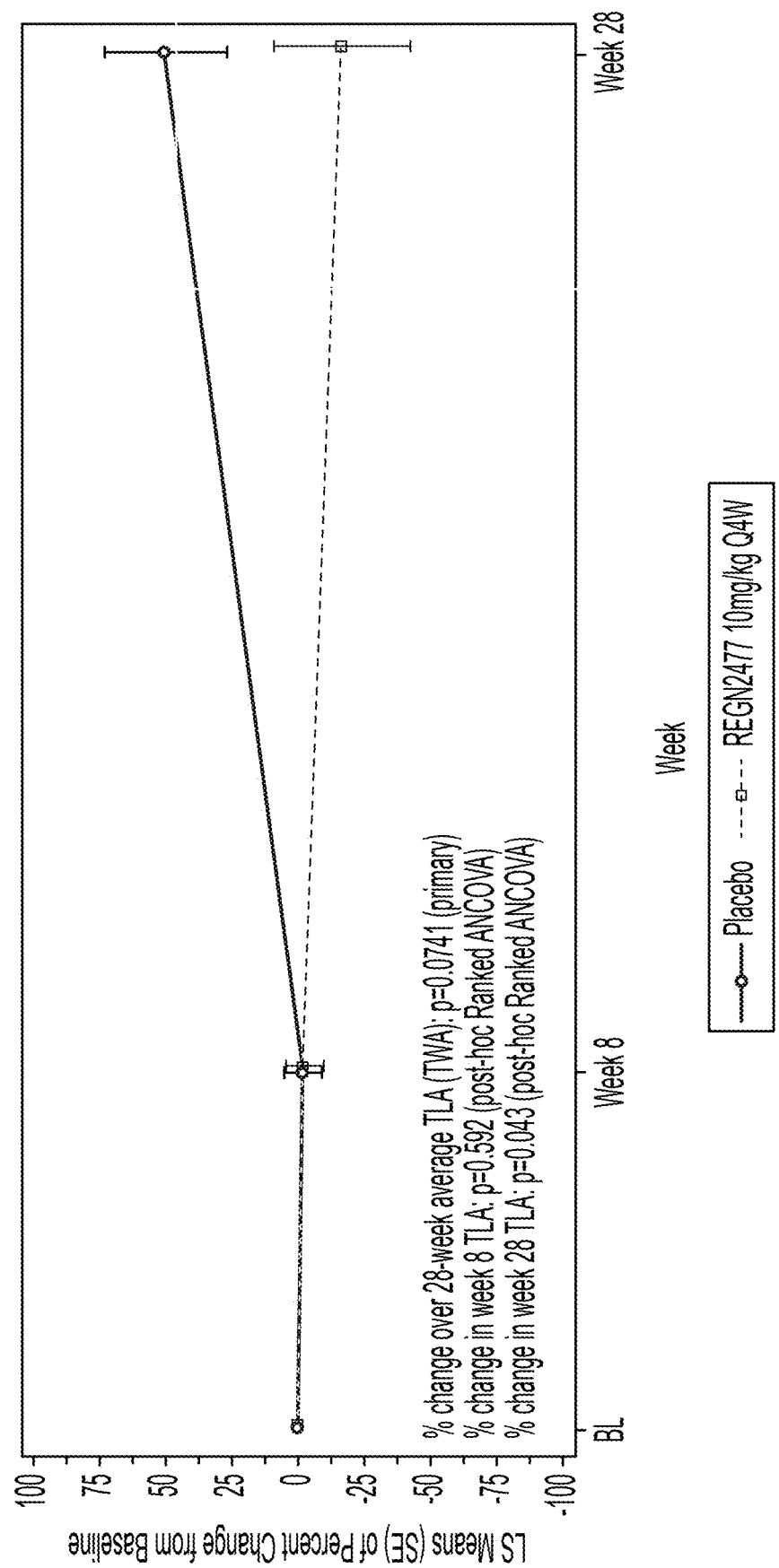
FIG. 4 depicts the percent change from baseline in total lesion activity by $^{18}$F-NaF PET in active HO analysis set (AHO).
Figure 5:
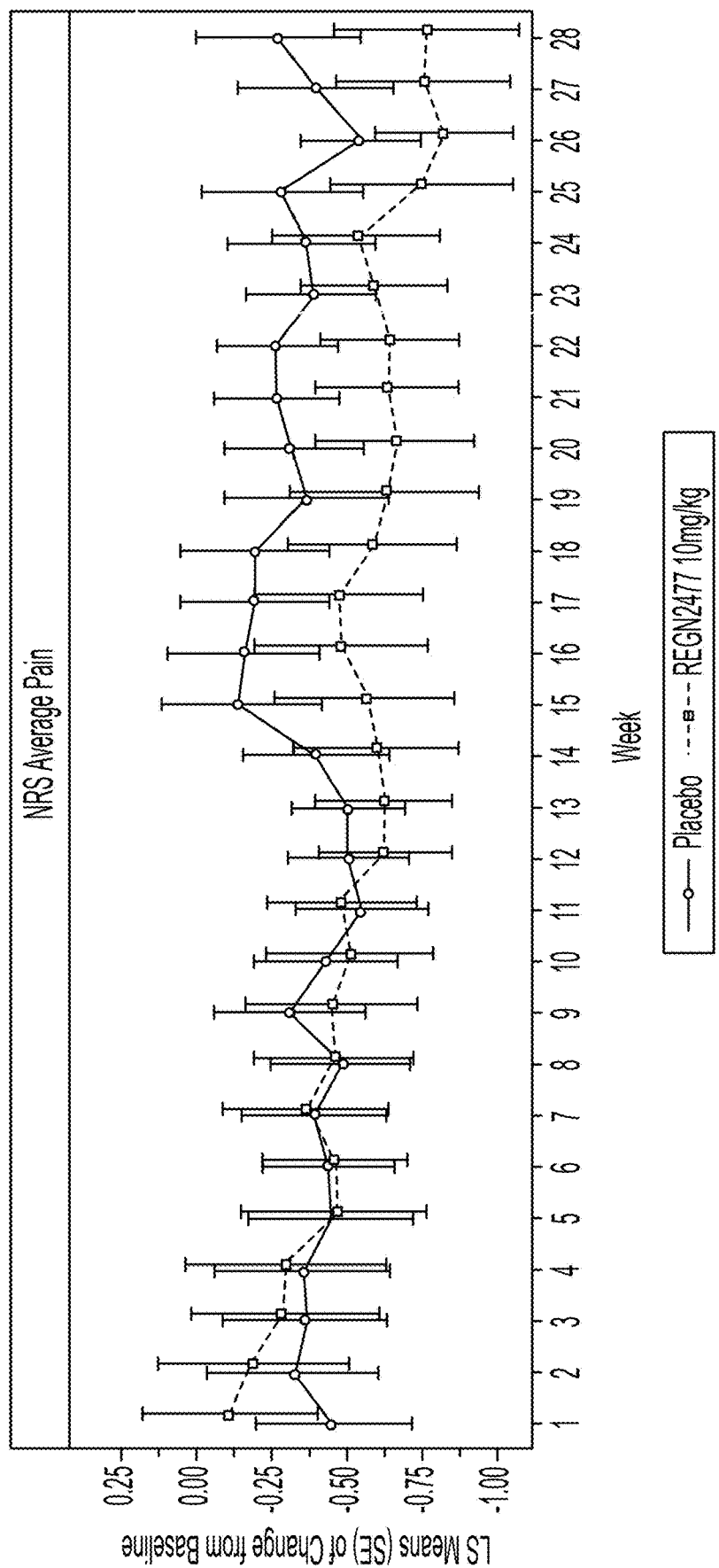
FIG. 5 depicts the change from baseline in weekly average pain by the Numeric Rating Scale (NRS) in active HO analysis set (AHO).

Results of all primary and key secondary endpoints that were tested using the statistical hierarchy are presented in Table 3 (in the order of the statistical hierarchy). Garetosmab reduced average total lesion activity (by $^{18}$F-NaF PET) from baseline over 28 weeks by approximately 25% (LS mean difference) from baseline compared to placebo (p=0.0741) in AHO. Post-hoc analysis demonstrated that the reduction in total lesion activity may not occur at a constant rate. The percent change in total lesion activity from baseline to week 8 was similar in both treatment groups, the percent change in total lesion activity from baseline to week 28 was lower in garetosmab group compared to placebo (post-hoc; p=0.043; FIG. 4). With regard to other endpoints, approximately 25% (LS mean difference) reduction from baseline compared to placebo was also observed in total volume of HO lesions (by CT) at week 28 (p=0.3726) in AHO. Similar results were observed in AHOC population. There was a favorable trend for reduced daily average pain in garetosmab arm compared to placebo in AHO (FIG. 5). Similar results were observed in AHOC. The reduction in garetosmab arm compared to placebo in total lesion activity by PET and in total volume of HO lesions by CT were mainly driven by the efficacy of garetosmab in reducing new lesion growth.

TABLE 3

Primary and Key Secondary Efficacy Endpoints Results in the Statistical Hierarchy

| Endpoint | Statistical Method | LS Mean (SE) REGN2477 | LS Mean (SE) Placebo | LS Mean Difference (95% CI) for REGN2477-Placebo | p-value |
|---|---|---|---|---|---|
| Time weighted average of percent change from baseline in total lesion activity by $^{18}$F-NaF PET over 28 weeks (AHO) | ANCOVA | −8.1 (9.93) | 16.6 (9.13) | −24.6 (−51.8, 2.5) | 0.0741 |
| Percent change from baseline in the total volume of HO lesions as assessed by CT at week 28 (AHO) | MMRM | 7.1 (20.43) | 32.0 (18.66) | −24.9 (−80.8, 30.9) | 0.3726 |
| Time weighted average of percent change from baseline in total lesion activity by $^{18}$F-NaF PET over 28 weeks (AHOC) | ANCOVA | −8.0 (10.14) | 17.6 (9.73) | −25.6 (−53.9, 2.8) | 0.0756 |
| Percent change from baseline in the total volume of HO lesions as assessed by CT at week 28 (AHOC) | MMRM | 7.0 (20.87) | 34.9 (19.90) | −27.81(−86.1, 30.5) | 0.3407 |
| Time weighted average of change from baseline in daily pain due to FOP, as measured using the daily NRS over 28 weeks in AHO | ANCOVA | −0.51 (0.231) | −0.17 (0.205) | −0.34 (−0.96, 0.27) | 0.2656 |
| Time weighted average of change from baseline in daily pain due to FOP, as measured using the daily NRS over 28 weeks in AHOC | ANCOVA | −0.48 (0.237) | −0.12 (0.223) | −0.36 (−1.01, 0.29) | 0.2653 |

AHO = patients with at least 1 active HO lesion;
AHOC = patients with at least 1 active HO lesion and classic ACVR1R206H mutation;
ANCOVA = analysis of covariance;
MMRM = mixed model with repeated measures.
Assessments provided by the adjudicated selected reader at Week 28 were used for the primary analyses (Reader 1 was selected if no adjudication was performed at Week 28).

Analyses of the Inhibition of New Lesions by Garetosmab

Figure 6:
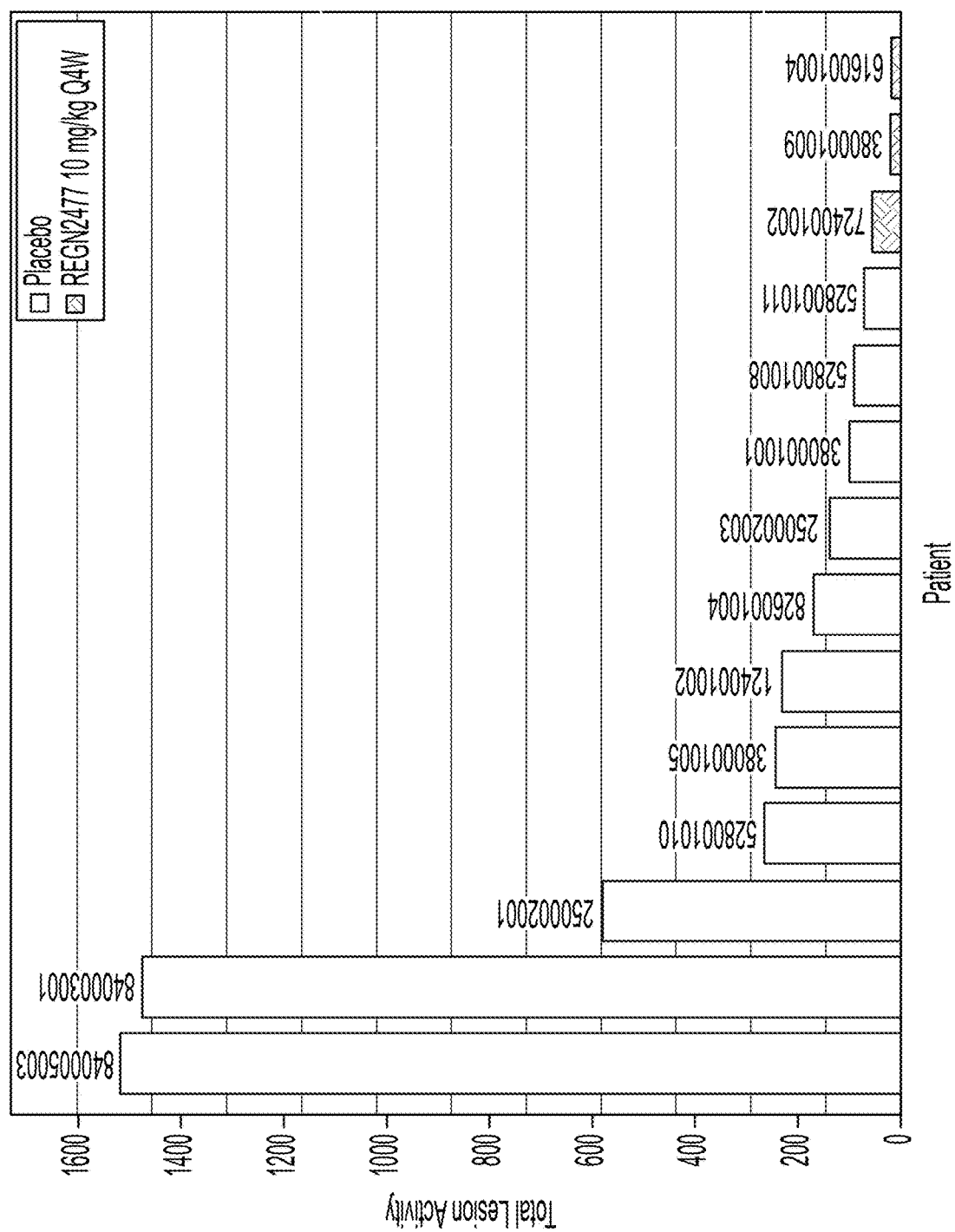
FIG. 6 depicts total lesion activity for new lesions by $^{18}$F-NaF PET at week 28 for patients with new lesions in the double-blind period in active HO analysis set (AHO).

Analyses of the key pre-specified secondary, exploratory and post-hoc analyses in AHO population below (Table 4) demonstrate that the reductions in garetosmab arm compared to placebo in total lesion activity by PET and in total volume of HO lesions by CT were mainly driven by a nearly 90% decrease in multiple endpoints related to the new HO lesion growth such as the incidence, rate, lesion activity (PET) and volume (CT) of new HO lesions. The number of new PET lesions over 28 weeks was substantially reduced in garetosmab arm compared to placebo (87.4% decrease in rate of new lesions). The number of new PET lesions was markedly lower in garetosmab group compared to placebo (3 versus 29). The mean total lesion activity per patient associated with new lesions was lower in garetosmab group compared to placebo (5.22/pt versus 205.99/pt). The total lesion activity associated with the new lesions in patients who developed new PET lesions in garetosmab group was also substantially lower compared to placebo group (FIG. 6).

Figure 7:
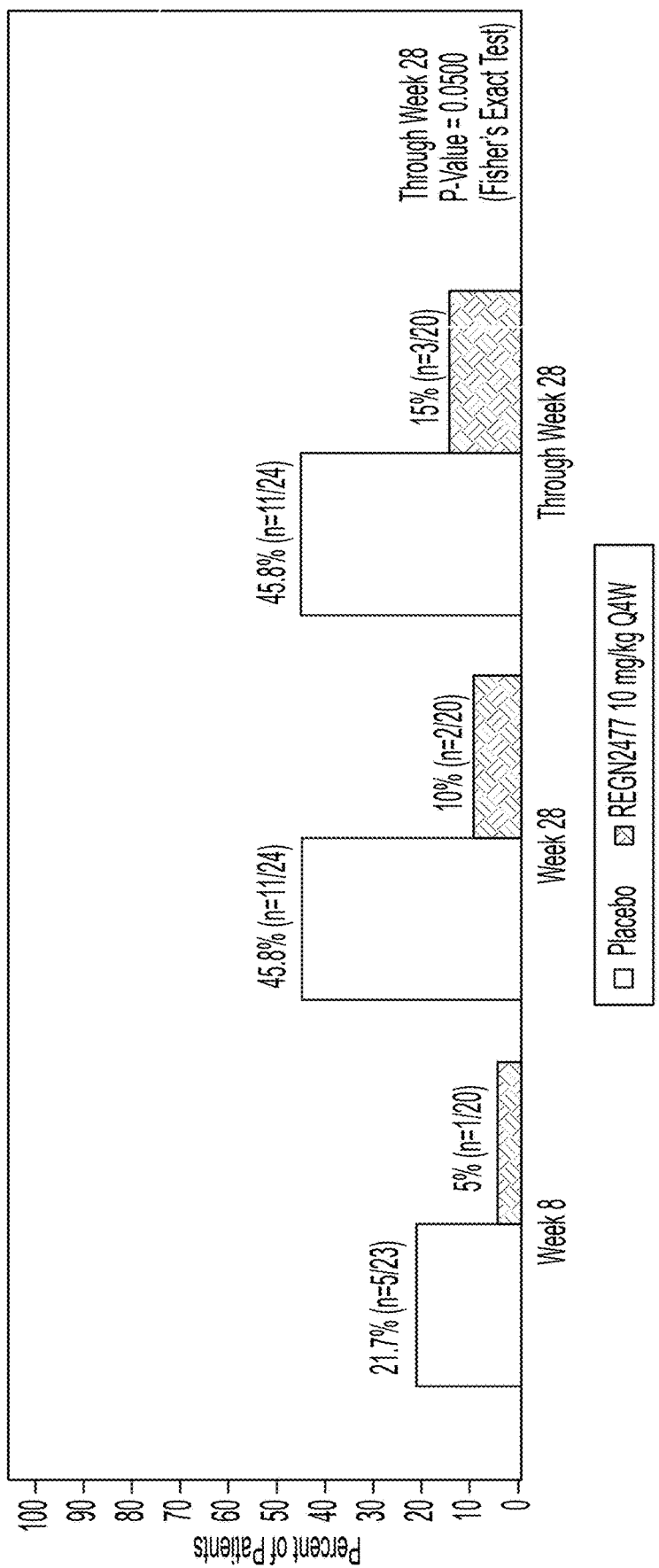
FIG. 7 depicts the percent of patients with new HO Lesions by $^{18}$F-NaF PET in active HO analysis set (AHO).
Figure 8:
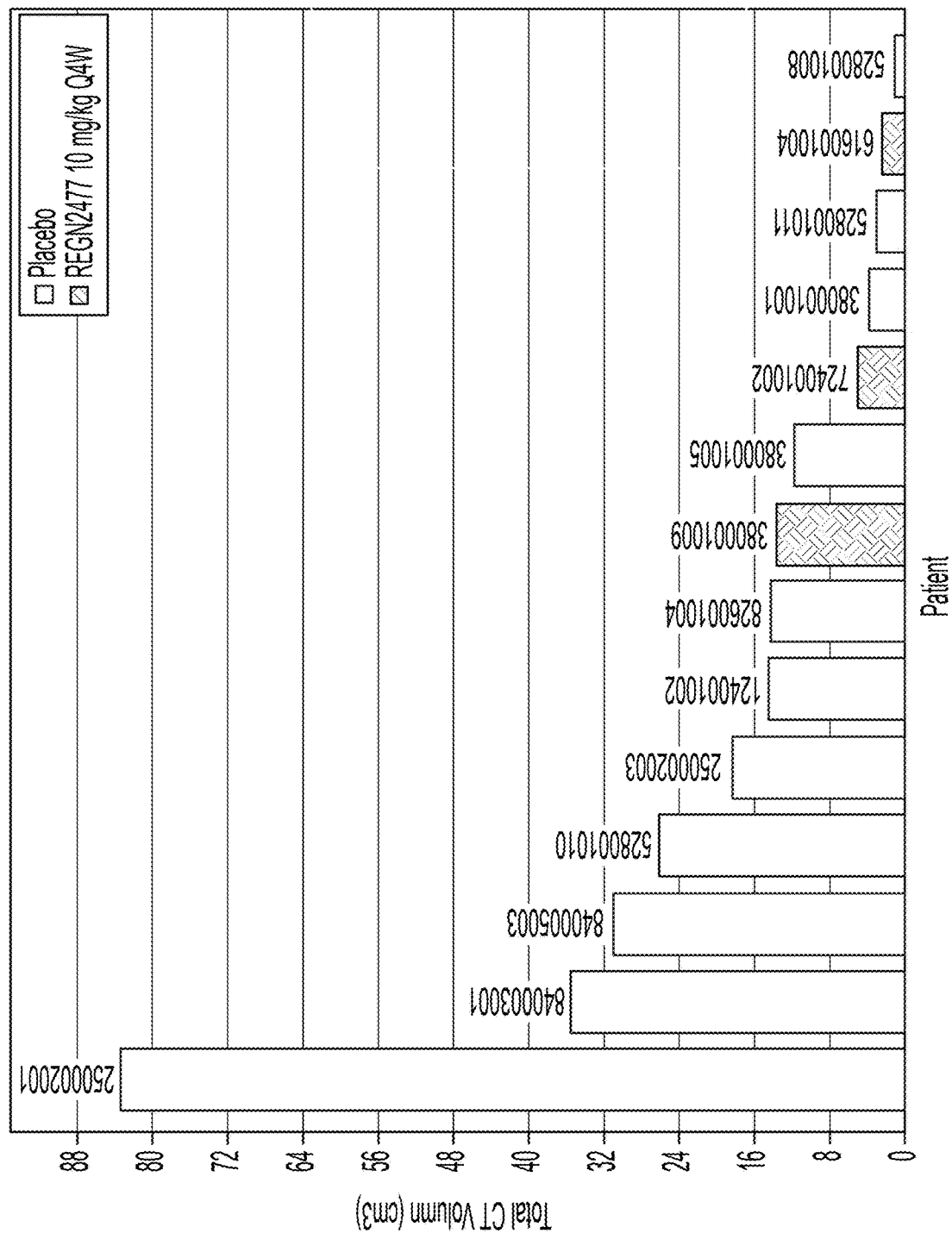
FIG. 8 depicts the total new lesion volume by CT at week 28 for patients with new lesions in the double-blind period in active HO analysis set (AHO).
Figure 9:
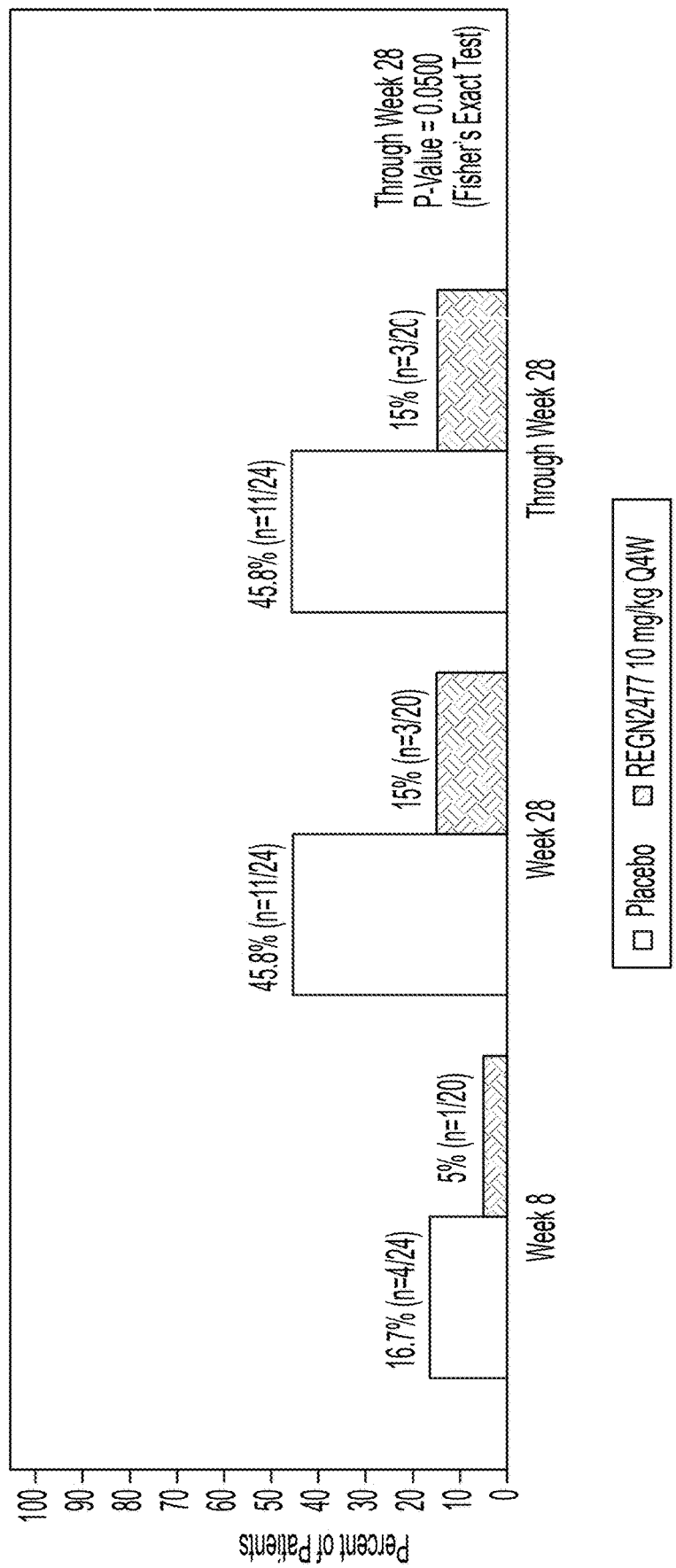
FIG. 9 depicts the percent of patients with new HO lesions by CT in active HO analysis set (AHO).

The percent of patients who developed new PET lesions over 28 weeks were lower in garetosmab arm compared to placebo (15% vs 46%, FIG. 7). The number of new CT lesions over 28 weeks was lower in garetosmab arm compared to placebo (86.7% decrease in the rate of new lesions). There were 3 new CT lesions in garetosmab group compared to 27 new CT lesions in placebo group. The mean per patient total CT volume associated new lesion was lower in garetosmab group compared to placebo (1.06 cm$^3$/pt versus 10.21 cm$^3$/pt). Total CT volume associated with the new lesions in patients who developed new CT lesions was also lower in garetosmab group compared to placebo group (FIG. 8). The percent of patients who developed new CT lesions over 28 weeks was lower in garetosmab arm compared to placebo (15% vs 46%, FIG. 9). Additionally, the proportion of patients with flare-ups as assessed by patient diary was well as with investigator-reported adverse events of flare-ups was lower in garetosmab arm compared to placebo. Similar results were observed in AHOC population.

TABLE 4

Other Supportive Efficacy Results (AHO)

| | Endpoint (stat. method) | REGN2477 | Placebo | Reduction | p-Value |
|---|---|---|---|---|---|
| PET lesions | Number of HO lesions by PET per scan over 28 works (negative binomial model) | 3.5 | 4.8 | 27% decrease (0.729 rate ratio) | 0.0294 |
| New PET lesions | Percent of patients with new bone lesions measured by PET over 28 weeks (Fisher's exact test) | 15% (3/20) | 46% (11/24) | 67.4% reduction in risk (relative risk = 0.326) | 0.0500 |
| New CT lesions (post-hoc) | Percent of patients with new bone lesions measured by CT over 28 weeks (Fisher's exact test) | 15% (3/20) | 46% (11/24) | 67.4% reduction in risk (relative risk = 0.326) | 0.0500 |

TABLE 4-continued

Other Supportive Efficacy Results (AHO)

| | Endpoint (stat. method) | REGN2477 | Placebo | Reduction | p-Value |
|---|---|---|---|---|---|
| New PET lesions (post-hoc) | Number of new bone lesions measured by PET over 28 weeks (negative binomial model) | Rate: 0.15 Count: 3 Lesion activity/ pt: 34.8 | Rate: 1.19 Count: 29 Lesion activity/ pt: 449.4 | 87.4% decrease (0.126 rate ratio) | 0.0063 |
| New CT lesions (post-hoc) | Number of new CT bone lesions per patient over 28 works (negative binomial model) | Rate: 0.15 Count: 3 volunse/ pt: 7.1 cm$^3$ | 113 count: 27, Volume: 22.3 cm$^3$ | 86.7% decrease (0.133 rate ratio) | 0.0085 |
| New PET lesions (post-hoc) | Total lesion activity is new lesions per patient by PET at Week 28 (Wilcoxon test) | 5.22 | 205.99 | 97% relative reduction | 0.0086 |
| New CT lesions (post-hoc) | Total volume of new lesions per patient by CT at Week 28 (Wilcoxon test) | 1.06 | 10.21 | 90% relative reduction | 0.0172 |
| Flare ups | Percent of patients with flare-ups, assessed by patient e-diary (Fisher's exact test) | 35% (7/20) | 71% (17/24) | 50.7% reduction in risk (relative risk = 0.493) | 0.0324 |
| Flare ups | Percent of patients with investigator-assessed flare-ups (Fisher's exact) | 10% (2/20) | 42% (10/24) | 76.2% reduction in risk (relative risk = 0.238) | 0.0389 |

Safety Results

During the 28-week double blind treatment period, treatment emergent adverse events (TEAEs) occurred in 100% of patients in both garetosmab and placebo groups; the majority were mild to moderate in severity. Notable imbalances in TEAEs for Garetosmab and placebo groups, respectively, included epistaxis (50.0% vs 16.7%) and skin events (madarosis [loss of eyebrows; 25.0% vs 0%], acne [30.0% vs 8.3%] and a composite of skin infections including abscess, carbuncle, folliculitis, and furuncle). When patients in the placebo group transitioned to garetosmab in the on-going open label period (Period 2), the frequency of reports of epistaxis and the above skin events increased. The frequency of infusion reactions during the 28-week double-blind period was balanced between placebo and garetosmab groups (placebo: 6/24 (25%); Garetosmab: 5/20 (25%)). During Period 2, 4 patients (9.3%) presented infusion reactions while receiving garetosmab. Serious adverse events (SAEs) were reported in 20% and 8.3% of garetosmab and placebo treated groups, respectively, during Period 1. One SAE (epistaxis) in a patient assigned to the garetosmab group that occurred during Period 1 resulted in hospitalization for nasal packing. This event was characterized as suspected unexpected serious adverse reaction (SUSAR). The patient fully recovered and continued in the study. During the open-label period, and until the data cut-off date, 3 SAEs were reported. Two patients developed SAEs of abscess during Period 2 that required hospitalization for incision and drainage (subcutaneous abscess and cyst abscess, respectively reported by investigators as related and not related to study drug). The abscesses resolved and patients continued to receive garetosmab after a temporary treatment interruption. A third patient had a SAE of severe head trauma due to a fall, followed by death. The head trauma occurred during Period 3, after the patient had received 16 infusions of garetosmab, and was assessed as not related to the study drug by the investigator. Nineteen out of 20 garetosmab group patients and 24 out of 24 placebo group patients completed Period 1. The patient that discontinued garetosmab in the 28-week treatment period had an adverse event of pyrexia assessed by the investigator as mild on severity and not related to study drug. Recurrence of pyrexia, after the patient had presented 2 SAEs (hospitalizations) of pneumonia, one of them complicated with sepsis, led the investigator to discontinue the patient from the study. Among other clinical features this patient's medical history included severe restrictive lung disease, bronchiectasis and skeletal deformity. One patient in the open-label follow up treatment period (Period 3), died due to head trauma unrelated to treatment.

CONCLUSION

Garetosmab decreased total lesion activity (both new and existing) from baseline over 28 weeks (time weighted average ls difference ~25%, p=0.0741). This was largely driven by an approximate 90% decrease in the incidence, rate, activity (PET) and volume (CT) of new lesions. In ultra-rare conditions such as FOP, in which it is not feasible to perform a large enough study to ensure sufficient power, it is common to accept a Type I error rate of 10% in order to avoid making Type 2 error. In this light, the overall efficacy results are compelling and strongly support that garetosmab reduces the formation of new HO in patients with FOP. The results also support the interpretation that activin A does not seem to play a key role in the progression of existing HO lesions selected by PET/CT at baseline. Treatment with garetosmab demonstrated an acceptable safety profile with a low incidence of infusion reactions and SAEs. The majority of TEAEs were mild to moderate in severity. Notable imbalances in TEAEs included epistaxis, acne, madarosis and a composite of skin infections including abscesses, carbuncle folliculitis and furuncle. In this ongoing study, and all patients have transitioned to the open label periods (Periods 2 and 3). The cross-over of placebo patients to garetosmab allows the confirmation at week 56 that garetosmab treatment leads to the marked reduction of new bone lesion formation compared to control (where "control" is the measurements of these same patients during the preceding placebo treatment period). The week 56 data will also provide information on the persistence of treatment effect in patients who continue their garetosmab treatment. In summary, the safety and efficacy data from the study show a positive benefit-risk of garetosmab for the treatment of adult patients with FOP. Blocking of activin A with garetosmab provides an opportunity to change the course of disease for the long-suffering FOP patients.

Study Objectives

Primary Objective

The primary safety objective of the study was to assess the safety and tolerability of garetosmab in patients with FOP. The primary efficacy objective of the study was to assess the effect of garetosmab versus placebo on the change from baseline in HO in patients with FOP, as determined by $^{18}$F-NaF uptake in HO lesions by PET and in total volume of HO lesions by CT. Secondary Objectives The secondary objectives of the study were:

To compare the effect of garetosmab versus placebo on pain due to FOP, as measured by the area under the curve (AUC) for pain based on daily pain NRS scores.

To assess the effect of garetosmab versus placebo on the change from baseline in HO, as determined by the number of new HO lesions identified by $^{18}$F-NaF PET or by CT.

To assess the effect of garetosmab versus placebo on the change from baseline in 18F-NaF standardized uptake value maximum (SUVmax) of individual active HO site(s) by PET.

To assess the effect of garetosmab, between week 28 and week 56, on the number, activity, and volume of HO lesions identified by $^{18}$F-NaF PET or by CT in patients who switch from placebo to garetosmab at week 28 versus the same patients between baseline and week 28.

To assess the effect of garetosmab versus placebo on the change from baseline in biochemical markers of bone formation.

To characterize the concentrations of total activin A at baseline and over time following the first dose of study drug.

To characterize the concentration-time profile (pharmacokinetic [PK]) profile of garetosmab in patients with FOP.

To assess the immunogenicity of garetosmab.

Study Design

This was a phase 2, randomized, double-blind, placebo-controlled, study designed to evaluate the safety, tolerability, PK, and effects on heterotopic bone formation of repeated doses of 10 mg/kg IV garetosmab Q4W in adult patients with FOP. As depicted in the study design schematics (FIG. 1), this study consisted of a screening/baseline period (day −28 to day −1), two 6-month treatment periods, and a follow-up treatment period (Period 3).

During the screening/baseline period, all patients underwent the informed consent process and screening/baseline procedures. In the double-blind treatment period (Period 1), patients were randomized to receive garetosmab at 10 mg/kg dose or matching placebo, administered IC Q4W through week 24, for a total of 7 doses. Randomization was stratified by gender, classic ACVR1[R206H] mutation/different ACVR1 mutations, and by presence/absence of baseline active HO lesions as determined by $^{18}$F-NaF-PET/CT. In open-label treatment period (Period 2), all patients who completed the double-blind treatment period received garetosmab administered IV at a dose of 10 mg/kg Q4W through week 52, for a total of 7 doses. The patients who completed Period 2 continue to receive Garetosmab through week 76 or beyond in Period 3. Imaging procedures are performed at baseline, week 8, week 28, week 56, and week 76.

Statistical Methods

Analysis Populations

In accordance with guidance from the International Conference of Harmonization of Technical Requirements for Registration of Pharmaceuticals for Human Use (ICH) guideline ICH E9 Statistical Principles for Clinical Trials (1998), the following population of analysis were used for all statistical analysis:

Baseline-Active HO Analysis Set (AHO): the baseline-active HO analysis set (AHO) included all randomized patients who had at least one active HO lesion at baseline; it was based on the treatment allocated (as randomized).

Baseline-Active HO Classic ACVR1[R206H] Mutation Analysis Set (AHOC): the baseline-active HO classic ACVR1 [R206H] mutation analysis set (AHOC) included all randomized patients with the classic ACVR1 [R206H] mutation and who had at least one active HO lesion(s) at baseline, as defined by 18F-NaF PET positivity; it was based on the treatment allocated (as randomized).

The Safety Analysis Set (SAF): the safety analysis set (SAF) included all randomized patients who received any study drug. Actual treatment received was used in the analyses of safety.

Analysis of Efficacy Variables

Efficacy variables for the study consisted of assessments from imaging procedures, clinical endpoints and biomarkers of bone formation.

Multiplicity Consideration: the study had four primary and two secondary efficacy objectives. To control the type-I error rate, a hierarchical testing procedure was applied at a 2-sided 5% significance level, key secondary efficacy endpoints were tested only if statistical significance was established for all primary endpoints. The order of testing sequence for primary and key secondary efficacy endpoints was as following:

Primary: Time-weighted average (standardized AUC) of the percent change from baseline in total lesion activity by $^{18}$F-NaF PET over 28 weeks in AHO
↓
Primary: Percent change from baseline in the total volume of HO lesions as assessed by CT at week 28 in AHO
↓
Primary: Time-weighted average (standardized AUC) of the percent change from baseline in total lesion activity $^{18}$F-NaF PET over 28 weeks in AHOC
↓
Primary: Percent change from baseline in the total volume of HO lesions as assessed by CT at week 28 in AHOC
↓
Key Secondary: Time-weighted average (standardized AUC) of the change from baseline in daily pain due to FOP, as measured using the daily NRS over 28 weeks in AHO
↓
Key Secondary: Time-weighted average (standardized AUC) of the change from baseline in daily pain due to FOP, as measured using the daily NRS over 28 weeks in AHOC Primary Efficacy Endpoints:
Time-Weighted Average (Standardized AUC) of the Percent Change from Baseline in Total Lesion Activity by $^{18}$F-NaF PET Over 28 Weeks in AHO The AUC of the percent change from baseline in total lesion activity by 18F-Naf PET over 28 weeks was calculated for each patient. Nominal time (i.e. Week 8 and Week 28) and not the actual time was used in the calculation of the AUC. If imaging scan for week 8 was missing, linear interpolation of % change between the baseline and week 28 was used to calculate AUC. If imaging scan for week 28 was missing, % change at week 8 was carried forward to week 28 for calculating AUC. Time weighted average (standardized AUC) was derived as the AUC of percent change from baseline in total lesion activity by 18F-Naf PET over 28 weeks divided by 28. The analysis of covariance (ANCOVA) model was used to analyze time weighted average of percent change over 28 weeks. The model included treatment, gender and baseline total lesion activity as a covariate. ACVR1 mutation type was excluded from the model because all the patients except two patients had ACVR1 classic mutation. Difference in LS mean change from baseline, corresponding 95% CI and the p-value were provided from ANCOVA model for comparison for garetosmab group against placebo group.

Percent Change from Baseline in the Total Volume of HO Lesions as Assessed by CT at Week 28 in AHO Percent change from baseline in the total volume of HO lesions as assessed by CT at week 8 and 28 weeks was analyzed in AHO analysis set using a MMRM model. Model contains treatment, gender, ACVR1 mutation type (classic, non-classic), visit (Week 8, and 28), baseline total volume and treatment-by-visit interaction. An unstructured covariance was used to account for within-patient correlation between time. Difference in LS mean change from baseline, the corresponding 95% CI and the p-value was provided from MMRM model for comparison for garetosmab group against placebo group.

Time-Weighted Average (Standardized AUC) of the Percent Change from Baseline in Total Lesion Activity by $^{18}$F-NaF PET Over 28 Weeks in AHOC Time-weighted average (standardized AUC) of the percent change from baseline in total lesion activity by $^{18}$F-NaF PET over 28 weeks in AHOC was analyzed using the same method as for first primary endpoint in AHO. The model contained independent variables of treatment, gender, visit (Week 8, and 28), treatment-by-visit interaction and baseline total lesion activity.

Percent Change from Baseline in the Total Volume of HO Lesions as Assessed by CT at Week 28 in AHOC Percent change from baseline in the total volume of HO lesions as assessed by CT at week 28 in AHO was analyzed in the same method as for second primary endpoint in AHO. This model contained treatment, gender, visit (week 8, and week 28), baseline total volume and treatment-by-visit interaction.

Key Secondary Efficacy Endpoints:
Time-Weighted Average (Standardized AUC) Change from Baseline in Daily Pain Due to FOP, as Measured Using the Daily NRS Over 28 Weeks in AHO Time weighted average of change from baseline in daily pain scores (average of current pain, worst pain, and least pain) was calculated for each patient. If the pain score for intermediate days were missing, linear interpolation of change between the two adjacent measurements was used to calculate time weighted average. If missing monotone, the post-baseline last observation carried forward (LOCF) method was used to impute missing values. Time-weighted average change in daily pain over week 28 was analyzed in AHO using the ANCOVA model. This model contained treatment, gender, ACVR1 mutation type (classic, non-classic), and baseline daily pain score.

Time-Weighted Average (Standardized AUC) Change from Baseline in Daily Pain Due to FOP, as Measured Using the Daily NRS Over 28 Weeks in AHOC Time-weighted average (standardized AUC) change from baseline in daily pain due to FOP, as measured using the daily NRS over 28 weeks in AHOC was analyzed in the same methods as previous key secondary endpoint (in AHO). This model contained treatment, gender, and baseline daily pain score.

Analysis of Safety Data

The summary of safety and tolerability were performed for all patients in SAF. The safety analysis was based on the reported AEs, clinical laboratory evaluations and vital signs. Thresholds for Treatment Emergent Potentially Clinically Significant Values (PCSV) in laboratory variables and vital signs were defined in SAP. The baseline when determining treatment-emergent PCSV refers to the baseline value of current study.

Extension of 28 Week Study

Study participants who received garetosmab continued to do so through week 56 in an extension of the study. Furthermore, study participants receiving placebo were allowed to receive garetosmab during the extension period. Placebo patients who received garetosmab during the extension period had similar reductions in the number of new lesions, lesion volume, and pain scores as seen in the treatment group during the blinded period (i.e., through week 28).

The invention claimed is:

1. A method of decreasing the formation of new heterotopic ossification lesions in a human subject with fibrodysplasia ossificans progressiva (FOP), the method comprising administering to the human subject a therapeutically effective amount of an activin A antagonist, thereby decreasing the formation of new heterotopic ossification lesions in the human subject, wherein the activin A antagonist is an anti-activin A antibody, or antigen-binding fragment thereof, comprising the following six CDR sequences:
(a) a heavy chain complementarity determining region (HCDR) 1 having the sequence GGSFSSHF (SEQ ID NO: 2);
(b) an HCDR2 having the sequence ILYTGGT (SEQ ID NO: 3);
(c) an HCDR3 having the sequence ARARSGITFTGIIVPGSFDI (SEQ ID NO: 4);
(d) a light chain complementarity determining region (LCDR) 1 having the sequence QSVSSSY (SEQ ID NO: 6);
(e) an LCDR2 having the sequence GAS (SEQ ID NO: 7); and
(f) an LCDR3 having the sequence QQYGSSPWT (SEQ ID NO: 8).

2. The method of claim 1, wherein the human subject exhibits a decrease in number of new heterotopic ossification lesions of at least 5%, at least 10%, at least 20%, at least about 25%, at least 30%, at least 40%, at least 50%, at least 60%, at least 70%, at least 80%, at least 90%, at least 5%-90%, at least 10%-90%, at least 20%-90%, at least 30%-90%, at least 40%-90%, at least 50%-90%, at least 60%-90%, at least 70%-90%, at least 80%-90%, at least 5%-80%, at least 5%-70%, at least 5%-60%, at least 5%-50%, at least 5%-40%, at least 5%-30%, at least 5%-20%, or at least 5%-10%, relative to a control.

3. The method of claim 1, wherein the human subject exhibits a decrease in new heterotopic ossification lesion volume by at least 5%, at least 10%, at least 15%, at least 20%, at least 25%, at least 30%, at least 40%, at least 50%, at least 5%-50%, at least 10%-50%, at least 20%-50%, at least 30%-50%, at least 40%-50%, at least 5%-40%, at least 5%-30%, at least 5%-20%, or at least 5%-10%, relative to a control.

4. The method of claim 1, wherein the human subject exhibits a decrease in a rate of new heterotopic ossification lesion growth and mineralization of at least 5%, at least 10%, at least 20%, at least 30%, at least 40%, at least 50%, at least 5%-50%, at least 10%-50%, at least 20%-50%, at least 30%-50%, at least 40%-50%, at least 5%-40%, at least 5%-30%, at least 5%-20%, or at least 5%-10%, relative to a control.

5. The method of claim 1, wherein the human subject exhibits a decrease in total lesion activity (TLA) of the heterotopic ossification lesions of at least 5%, at least 10%, at least 15%, at least 20%, at least 25%, at least 30%, at least 40%, at least 50%, at least 60%, at least 70%, at least 80%, at least 5%-80%, at least 10%-80%, at least 20%-80%, at least 30%-80%, at least 40%-80%, at least 50%-80%, at least 60%-80%, at least 70%-80%, at least 5%-70%, at least 5%-60%, at least 5%-50%, at least 5%-40%, at least 5%-30%, at least 5%-20%, or at least 5%-10%, relative to a control.

6. The method of claim 1, wherein the human subject exhibits a decrease in daily average pain-NRS of about 0.2-fold, 0.5-fold, 1-fold, 1.5-fold, 2-fold, 3-fold, 0.2 to 3-fold, 0.5 to 3-fold, 1 to 3-fold, 1.5 to 3-fold, 2 to 3-fold, 2.5 to 3-fold, 0.2 to 2.5-fold, 0.2 to 2-fold, 0.2 to 1.5-fold, 0.2 to 1-fold, or 0.2 to 0.5-fold, relative to a control.

7. The method of claim 1, wherein the therapeutically effective amount of an activin A antagonist reduces the occurrence of painful flare-ups in the human subject, relative to a control.

8. The method of claim 1, wherein the new heterotopic ossification lesions are analyzed by a Positron emission tomography (PET) scan, a computed tomography (CT) scan, or a combination thereof.

9. The method of claim 8, wherein the PET scan analysis is performed by administration of radiolabeled $^{18}$F sodium fluoride ($^{18}$F-NaF) to the human subject.

10. The method of claim 1, wherein the therapeutically effective amount of an activin A antagonist is administered to the human subject for at least 8 weeks.

11. The method of claim 1, wherein the human subject requires surgery.

12. The method of claim 1, wherein the activin A antagonist is administered in combination with a second therapy.

13. The method of claim 1, wherein the anti-Activin A antibody, or antigen-binding fragment thereof,
(a) is a chimeric, veneered, humanized or human antibody, or antigen-binding fragment thereof; and/or
(b) is a human kappa IgG1 antibody.

14. The method of claim 1, wherein the anti-activin A antibody, or antigen-binding fragment thereof, comprises a heavy chain variable region having at least 90% identity with SEQ ID NO:1 and a light chain variable region having at least 90% identity with SEQ ID NO:5.

15. The method of claim 14, wherein the anti-activin A antibody, or antigen-binding fragment thereof, comprises a heavy chain variable region having at least 95% identity with SEQ ID NO:1 and a light chain variable region having at least 95% identity with SEQ ID NO:5.

16. The method of claim 15, wherein the anti-activin A antibody, or antigen-binding fragment thereof, comprises a heavy chain variable region comprising SEQ ID NO:1 and a light chain variable region comprising SEQ ID NO:5.

17. The method of claim 16, wherein the anti-activin A antibody, or antigen-binding fragment thereof, comprises a heavy chain comprising SEQ ID NO:25 and a light chain comprising SEQ ID NO:26.

* * * * *

UNITED STATES PATENT AND TRADEMARK OFFICE
CERTIFICATE OF CORRECTION

| | | |
|---|---|---|
| PATENT NO. | : 12,344,665 B2 | Page 1 of 1 |
| APPLICATION NO. | : 17/144385 | |
| DATED | : July 1, 2025 | |
| INVENTOR(S) | : Economides et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 450 days.

Signed and Sealed this
Sixteenth Day of December, 2025

John A. Squires
*Director of the United States Patent and Trademark Office*

SEQUENCE LISTING

```
<160> NUMBER OF SEQ ID NOS: 28

<210> SEQ ID NO 1
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser
        115                 120                 125

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Gly Ser Phe Ser Ser His Phe
1               5

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ile Leu Tyr Thr Gly Gly Thr
1               5

<210> SEQ ID NO 4
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ala Arg Ala Arg Ser Gly Ile Thr Phe Thr Gly Ile Ile Val Pro Gly
1               5                   10                  15

Ser Phe Asp Ile
            20

<210> SEQ ID NO 5
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 6
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Ser Val Ser Ser Ser Tyr
1               5

<210> SEQ ID NO 7
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Ala Ser
1

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Gln Tyr Gly Ser Ser Pro Trp Thr
1               5

<210> SEQ ID NO 9
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

```
<400> SEQUENCE: 9

Glu Val Gln Leu Val Glu Ser Gly Gly Gly Leu Val Gln Pro Gly Arg
1               5                   10                  15

Ser Leu Arg Leu Ser Cys Lys Ala Ser Gly Phe Ala Phe Asp Asp Phe
            20                  25                  30

Ala Met His Trp Val Arg Gln Ala Pro Gly Lys Gly Leu Glu Trp Val
        35                  40                  45

Ser Gly Ile Val Trp Asn Ser Gly Asp Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Thr Glu Asp Thr Ala Leu Tyr Phe Cys
                85                  90                  95

Val Lys Asp Met Val Arg Gly Leu Met Gly Phe Asn Tyr Tyr Gly Met
            100                 105                 110

Asp Val Trp Gly Gln Gly Thr Thr Val Thr Val Ser Ser
        115                 120                 125

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Phe Ala Phe Asp Asp Phe Ala
1               5

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Val Trp Asn Ser Gly Asp Ile
1               5

<210> SEQ ID NO 12
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Val Lys Asp Met Val Arg Gly Leu Met Gly Phe Asn Tyr Tyr Gly Met
1               5                   10                  15

Asp Val

<210> SEQ ID NO 13
<211> LENGTH: 107
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Thr Tyr
                20                  25                  30

Leu Val Trp Tyr Arg Gln Arg Pro Gly Gln Ala Pro Ser Leu Leu Ile
            35                  40                  45

Tyr Asp Ala Ser Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 14
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gln Thr Ile Ser Thr Tyr
1               5

<210> SEQ ID NO 15
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Ala Ser
1

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Gln Arg Ser Asn Trp Pro Ile Thr
1               5

<210> SEQ ID NO 17
<211> LENGTH: 106
<212> TYPE: PRT
<213> ORGANISM: Artificial Sequence
<220> FEATURE:
<221> NAME/KEY: source
```

<223> OTHER INFORMATION: /note="Description of Artificial Sequence:
        Synthetic polypeptide"

<400> SEQUENCE: 17

```
Ser Tyr Glu Val Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105
```

<210> SEQ ID NO 18
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic polypeptide"

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110

Gly Gln Gly Thr Met Val Thr Val Ser Ser
        115                 120
```

<210> SEQ ID NO 19
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic peptide"

<400> SEQUENCE: 19

```
Ser Gly Asp Lys Leu Gly Asp Lys Tyr Ala Cys
1               5                   10
```

<210> SEQ ID NO 20

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln Asp Ser Lys Arg Pro Ser
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Ala Trp Asp Ser Ser Thr Ala Val
1               5

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Tyr Thr Phe Thr Ser Tyr Gly Leu Ser
1               5                   10

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Trp Ile Ile Pro Tyr Asn Gly Asn Thr Asn Ser Ala Gln Lys Leu Gln
1               5                   10                  15

Gly

<210> SEQ ID NO 24
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Arg Asp Tyr Gly Val Asn Tyr Asp Ala Phe Asp Ile
1               5                   10

<210> SEQ ID NO 25
<211> LENGTH: 457
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Cys Pro Pro Cys Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
    370                 375                 380
```

```
Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
            435                 440                 445

Lys Ser Leu Ser Leu Ser Leu Gly Lys
450                 455
```

<210> SEQ ID NO 26
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 27

Thr Gly Gly Gly Gly
1               5

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser Gly Gly Gly Gly
1               5
```